(12) United States Patent
Lubenau

(10) Patent No.: US 10,905,752 B2
(45) Date of Patent: Feb. 2, 2021

(54) VEGFR-2 TARGETING DNA VACCINE FOR COMBINATION THERAPY

(71) Applicant: VAXIMM AG, Basel (CH)

(72) Inventor: Heinz Lubenau, Neustadt an der Weinstrasse (DE)

(73) Assignee: VAXIMM AG, Basel (CH)

( * ) Notice: Subject to any disclaimer, the term of this patent is extended or adjusted under 35 U.S.C. 154(b) by 0 days.

(21) Appl. No.: 15/737,659

(22) PCT Filed: Jun. 16, 2016

(86) PCT No.: PCT/EP2016/001004
§ 371 (c)(1),
(2) Date: Dec. 18, 2017

(87) PCT Pub. No.: WO2016/202459
PCT Pub. Date: Dec. 22, 2016

(65) Prior Publication Data
US 2018/0250345 A1    Sep. 6, 2018

(30) Foreign Application Priority Data
Jun. 18, 2015  (EP) .................................. 15001803

(51) Int. Cl.
| | | |
|---|---|---|
| A61K 39/00 | (2006.01) | |
| A61K 39/39 | (2006.01) | |
| A61K 39/395 | (2006.01) | |
| A61K 35/74 | (2015.01) | |
| A61P 35/00 | (2006.01) | |
| A61P 37/06 | (2006.01) | |
| A61K 45/06 | (2006.01) | |

(52) U.S. Cl.
CPC .......... *A61K 39/0011* (2013.01); *A61K 35/74* (2013.01); *A61K 39/001109* (2018.08); *A61K 39/001153* (2018.08); *A61K 39/001168* (2018.08); *A61K 39/001182* (2018.08); *A61K 39/39* (2013.01); *A61K 39/39558* (2013.01); *A61K 45/06* (2013.01); *A61P 35/00* (2018.01); *A61P 37/06* (2018.01); *A61K 2039/522* (2013.01); *A61K 2039/523* (2013.01); *Y02A 50/30* (2018.01)

(58) Field of Classification Search
CPC ........ A61K 2039/522; A61K 2039/523; A61K 39/0011; A61K 2039/53; A61K 2039/542; A61K 2039/545; A61K 2039/57; A61K 31/7068; A61K 35/74; A61K 39/0275; A61K 39/39; A61K 39/39558; A61K 45/06; A61P 35/00; A61P 37/06; C12N 1/36; C12N 15/113; C12N 15/1135; C12N 15/74; C12N 1/20; C12N 2310/14; C12N 2310/141; C12N 2310/17; C12N 2310/531; C12N 2320/32; C12R 1/42; Y02A 50/484; C07K 14/71
See application file for complete search history.

(56) References Cited

U.S. PATENT DOCUMENTS

| | | | |
|---|---|---|---|
| 9,415,098 B2 * | 8/2016 | Lubenau | A61K 39/0011 |
| 2014/0248211 A1 * | 9/2014 | Bender | A61K 45/06 424/1.49 |
| 2014/0349274 A1 * | 11/2014 | Lubenau | C07K 14/71 435/3 |
| 2016/0130345 A1 * | 5/2016 | Fotin-Mleczek | A61K 39/39 424/172.1 |

FOREIGN PATENT DOCUMENTS

| | | | |
|---|---|---|---|
| WO | WO 2003/073995 | | 9/2003 |
| WO | WO 2013/091898 A1 * | | 1/2014 |
| WO | WO 2014/005683 A1 | | 1/2014 |
| WO | WO 2014/173542 A1 | | 10/2014 |

OTHER PUBLICATIONS

Hanif et al. Asian Pac J. Cancer Prey. 18: 3-9, 2017.*
International Search Report regarding International Application No. PCT/EP2016/001004 dated Jun. 16, 2016.
Binder et al., "Antigen-specific bacterial vaccine combined with anit-PD-L1 rescues dysfunctional endogenous T cells to reject long-established cancer," Cancer Immunol. Res. 1:123-133, 2013.
Reisfeld et al., "DNA vaccines suppress tumor growth and metastases by the induction of anti-angiogenesis," Immunological Reviews 199:181-190, 2004.
Sharma et al., "Immune Checkpoint Targeting in Cancer Therapy: Towards Combination Strategies with Curative Potential," Cell 161(2):205-214, 2015.

* cited by examiner

*Primary Examiner* — Sarvamangala Devi
(74) *Attorney, Agent, or Firm* — Dentons US LLP

(57) ABSTRACT

The present invention relates to an attenuated strain of *Salmonella* comprising at least one copy of a DNA molecule comprising an expression cassette encoding a VEGF receptor protein, for use in the treatment of cancer, wherein the treatment further comprises the administration of at least one further anti-cancer agent. The present invention further relates to a pharmaceutical composition comprising an attenuated strain of *Salmonella* comprising at least one copy of a DNA molecule comprising an expression cassette encoding a VEGF receptor protein, wherein the pharmaceutical composition further comprises at least one further attenuated strain of *Salmonella* comprising at least one copy of a further DNA molecule comprising a further expression cassette encoding a tumor antigen or a tumor stroma antigen.

Figure 16:
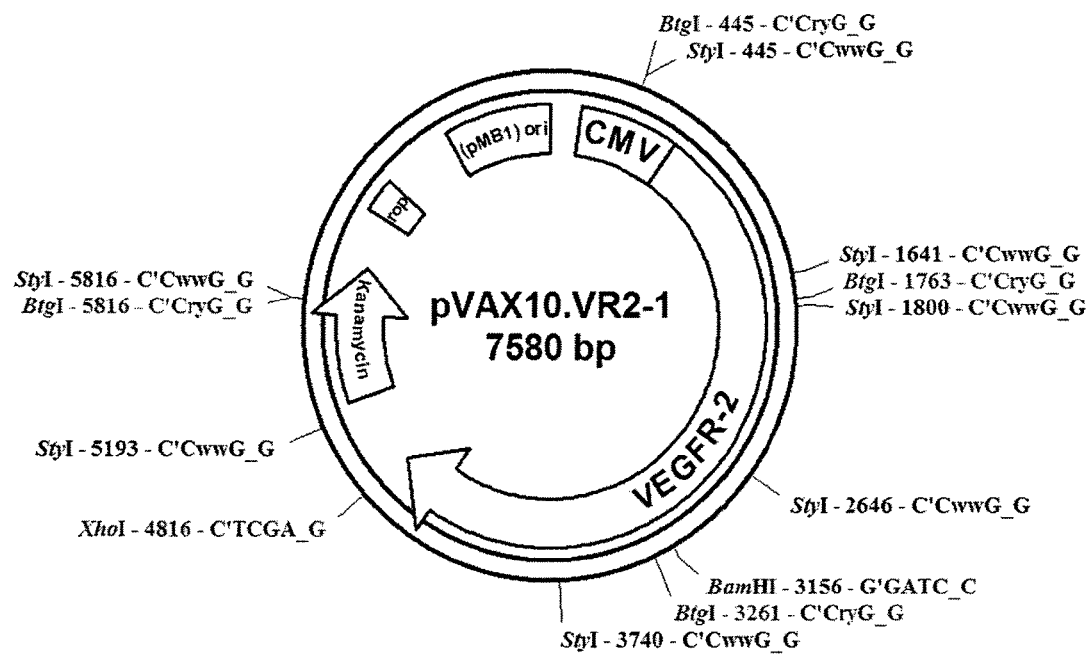

8 Claims, 34 Drawing Sheets
Specification includes a Sequence Listing.

Figure 1

```
              10         20         30         40         50         60
        MQSKVLLAVA LWLCVETRAA SVGLPSVSLD LPRLSIQKDI LTIKANTTLQ ITCRGQRDLD 70         80         90        100        110        120
        WLWPNNQSGS EQRVEVTECS DGLFCKTLTI PKVIGNDTGA YKCFYRETDL ASVIYVYVQD 130        140        150        160        170        180
        YRSPFIASVS DQHGVVYITE NKNKTVVIPC LGSISNLNVS LCARYPEKRF VPDGNRISWD 190        200        210        220        230        240
        SKKGFTIPSY MISYAGMVFC EAKINDESYQ SIMYIVVVVG YRIYDVVLSP SHGIELSVGE 250        260        270        280        290        300
        KLVLNCTART ELNVGIDFNW EYPSSKHQHK KLVNRDLKTQ SGSEMKKFLS TLTIDGVTRS 310        320        330        340        350        360
        DQGLYTCAAS SGLMTKKNST FVRVHEKPFV AFGSGMESLV EATVGERVRI PAKYLGYPPP 370        380        390        400        410        420
        EIKWYKNGIP LESNHTIKAG HVLTIMEVSE RDTGNYTVIL TNPISKEKQS HVVSLVVYVP 430        440        450        460        470        480
        PQIGEKSLIS PVDSYQYGTT QTLTCTVYAI PPPHHIHWYW QLEEECANEP SQAVSVTNPY 490        500        510        520        530        540
        PCEEWRSVED FQGGNKIEVN KNQFALIEGK NKTVSTLVIQ AANVSALYKC EAVNKVGRGE 550        560        570        580        590        600
        RVISFHVTRG PEITLQPDMQ PTEQESVSLW CTADRSTFEN LTWYKLGPQP LPIHVGELPT 610        620        630        640        650        660
        PVCKNLDTLW KLNATMFSNS TNDILIMELK NASLQDQGDY VCLAQDRKTK KRHCVVRQLT
```

Figure 1 (contd.)

```
         670        680        690        700        710        720
   VLERVAPTIT GNLENQTTSI GESIEVSCTA SGNPPPQIMW FKDNETLVED SGIVLKDGNR 730        740        750        760        770        780
   NLTIRRVRKE DEGLYTCQAC SVLGCAKVEA FFIIEGAQEK TNLEIIILVG TAVIAMFFWL 790        800        810        820        830        840
   LLVIILRTVK RANGGELKTG YLSIVMDPDE LPLDEHCERL PYDASKWEFP RDRLKLGKPL 850        860        870        880        890        900
   GRGAFGQVIE ADAFGIDKTA TCRTVAVKML KEGATHSEHR ALMSELKILI HIGHHLNVVN 910        920        930        940        950        960
   LLGACTKPGG PLMVIVEFCK FGNLSTYLRS KRNEFVPYKT KGARFRQGKD YVGAIPVDLK 970        980        990       1000       1010       1020
   RRLDSITSSQ SSASSGFVEE KSLSDVEEEE APEDLYKDFL TLEHLICYSF QVAKGMEFLA 1030       1040       1050       1060       1070       1080
   SRKCIHRDLA ARNILLSEKN VVKICDFGLA RDIYKDPDYV RKGDARLPLK WMAPETIFDR 1090       1100       1110       1120       1130       1140
   VYTIQSDVWS FGVLLWEIFS LGASPYPGVK IDEEFCRRLK EGTRMRAPDY TTPEMYQTML 1150       1160       1170       1180       1190       1200
   DCWHGEPSQR PTFSELVEHL GNLLQANAQQ DGKDYIVLPI SETLSMEEDS GLSLPTSPVS 1210       1220       1230       1240       1250       1260
   CMEEEEVCDP KFHYDNTAGI SQYLQNSKRK SRPVSVKTFE DIPLEEPEVK VIPDDNQTDS 1270       1280       1290       1300       1310       1320
   GMVLASEELK TLEDRTKLSP SFGGMVPSKS RESVASEGSN QTSGYQSGYH SDDTDTTVYS
```

Figure 1 (contd.)

```
         1330       1340       1350
SEEAELLKLI EIGVQTGSTA QILQPDSGTT LSSPPV
```

Figure 2

TGGGCTTTTGCTGGCCTTTTGCTCACATGTTCTTGACTCTTCGCGATGTACGGGCCA
GATATACGCGTTGACATTGATTATTGACTAGTTATTAATAGTAATCAATTACGGGGTC
ATTAGTTCATAGCCCATATATGGAGTTCCGCGTTACATAACTTACGGTAAATGGCCC
GCCTGGCTGACCGCCCAACGACCCCGCCCATTGACGTCAATAATGACGTATGTTC
CCATAGTAACGCCAATAGGGACTTTCCATTGACGTCAATGGGTGGACTATTTACGGT
AAACTGCCCACTTGGCAGTACATCAAGTGTATCATATGCCAAGTACGCCCCCTATTG
ACGTCAATGACGGTAAATGGCCCGCCTGGCATTATGCCCAGTACATGACCTTATGG
GACTTTCCTACTTGGCAGTACATCTACGTATTAGTCATCGCTATTACCATGGTGATG
CGGTTTTGGCAGTACATCAATGGGCGTGGATAGCGGTTTGACTCACGGGGATTTCC
AAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGT
GTACGGTGGGAGGTCTATATAAGCAGAGCTCTCTGGCTAACTAGAGAACCCACTGC
TTACTGGCTTATCGAAATTAATACGACTCACTATAGGGAGACCCAAGCTGGCTAGCC
TCGAGTCTAGAGGGCCCGTTTAAACCCGCTGATCAGCCTCGACTGTGCCTTCTAGT
TGCCAGCCATCTGTTGTTTGCCCCTCCCCGTGCCTTCCTTGACCCTGGAAGGTGC
CACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTG
GGAAGACAATAGCAGGCATGCTGGGGATGCGGTGGGCTCTATGGCTTCTACTGGG
CGGTTTTATGGACAGCAAGCGAACCGGAATTGCCAGCTGGGGCGCCCTCTGGTAA
GGTTGGGAAGCCCTGCAAAGTAAACTGGATGGCTTTCTCGCCGCCAAGGATCTGAT
GGCGCAGGGGATCAAGCTCTGATCAAGAGACAGGATGAGGATCGTTTCGCATGATT
GAACAAGATGGATTGCACGCAGGTTCTCCGGCCGCTTGGGTGGAGAGGCTATTCG
GCTATGACTGGGCACAACAGACAATCGGCTGCTCTGATGCCGCCGTGTTCCGGCT
GTCAGCGCAGGGGCGCCCGGTTCTTTTTGTCAAGACCGACCTGTCCGGTGCCCTG
AATGAACTGCAAGACGAGGCAGCGCGGCTATCGTGGCTGGCCACGACGGGCGTTC
CTTGCGCAGCTGTGCTCGACGTTGTCACTGAAGCGGGAAGGGACTGGCTGCTATT
GGGCGAAGTGCCGGGGCAGGATCTCCTGTCATCTCACCTTGCTCCTGCCGAGAAA
GTATCCATCATGGCTGATGCAATGCGGCGGCTGCATACGCTTGATCCGGCTACCTG
CCCATTCGACCACCAAGCGAAACATCGCATCGAGCGAGCACGTACTCGGATGGAA
GCCGGTCTTGTCGATCAGGATGATCTGGACGAAGAGCATCAGGGGCTCGCGCCAG
CCGAACTGTTCGCCAGGCTCAAGGCGAGCATGCCCGACGGCGAGGATCTCGTCGT
GACCCATGGCGATGCCTGCTTGCCGAATATCATGGTGGAAAATGGCCGCTTTTCTG
GATTCATCGACTGTGGCCGGCTGGGTGTGGCGGACCGCTATCAGGACATAGCGTT
GGCTACCCGTGATATTGCTGAAGAGCTTGGCGGCGAATGGGCTGACCGCTTCCTC
GTGCTTTACGGTATCGCCGCTCCCGATTCGCAGCGCATCGCCTTCTATCGCCTTCT
TGACGAGTTCTTCTGAATTATTAACGCTTACAATTTCCTGATGCGGTATTTTCTCCTT
ACGCATCTGTGCGGTATTTCACACCGCATACAGGTGGCACTTTTCGGGGAAATGTG
CGCGGAACCCCTATTTGTTTATTTTTCTAAATACATTCAAATATGTATCCGCTCATGA
GACAATAACCCTGATAAATGCTTCAATAATAGCACGTGCTAAAACTTCATTTTTAATT
TAAAAGGATCTAGGTGAAGATCCTTTTTGATAATCTCATGACCAAAATCCCTTAACGT
GAGTTTTCGTTCCACTGAGCGTCAGACCCCATCAGTGACCAAACAGGAAAAAACC
GCCCTTAACATGGCCCGCTTTATCAGAAGCCAGACATTAACGCTTCTGGAGAAACT
CAACGAGCTGGACGCGGATGAACAGGCAGACATCTGTGAATCGCTTCACGACCAC

Figure 2 (cont.)

GCTGATGAGCTTTACCGCAGCTGCCTCGCGCGTTTCGGTGATGACGGTGAAAACCT
CTGACACATGCAGCTCCCGGAGACGGTCACAGCTTGTCTGTAAGCGGATGCCGGG
AGCAGACAAGCCCGTCAGGGCGCGTCAGCGGGTGTTGGCGGGTGTCGGGGCGCA
GCCATGACCCAGTCACGTAGCGATAGCGGAGTGTATACTGGCTTAACTATGCGGCA
TCAGAGCAGATTGTACTGAGAGTGCACCATATGCGGTGTGAAATACCGCACAGATG
CGTAAGGAGAAAATACCGCATCAGGCGCTCTTCCGCTTCCTCGCTCACTGACTCGC
TGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGCTC
CGCCCCCTGACGAGCATCACAAAAATCGACGCTCAAGTCAGAGGTGGCGAAACC
CGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTC
GCTCCAAGCTGGGCTGTGTGCACGAACCCCCGTTCAGCCCGACCGCTGCGCCTT
ATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATCTG
CGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGC
AGAAAAAAAGGATCTCAAGAAGATCCTTTGATC

Figure 3

```
            10         20         30         40         50         60
MGSDVRDLNA LLPAVPSLGG GGGCALPVSG AAQWAPVLDF APPGASAYGS LGGPAPPPAP 70         80         90        100        110        120
PPPPPPPPHS FIKQEPSWGG AEPHEEQCLS AFTVHFSGQF TGTAGACRYG PFGPPPPSQA 130        140        150        160        170        180
SSGQARMFPN APYLPSCLES QPAIRNQGYS TVTFDGTPSY GHTPSHHAAQ FPNHSFKHED 190        200        210        220        230        240
PMGQQGSLGE QQYSVPPPVY GCHTPTDSCT GSQALLLRTP YSSDNLYQMT SQLECMTWNQ 250        260        270        280        290        300
MNLGATLKGV AAGSSSSVKW TEGQSNHSTG YESDNHTTPI LCGAQYRIHT HGVFRGIQDV 310        320        330        340        350        360
RRVPGVAPTL VRSASETSEK RPFMCAYPGC NKRYFKLSHL QMHSRKHTGE KPYQCDFKDC

370
ERRFSRSDQL K
```

Figure 4

MALPTARPLLGSCGTPALGSLLFLLFSLGWVQPSRTLAGETGQEAAPLDGVLANPPNISSLS
PRQLLGFPCAEVSGLSTERVRELAVALAQKNVKLSTEQLRCLAHRLSEPPEDLDALPLDLLL
FLNPDAFSGPQACTRFFSRITKANVDLLPRGAPERQRLLPAALACWGVRGSLLSEADVRAL
GGLACDLPGRFVAESAEVLLPRLVSCPGPLDQDQQEAARAALQGGGPPYGPPSTWSVST
MDALRGLLPVLGQPIIRSIPQGIVAAWRQRSSRDPSWRQPERTILRPRFRREVEKTACPSGK
KAREIDESLIFYKKWELEACVDAALLATQMDRVNAIPFTYEQLDVLKHKLDELYPQGYPESVI
QHLGYLFLKMSPEDIRKWNVTSLETLKALLEVNKGHEMSPQAPRRPLPQVATLIDRFVKGR
GQLDKDTLDTLTAFYPGYLCSLSPEELSSVPPSSIWAVRPQDLDTCDPRQLDVLYPKARLAF
QNMNGSEYFVKIQSFLGGAPTEDLKALSQQNVSMDLATFMKLRTDAVLPLTVAEVQKLLGP
HVEGLKAEERHRPVRDWILRQRQDDLDTLGLGLQGGIPNGYLVLDLSMQEALSGTPCLLGP
GPVLTVLALLLASTLA

Figure 5

MESPSAPPHRWCIPWQRLLLTASLLTFWNPPTTAKLTIESTPFNVAEGKEVLLLVHNLP
QHLFGYSWYKGERVDGNRQIIGYVIGTQQATPGPAYSGREIIYPNASLLIQNIIQNDTGFY
TLHVIKSDLVNEEATGQFRVYPELPKPSISSNNSKPVEDKDAVAFTCEPETQDATYLWW
VNNQSLPVSPRLQLSNGNRTLTLFNVTRNDTASYKCETQNPVSARRSDSVILNVLYGPD
APTISPLNTSYRSGENLNLSCHAASNPPAQYSWFVNGTFQQSTQELFIPNITVNNSGSY
TCQAHNSDTGLNRTTVTTITVYAEPPKPFITSNNSNPVEDEDAVALTCEPEIQNTTYLW
WVNNQSLPVSPRLQLSNDNRTLTLLSVTRNDVGPYECGIQNKLSVDHSDPVILNVLYGP
DDPTISPSYTYYRPGVNLSLSCHAASNPPAQYSWLIDGNIQQHTQELFISNITEKNSGLY
TCQANNSASGHSRTTVKTITVSAELPKPSISSNNSKPVEDKDAVAFTCEPEAQNTTYLW
WVNGQSLPVSPRLQLSNGNRTLTLFNVTRNDARAYVCGIQNSVSANRSDPVTLDVLYG
PDTPIISPPDSSYLSGANLNLSCHSASNPSPQYSWRINGIPQQHTQVLFIAKITPNNNGTY
ACFVSNLATGRNNSIVKSITVSASGTSPGLSAGATVGIMIGVLVGVALI

Figure 6

MESRGRRCPEMISVLGPISGHVLKAVFSRGDTPVLPHETRLLQTGIHVRVSQPSLILVSQ
YTPDSTPCHRGDNQLQVQHTYFTGSEVENVSVNVHNPTGRSICPSQEPMSIYVYALPL
KMLNIPSINVHHYPSAAERKHRHLPVADAVIHASGKQMWQARLTVSGLAWTRQQNQW
KEPDVYYTSAFVFPTKDVALRHVVCAHELVCSMENTRATKMQVIGDQYVKVYLESFCE
DVPSGKLFMHVTLGSDVEEDLTMTRNPQPFMRPHERNGFTVLCPKNMIIKPGKISHIML
DVAFTSHEHFGLLCPKSIPGLSISGNLLMNGQQIFLEVQAIRETVELRQYDPVAALFFFDI
DLLLQRGPQYSEHPTFTSQYRIQGKLEYRHTWDRHDEGAAQGDDDVWTSGSDSDEEL
VTTERKTPRVTGGGAMAGASTSAGRKRKSASSATACTAGVMTRGRLKAESTVAPEED
TDEDSDNEIHNPAVFTWPPWQAGILARNLVPMVATVQGQNLKYQEFFWDANDIYRIFA
ELEGVWQPAAQPKRRRHRQDALPGPCIASTPKKHRG

Figure 7

MESRGRRCPEMISVLGPISGHVLKAVFSRGDTPVLPHETRLLQTGIHVRVSQPSLILVSQ
YTPDSTPCHRGDNQLQVQHTYFTGSEVENVSVNVHNPTGRSICPSQEPMSIYVYALPL
KMLNIPSINVHHYPSAAERKHRHLPVADAVIHASGKQMWQARLTVSGLAWTRQQNQW
KEPDVYYTSAFVFPTKDVALRHVVCAHELVCSMENTRATKMQVIGDQYVKVYLESFCE
DVPSGKLFMHVTLGSDVEEDLTMTRNPQPFMRPHERNGFTVLCPKNMIIKPGKISHIML
DVAFTSHEHFGLLCPKSIPGLSISGNLLMNGQQIFLEVQAIRETVELRQYDPVAALFFFDI
DLLLQRGPQYSEHPTFTSQYRIQGKLEYRHTWDRHDEGAAQGDDDVWTSGSDSDEEL
VTTERKTPRVTGGGAMAGASTSAGRNRKSASSATACTAGVMTRGRLKAESTVAPEED
TDEDSDNEIHNPAVFTWPPWQAGILARNLVPMVATVQGQNLKYQEFFWDANDIYRIFA
ELEGVWQPAAQPKRRRHRQDALPGPCIASTPKKHRG

Figure 8

MESRGRRCPEMISVLGPISGHVLKAVFSRGDTPVLPHETRLLQTGIHVRVSQPSLILVSQ
YTPDSTPCHRGDNQLQVQHTYFTGSEVENVSVNVHNPTGRSICPSQEPMSIYVYALPL
KMLNIPSINVHHYPSAAERKHRHLPVADAVIHASGKQMWQARLTVSGLAWTRQQNQW
KEPDVYYTSAFVFPTKDVALRHVVCAHELVCSMENTRATKMQVIGDQYVKVYLESFCE
DVPSGKLFMHVTLGSDVEEDLTMTRNPQPFMRPHERNGFTVLCPKNMIIKPGKISHIML
DVAFTSHEHFGLLCPKSIPGLSISGNLLMNGQQIFLEVQAIRETVELRQYDPVAALFFFDI
DLLLQRGPQYSEHPTFTSQYRIQGKLEYRHTWDRHDEGAAQGDDDVWTSGSDSDEEL
VTTERKTPRVTGGGAMAGASTSAGRNRKSASSATACTAGVMTRGRLKAESTVAPEED
TDEDSDNEIHNPAVFTWPPWQAGILARNLVPMVATVQGQNLKYQEFFWDANDIYRIFA
ELEGVWQPAAQ

Figure 9 atgcagagcaaggtgctgctggccgtcgccctgtggctctgcgtggagacccgggccgcctctgtgggtttgcctagtgtttct
cttgatctgcccaggctcagcatacaaaaagacatacttacaattaaggctaatacaactcttcaaattacttgcaggggac
agagggacttggactggctttggcccaataatcagagtggcagtgagcaaagggtggaggtgactgagtgcagcgatgg
cctcttctgtaagacactcacaattccaaaagtgatcggaaatgacactggagcctacaagtgcttctaccgggaaactgac
ttggcctcggtcatttatgtctatgttcaagattacagatctccatttattgcttctgttagtgaccaacatggagtcgtgtacattact
gagaacaaaaacaaaactgtggtgattccatgtctcgggtccatttcaaatctcaacgtgtcactttgtgcaagatacccaga
aaagagatttgttcctgatggtaacagaatttcctgggacagcaagaagggctttactattcccagctacatgatcagctatgc
tggcatggtcttctgtgaagcaaaaattaatgatgaaagttaccagtctattatgtacatagttgtcgttgtagggtataggattta
tgatgtggttctgagtccgtctcatggaattgaactatctgttggagaaaagcttgtcttaaattgtacagcaagaactgaacta
aatgtggggattgacttcaactgggaataccttcttcgaagcatcagcataagaaacttgtaaaccgagacctaaaaacc
cagtctgggagtgagatgaagaaattttgagcaccttaactatagatggtgtaacccggagtgaccaaggattgtacacct
gtgcagcatccagtgggctgatgaccaagaagaacagcacatttgtcagggtccatgaaaaaccttttgttgcttttggaagt
ggcatggaatctctggtggaagccacggtgggggagcgtgtcagaatccctgcgaagtaccttggttacccaccccccaga
aataaaatggtataaaaatggaataccccttgagtccaatcacacaattaaagcggggcatgtactgacgattatggaagt
gagtgaaagagacacaggaaattacactgtcatccttaccaatcccatttcaaaggagaagcagagccatgtggtctctct
ggttgtgtatgtcccaccccagattggtgagaaatctctaatctctcctgtggattcctaccagtacggcaccactcaaacgct
gacatgtacggtctatgccattcctcccccgcatcacatccactggtattggcagttggaggaagagtgcgccaacgagccc
agccaagctgtctcagtgacaaacccatacccttgtgaagaatggagaagtgtggaggacttccagggaggaaataaaa
ttgaagttaataaaaatcaatttgctctaattgaaggaaaaaacaaaactgtaagtacccttgttatccaagcggcaaatgtgt
cagctttgtacaaatgtgaagcggtcaacaaagtcgggagaggagagagggtgatctccttccacgtgaccaggggtcct
gaaattactttgcaacctgacatgcagcccactgagcaggagagcgtgtctttgtggtgcactgcagacagatctacgtttga
gaacctcacatggtacaagcttggcccacagcctctgccaatccatgtgggagagttgcccacacctgtttgcaagaacttg
gatactctttggaaattgaatgccaccatgttctctaatagcacaaatgacattttgatcatggagcttaagaatgcatccttgca
ggaccaaggagactatgtctgccttgctcaagacaggaagaccaagaaaagacattgcgtggtcaggcagctcacagtc
ctagagcgtgtggcacccacgatcacaggaaacctggagaatcagacgacaagtattggggaaagcatcgaagtctcat
gcacggcatctgggaatcccccctccacagatcatgtggtttaaagataatgagacccttgtagaagactcaggcattgtattg
aaggatgggaaccggaacctcactatccgcagagtgaggaaggaggacgaaggcctctacacctgccaggcatgcag
tgttcttggctgtgcaaaagtggaggcattttcataatagaaggtgcccaggaaaagacgaacttggaaatcattattctagt
aggcacggcggtgattgccatgttcttctggctacttcttgtcatcatcctacggaccgttaagcgggccaatggaggggaact
gaagacaggctacttgtccatcgtcatggatccagatgaactcccattggatgaacattgtgaacgactgccttatgatgcca
gcaaatgggaattccccagagaccggctgaagctaggtaagcctcttggccgtggtgcctttggccaagtgattgaagcag
atgcctttggaattgacaagacagcaacttgcaggacagtagcagtcaaaatgttgaaagaaggagcaacacacagtga
gcatcgagctctcatgtctgaactcaagatcctcattcatattggtcaccatctcaatgtggtcaaccttctaggtgcctgtacca
agccaggagggccactcatggtgattgtggaattctgcaaatttggaaacctgtccacttacctgaggagcaagagaaatg
aatttgtccctacaagaccaaaggggcacgattccgtcaagggaaagactacgttggagcaatccctgtggatctgaaa
cggcgcttggacagcatcaccagtagccagagctcagccagctctggatttgtggaggagaagtccctcagtgatgtaga
agaagaggaagctcctgaagatctgtataaggacttcctgaccttggagcatctcatctgttacagcttccaagtggctaagg
gcatggagttcttggcatcgcgaaagtgtatccacagggacctggcggcacgaaatatcctcttatcggagaagaacgtgg
ttaaaatctgtgactttggcttggcccgggatatttataaagatccagattatgtcagaaaaggagatgctcgcctcccttttgaa
atggatggccccagaaacaatttttgacagagtgtacacaatccagagtgacgtctggtcttttggtgttttgctgtgggaaata
ttttccttaggtgcttctccatatcctggggtaaagattgatgaagaattttgtaggcgattgaaagaaggaactagaatgagg
gccccctgattatactacaccagaaatgtaccagaccatgctggactgctggcacggggagcccagtcagagacccacgtt
ttcagagttggtggaacatttgggaaatctcttcaagctaatgctcagcaggatggcaaagactacattgttcttccgatatca
gagactttgagcatggaagaggattctggactctctctgcctacctcacctgtttcctgtatggaggaggaggaagtatgtgac
cccaaattccattatgacaacacagcaggaatcagtcagtatctgcagaacagtaagcgaaagagccggcctgtgagtgt
aaaaacatttgaagatatcccgttagaagaaccagaagtaaaagtaatcccagatgacaaccagacggacagtggtatg
gttcttgcctcagaagagctgaaaactttggaagacagaaccaaattatctccatcttttggtggaatggtgcccagcaaaag
cagggagtctgtggcatctgaaggctcaaaccagacaagcggctaccagtccggatatcactccgatgacacagacacc
accgtgtactccagtgaggaagcagaacttttaaagctgatagagattggagtgcaaaccggtagcacagcccagattctc
cagcctgactcggggaccacactgagctctcctcctgtttaa

Figure 10

ATGGACTTCCTCTTGCTGCAGGACCCGGCTTCCACGTGTGTCCCGGAGCCGGCGTCTC
AGCACACGCTCCGCTCCGGGCCTGGGTGCCTACAGCAGCCAGAGCAGCAGGGAGTCC
GGGACCCGGGCGGCATCTGGGCCAAGTTAGGCGCCGCCGAGGCCAGCGCTGAACGT
CTCCAGGGCCGGAGGAGCCGCGGGGCGTCCGGGTCTGAGCCGCAGCAAATGGGCTC
CGACGTGCGGGACCTGAACGCGCTGCTGCCCGCCGTCCCCTCCCTGGGTGGCGGCG
GCGGCTGTGCCCTGCCTGTGAGCGGCGCGGCGCAGTGGGCGCCGGTGCTGGACTTTG
CGCCCCGGGCGCTTCGGCTTACGGGTCGTTGGGCGGCCCCGCGCCGCCACCGGCT
CCGCCGCCACCCCCGCCGCCGCCGCCTCACTCCTTCATCAAACAGGAGCCGAGCTGG
GGCGGCGCGGAGCCGCACGAGGAGCAGTGCCTGAGCGCCTTCACTGTCCACTTTTCC
GGCCAGTTCACTGGCACAGCCGGAGCCTGTCGCTACGGGCCCTTCGGTCCTCCTCCG
CCCAGCCAGGCGTCATCCGGCCAGGCCAGGATGTTTCCTAACGCGCCCTACCTGCCCA
GCTGCCTGGAGAGCCAGCCCGCTATTCGCAATCAGGGTTACAGCACGGTCACCTTCGA
CGGGACGCCCAGCTACGGTCACACGCCCTCGCACCATGCGGCGCAGTTCCCCAACCA
CTCATTCAAGCATGAGGATCCCATGGGCCAGCAGGGCTCGCTGGGTGAGCAGCAGTAC
TCGGTGCCGCCCCGGTCTATGGCTGCCACACCCCACCGACAGCTGCACCGGCAGC
CAGGCTTTGCTGCTGAGGACGCCCTACAGCAGTGACAATTTATACCAAATGACATCCCA
GCTTGAATGCATGACCTGGAATCAGATGAACTTAGGAGCCACCTTAAAGGGAGTTGCTG
CTGGGAGCTCCAGCTCAGTGAAATGGACAGAAGGGCAGAGCAACCACAGCACAGGGTA
CGAGAGCGATAACCACACAACGCCCATCCTCTGCGGAGCCCAATACAGAATACACACG
CACGGTGTCTTCAGAGGCATTCAGTGA

Figure 11

ATGGCCTTGCCAACGGCTCGACCCCTGTTGGGGTCCTGTGGGACCCCCGCCCTCGGC
AGCCTCCTGTTCCTGCTCTTCAGCCTCGGATGGGTGCAGCCCTCCAGGACCCTGGCTG
GAGAGACAGGGCAGGAGGCTGCGCCCCTGGACGGAGTCCTGGCCAACCCACCTAACA
TTTCCAGCCTCTCCCCTCGCCAACTCCTTGGCTTCCCGTGTGCGGAGGTGTCCGGCCT
GAGCACGGAGCGTGTCCGGGAGCTGGCTGTGGCCTTGGCACAGAAGAATGTCAAGCT
CTCAACAGAGCAGCTGCGCTGTCTGGCTCACCGGCTCTCTGAGCCCCCGAGGACCTG
GACGCCCTCCCATTGGACCTGCTGCTATTCCTCAACCCAGATGCGTTCTCGGGGCCCC
AGGCCTGCACCCGTTTCTTCTCCCGCATCACGAAGGCCAATGTGGACCTGCTCCCGAG
GGGGGCTCCCGAGCGACAGCGGCTGCTGCCTGCGGCTCTGGCCTGCTGGGGTGTGC
GGGGGTCTCTGCTGAGCGAGGCTGATGTGCGGGCTCTGGGAGGCCTGGCTTGCGACC
TGCCTGGGCGCTTTGTGGCCGAGTCGGCCGAAGTGCTGCTACCCCGGCTGGTGAGCT
GCCCGGGACCCCTGGACCAGGACCAACAGGAGGCAGCCAGGGCGGCTCTGCAGGGC
GGGGGACCCCCCTACGGCCCCCGTCGACATGGTCTGTCTCCACGATGGACGCTCTG
CGGGGCCTGCTGCCCGTGCTGGGCCAGCCCATCATCCGCAGCATCCCGCAGGGCATC
GTGGCCGCGTGGCGGCAACGCTCCTCGGGACCCATCCTGGCGGCAGCCTGAACGG
ACCATCCTCCGGCCGCGGTTCCGGCGGGAAGTGGAGAAGACAGCCTGTCCTTCAGGC
AAGAAGGCCCGCGAGATAGACGAGAGCCTCATCTTCTACAAGAAGTGGGAGCTGGAAG
CCTGCGTGGATGCGGCCCTGCTGGCCACCCAGATGGACCGCGTGAACGCCATCCCCT
TCACCTACGAGCAGCTGGACGTCCTAAAGCATAAACTGGATGAGCTCTACCCACAAGGT
TACCCCGAGTCTGTGATCCAGCACCTGGGCTACCTCTTCCTCAAGATGAGCCCTGAGG
ACATTCGCAAGTGGAATGTGACGTCCCTGGAGACCCTGAAGGCTTTGCTTGAAGTCAAC
AAAGGGCACGAAATGAGTCCTCAGGCTCCTCGGCGGCCCCTCCCACAGGTGGCCACC
CTGATCGACCGCTTTGTGAAGGGAAGGGGCCAGCTAGACAAAGACACCCTAGACACCC
TGACCGCCTTCTACCCTGGGTACCTGTGCTCCCTCAGCCCCGAGGAGCTGAGCTCCGT
GCCCCCCAGCAGCATCTGGGCGGTCAGGCCCCAGGACCTGGACACGTGTGACCCAAG
GCAGCTGGACGTCCTCTATCCCAAGGCCCGCCTTGCTTTCCAGAACATGAACGGGTCC
GAATACTTCGTGAAGATCCAGTCCTTCCTGGGTGGGGCCCCACGGAGGATTTGAAGG
CGCTCAGTCAGCAGAATGTGAGCATGGACTTGGCCACGTTCATGAAGCTGCGGACGGA
TGCGGTGCTGCCGTTGACTGTGGCTGAGGTGCAGAAACTTCTGGGACCCCACGTGGAG
GGCCTGAAGGCGGAGGAGCGGCACCGCCCGGTGCGGGACTGGATCCTACGGCAGCG
GCAGGACGACCTGGACACGCTGGGGCTGGGGCTACAGGGCGGCATCCCCAACGGCTA
CCTGGTCCTAGACCTCAGCATGCAAGAGGCCCTCTCGGGGACGCCCTGCCTCCTAGGA
CCTGGACCTGTTCTCACCGTCCTGGCACTGCTCCTAGCCTCCACCCTGGCCTGA

Figure 12

ATGGAGTCTCCCTCGGCCCCTCCCCACAGATGGTGCATCCCCTGGCAGAGGCTCC
TGCTCACAGCCTCACTTCTAACCTTCTGGAACCCGCCCACCACTGCCAAGCTCACT
ATTGAATCCACGCCGTTCAATGTCGCAGAGGGGAAGGAGGTGCTTCTACTTGTCCA
CAATCTGCCCCAGCATCTTTTTGGCTACAGCTGGTACAAAGGTGAAAGAGTGGATG
GCAACCGTCAAATTATAGGATATGTAATAGGAACTCAACAAGCTACCCCAGGGCCC
GCATACAGTGGTCGAGAGATAATATACCCCAATGCATCCCTGCTGATCCAGAACAT
CATCCAGAATGACACAGGATTCTACACCCTACACGTCATAAAGTCAGATCTTGTGAA
TGAAGAAGCAACTGGCCAGTTCCGGGTATACCCGGAGCTGCCCAAGCCCTCCATCT
CCAGCAACAACTCCAAACCCGTGGAGGACAAGGATGCTGTGGCCTTCACCTGTGAA
CCTGAGACTCAGGACGCAACCTACCTGTGGTGGGTAAACAATCAGAGCCTCCCGGT
CAGTCCCAGGCTGCAGCTGTCCAATGGCAACAGGACCCTCACTCTATTCAATGTCA
CAAGAAATGACACAGCAAGCTACAAATGTGAAACCCAGAACCCAGTGAGTGCCAGG
CGCAGTGATTCAGTCATCCTGAATGTCCTCTATGGCCCGGATGCCCCCACCATTTC
CCCTCTAAACACATCTTACAGATCAGGGGAAAATCTGAACCTCTCCTGCCACGCAG
CCTCTAACCCACCTGCACAGTACTCTTGGTTTGTCAATGGGACTTTCCAGCAATCCA
CCCAAGAGCTCTTTATCCCCAACATCACTGTGAATAATAGTGGATCCTATACGTGCC
AAGCCCATAACTCAGACACTGGCCTCAATAGGACCACAGTCACGACGATCACAGTC
TATGCAGAGCCACCCAAACCCTTCATCACCAGCAACAACTCCAACCCCGTGGAGGA
TGAGGATGCTGTAGCCTTAACCTGTGAACCTGAGATTCAGAACACAACCTACCTGT
GGTGGGTAAATAATCAGAGCCTCCCGGTCAGTCCCAGGCTGCAGCTGTCCAATGAC
AACAGGACCCTCACTCTACTCAGTGTCACAAGGAATGATGTAGGACCCTATGAGTG
TGGAATCCAGAACAAATTAAGTGTTGACCACAGCGACCCAGTCATCCTGAATGTCCT
CTATGGCCCAGACGACCCCACCATTTCCCCCTCATACACCTATTACCGTCCAGGGG
TGAACCTCAGCCTCTCCTGCCATGCAGCCTCTAACCCACCTGCACAGTATTCTTGG
CTGATTGATGGGAACATCCAGCAACACACACAAGAGCTCTTTATCTCCAACATCACT
GAGAAGAACAGCGGACTCTATACCTGCCAGGCCAATAACTCAGCCAGTGGCCACA
GCAGGACTACAGTCAAGACAATCACAGTCTCTGCGGAGCTGCCCAAGCCCTCCATC
TCCAGCAACAACTCCAAACCCGTGGAGGACAAGGATGCTGTGGCCTTCACCTGTGA
ACCTGAGGCTCAGAACACAACCTACCTGTGGTGGGTAAATGGTCAGAGCCTCCCAG
TCAGTCCCAGGCTGCAGCTGTCCAATGGCAACAGGACCCTCACTCTATTCAATGTC
ACAAGAAATGACGCAAGAGCCTATGTATGTGGAATCCAGAACTCAGTGAGTGCAAA
CCGCAGTGACCCAGTCACCCTGGATGTCCTCTATGGCCGGACACCCCATCATTT
CCCCCCCAGACTCGTCTTACCTTTCGGGAGCGAACCTCAACCTCTCCTGCCACTCG
GCCTCTAACCCATCCCCGCAGTATTCTTGGCGTATCAATGGGATACCGCAGCAACA
CACACAAGTTCTCTTTATCGCCAAAATCACGCCAAATAATAACGGGACCTATGCCTG
TTTTGTCTCTAACTTGGCTACTGGCCGCAATAATTCCATAGTCAAGAGCATCACAGT
CTCTGCATCTGGAACTTCTCCTGGTCTCTCAGCTGGGGCCACTGTCGGCATCATGA
TTGGAGTGCTGGTTGGGGTTGCTCTGATATAG

Figure 13

ATGGAATCCAGGGGGAGGAGGTGTCCGGAGATGATCTCAGTCCTCGGACCGATTA
GCGGTCACGTGCTCAAAGCGGTCTTCAGCAGAGGAGACACTCCGGTGCTGCCGCA
CGAAACAAGGCTCCTTCAGACGGGGATACACGTGCGTGTGAGTCAGCCCAGCCTG
ATCCTCGTGTCTCAATACACCCCTGACAGCACTCCCTGTCACAGAGGGGACAACCA
ACTCCAGGTCCAGCACACCTACTTCACTGGGAGCGAGGTCGAGAACGTCAGCGTG
AACGTGCACAACCCCACGGGAAGATCAATCTGCCCTAGCCAGGAGCCCATGAGCA
TCTACGTGTACGCCCTCCCGCTCAAGATGCTCAACATCCCCTCCATCAACGTCCAC
CACTATCCCTCCGCTGCCGAACGTAAACACCGACACTTGCCAGTTGCGGACGCCGT
GATACACGCTTCAGGGAAGCAGATGTGGCAAGCCAGGCTTACTGTGAGTGGACTC
GCCTGGACTAGGCAACAGAACCAGTGGAAGGAGCCCGACGTGTACTACACCAGCG
CCTTCGTGTTCCCCACAAAAGACGTCGCGCTGCGACATGTGGTGTGCGCTCACGAA
CTGGTGTGCAGCATGGAGAACACGCGAGCGACCAAGATGCAGGTGATCGGTGACC
AGTACGTCAAGGTGTACCTGGAGAGCTTCTGCGAGGATGTCCCGTCCGGAAAGCT
GTTCATGCACGTGACCCTGGGCAGTGACGTTGAGGAAGACCTGACCATGACGCGT
AACCCGCAGCCTTTCATGAGACCGCACGAGAGGAACGGATTCACCGTCCTGTGCC
CGAAGAACATGATCATCAAGCCCGGCAAGATCAGCCACATCATGCTCGACGTCGCC
TTCACCTCTCACGAACACTTCGGGCTGCTGTGTCCGAAGAGCATTCCGGGTCTGAG
CATCTCAGGCAACCTGCTGATGAACGGGCAGCAGATCTTCCTGGAAGTGCAGGCC
ATAAGGGAGACCGTGGAACTGAGGCAGTACGATCCTGTGGCTGCCCTGTTCTTCTT
CGACATCGACCTCTTGCTGCAAAGGGGTCCACAGTATAGCGAACACCCCACCTTCA
CCTCCCAGTACCGTATCCAGGGCAAGCTGGAGTACCGACACACTTGGGATAGGCA
CGACGAGGGTGCCGCTCAAGGTGACGACGATGTTTGGACTAGCGGCTCTGATAGC
GACGAAGAGCTGGTGACCACTGAGCGCAAAACTCCAAGAGTTACGGGCGGCGGCG
CAATGGCTGGCGCCTCTACTTCCGCGGGAAGGAAaAGGAAAAGCGCGTCTAGCGC
AACTGCATGCACTGCCGGTGTGATGACAAGGGGGAGACTGAAGGCCGAGAGTACA
GTGGCTCCGGAAGAGGATACCGACGAGGACTCTGACAACGAGATCCACAACCCCG
CAGTGTTTACGTGGCCACCTTGGCAAGCCGGCATCCTTGCTAGAAACCTGGTGCCC
ATGGTGGCCACAGTCCAAGGCCAGAACCTGAAGTACCAGGAGTTCTTCTGGGACG
CCAACGACATCTACCGTATCTTCGCCGAACTTGAAGGCGTCTGGCAGCCGGCGGC
TCAACCCAAAAGGAGACGTCACAGACAGGACGCGCTTCCCGGACCCTGTATTGCCT
CTACCCCCAAGAAACACCGGGGC

Figure 14

ATGGAATCCAGGGGGAGGAGGTGTCCGGAGATGATCTCAGTCCTCGGACCGATTA
GCGGTCACGTGCTCAAAGCGGTCTTCAGCAGAGGAGACACTCCGGTGCTGCCGCA
CGAAACAAGGCTCCTTCAGACGGGGATACACGTGCGTGTGAGTCAGCCCAGCCTG
ATCCTCGTGTCTCAATACACCCCTGACAGCACTCCCTGTCACAGAGGGGACAACCA
ACTCCAGGTCCAGCACACCTACTTCACTGGGAGCGAGGTCGAGAACGTCAGCGTG
AACGTGCACAACCCCACGGGAAGATCAATCTGCCCTAGCCAGGAGCCCATGAGCA
TCTACGTGTACGCCCTCCCGCTCAAGATGCTCAACATCCCCTCCATCAACGTCCAC
CACTATCCCTCCGCTGCCGAACGTAAACACCGACACTTGCCAGTTGCGGACGCCGT
GATACACGCTTCAGGGAAGCAGATGTGGCAAGCCAGGCTTACTGTGAGTGGACTC
GCCTGGACTAGGCAACAGAACCAGTGGAAGGAGCCCGACGTGTACTACACCAGCG
CCTTCGTGTTCCCCACAAAAGACGTCGCGCTGCGACATGTGGTGTGCGCTCACGAA
CTGGTGTGCAGCATGGAGAACACGCGAGCGACCAAGATGCAGGTGATCGGTGACC
AGTACGTCAAGGTGTACCTGGAGAGCTTCTGCGAGGATGTCCCGTCCGGAAAGCT
GTTCATGCACGTGACCCTGGGCAGTGACGTTGAGGAAGACCTGACCATGACGCGT
AACCCGCAGCCTTTCATGAGACCGCACGAGAGGAACGGATTCACCGTCCTGTGCC
CGAAGAACATGATCATCAAGCCCGGCAAGATCAGCCACATCATGCTCGACGTCGCC
TTCACCTCTCACGAACACTTCGGGCTGCTGTGTCCGAAGAGCATTCCGGGTCTGAG
CATCTCAGGCAACCTGCTGATGAACGGGCAGCAGATCTTCCTGGAAGTGCAGGCC
ATAAGGGAGACCGTGGAACTGAGGCAGTACGATCCTGTGGCTGCCCTGTTCTTCTT
CGACATCGACCTCTTGCTGCAAAGGGGTCCACAGTATAGCGAACACCCCACCTTCA
CCTCCCAGTACCGTATCCAGGGCAAGCTGGAGTACCGACACACTTGGGATAGGCA
CGACGAGGGTGCCGCTCAAGGTGACGACGATGTTTGGACTAGCGGCTCTGATAGC
GACGAAGAGCTGGTGACCACTGAGCGCAAAACTCCAAGAGTTACGGGCGGCGGCG
CAATGGCTGGCGCCTCTACTTCCGCGGGAAGGAAcAGGAAAAGCGCGTCTAGCGC
AACTGCATGCACTGCCGGTGTGATGACAAGGGGGAGACTGAAGGCCGAGAGTACA
GTGGCTCCGGAAGAGGATACCGACGAGGACTCTGACAACGAGATCCACAACCCCG
CAGTGTTTACGTGGCCACCTTGGCAAGCCGGCATCCTTGCTAGAAACCTGGTGCCC
ATGGTGGCCACAGTCCAAGGCCAGAACCTGAAGTACCAGGAGTTCTTCTGGGACG
CCAACGACATCTACCGTATCTTCGCCGAACTTGAAGGCGTCTGGCAGCCGGCGGC
TCAACCCAAAAGGAGACGTCACAGACAGGACGCGCTTCCCGGACCCTGTATTGCCT
CTACCCCCAAGAAACACCGGGGC

Figure 15

ATGGAATCCAGGGGGAGGAGGTGTCCGGAGATGATCTCAGTCCTCGGACCGATTA
GCGGTCACGTGCTCAAAGCGGTCTTCAGCAGAGGAGACACTCCGGTGCTGCCGCA
CGAAACAAGGCTCCTTCAGACGGGGATACACGTGCGTGTGAGTCAGCCCAGCCTG
ATCCTCGTGTCTCAATACACCCCTGACAGCACTCCCTGTCACAGAGGGGACAACCA
ACTCCAGGTCCAGCACACCTACTTCACTGGGAGCGAGGTCGAGAACGTCAGCGTG
AACGTGCACAACCCCACGGGAAGATCAATCTGCCCTAGCCAGGAGCCCATGAGCA
TCTACGTGTACGCCCTCCCGCTCAAGATGCTCAACATCCCTCCATCAACGTCCAC
CACTATCCCTCCGCTGCCGAACGTAAACACCGACACTTGCCAGTTGCGGACGCCGT
GATACACGCTTCAGGGAAGCAGATGTGGCAAGCCAGGCTTACTGTGAGTGGACTC
GCCTGGACTAGGCAACAGAACCAGTGGAAGGAGCCCGACGTGTACTACACCAGCG
CCTTCGTGTTCCCCACAAAAGACGTCGCGCTGCGACATGTGGTGTGCGCTCACGAA
CTGGTGTGCAGCATGGAGAACACGCGAGCGACCAAGATGCAGGTGATCGGTGACC
AGTACGTCAAGGTGTACCTGGAGAGCTTCTGCGAGGATGTCCCGTCCGGAAAGCT
GTTCATGCACGTGACCCTGGGCAGTGACGTTGAGGAAGACCTGACCATGACGCGT
AACCCGCAGCCTTTCATGAGACCGCACGAGAGGAACGGATTCACCGTCCTGTGCC
CGAAGAACATGATCATCAAGCCCGGCAAGATCAGCCACATCATGCTCGACGTCGCC
TTCACCTCTCACGAACACTTCGGGCTGCTGTGTCCGAAGAGCATTCCGGGTCTGAG
CATCTCAGGCAACCTGCTGATGAACGGGCAGCAGATCTTCCTGGAAGTGCAGGCC
ATAAGGGAGACCGTGGAACTGAGGCAGTACGATCCTGTGGCTGCCCTGTTCTTCTT
CGACATCGACCTCTTGCTGCAAAGGGGTCCACAGTATAGCGAACACCCCACCTTCA
CCTCCCAGTACCGTATCCAGGGCAAGCTGGAGTACCGACACACTTGGGATAGGCA
CGACGAGGGTGCCGCTCAAGGTGACGACGATGTTTGGACTAGCGGCTCTGATAGC
GACGAAGAGCTGGTGACCACTGAGCGCAAAACTCCAAGAGTTACGGGCGGCGGCG
CAATGGCTGGCGCCTCTACTTCCGCGGGAAGGAAcAGGAAAAGCGCGTCTAGCGC
AACTGCATGCACTGCCGGTGTGATGACAAGGGGGAGACTGAAGGCCGAGAGTACA
GTGGCTCCGGAAGAGGATACCGACGAGGACTCTGACAACGAGATCCACAACCCCG
CAGTGTTTACGTGGCCACCTTGGCAAGCCGGCATCCTTGCTAGAAACCTGGTGCCC
ATGGTGGCCACAGTCCAAGGCCAGAACCTGAAGTACCAGGAGTTCTTCTGGGACG
CCAACGACATCTACCGTATCTTCGCCGAACTTGAAGGCGTCTGGCAGCCGGCGGC
TCAA

Figure 31
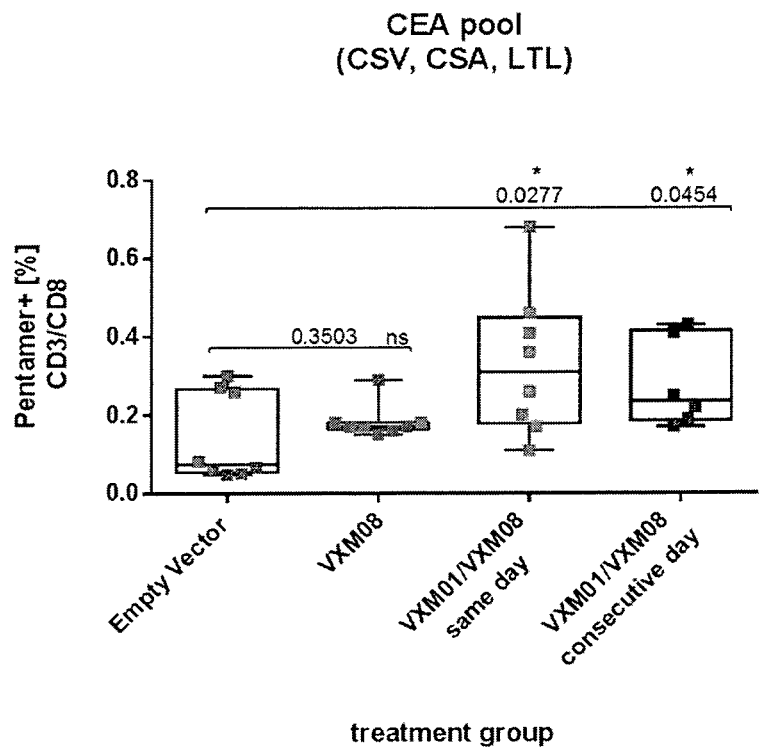
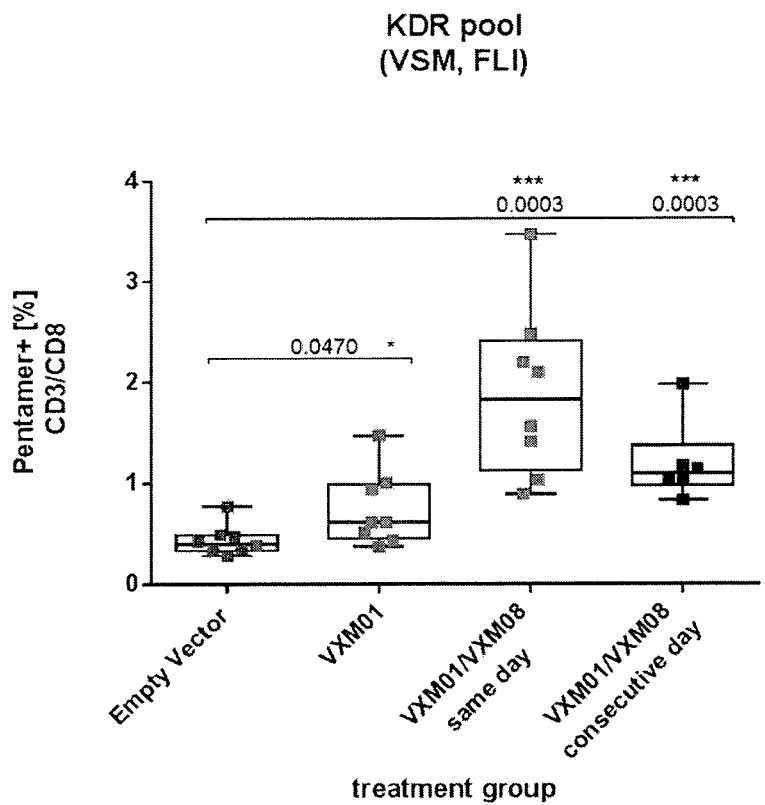

VEGFR-2 TARGETING DNA VACCINE FOR COMBINATION THERAPY

CROSS-REFERENCE TO RELATED APPLICATIONS

This application is a 371 National Stage application of International Application No. PCT/EP2016/001004, filed Jun. 16, 2016, which claims the benefit of application Ser. No. 15001803.4 EP, filed Jun. 18, 2015, and is herein incorporated by reference in its entirety.

INCORPORATION OF SEQUENCE LISTING BY REFERENCE

The sequence listing contained in the file named "WRST004US-revised_ST25.txt", which is 67,042 kilobytes (size as measured in Microsoft Windows®) and was created on Aug. 24, 2020, is filed herewith by electronic submission and is incorporated by reference herein.

FIELD OF THE INVENTION

The present invention relates to an attenuated strain of Salmonella comprising at least one copy of a DNA molecule comprising an expression cassette encoding a VEGF receptor protein, for use in the treatment of cancer, wherein the treatment further comprises the administration of at least one further anti-cancer agent. The present invention further relates to a pharmaceutical composition comprising an attenuated strain of Salmonella comprising at least one copy of a DNA molecule comprising an expression cassette encoding a VEGF receptor protein, wherein the pharmaceutical composition further comprises at least one further attenuated strain of Salmonella comprising at least one copy of a further DNA molecule comprising a further expression cassette encoding a tumor antigen or a tumor stroma antigen.

BACKGROUND OF THE INVENTION

The finding that tumors can be immunogenic has led to the development of a number of cancer immunotherapies designed to employ the immune system to selectively eliminate malignant cells while sparing normal tissue. However, survival benefits from vaccination against tumor antigens alone remain modest. Anti-cancer vaccines face numerous challenges, one of them being the immunosuppressive microenvironment. The abnormal tumor vasculature creates a hypoxic microenvironment that polarizes inflammatory cells toward immune suppression. Moreover, tumors systemically alter immune cells' proliferation, differentiation, and function via secretion of growth factors and cytokines.

For cure of cancer, complete eradication of cancer stem cells is of crucial importance. The numerous immune escape mechanisms of human tumors remain a major challenge in cancer immunotherapy. Thus, there exists a great need for improved cancer therapy approaches, which has not been met so far.

WO 2014/005683 discloses an attenuated mutant strain of Salmonella comprising a recombinant DNA molecule encoding a VEGF receptor protein for use in cancer immunotherapy, particularly for use in the treatment of pancreatic cancer.

WO 2014/173542 discloses an attenuated strain of Salmonella comprising a recombinant DNA molecule encoding Wilms' Tumor Protein (WT1) for use in cancer immunotherapy.

WO 2013/09189 discloses a method for growing attenuated mutant Salmonella typhi strains lacking galactose epimerase activity and harboring a recombinant DNA molecule.

OBJECTS OF THE INVENTION

In view of the prior art, it is an object of the present invention to provide novel cancer therapies. Such novel therapies would offer major advantages for improving the treatment options for cancer patients.

SUMMARY OF THE INVENTION

In one aspect the present invention relates to an attenuated strain of Salmonella comprising at least one copy of a DNA molecule comprising an expression cassette encoding a VEGF receptor protein, for use in the treatment of cancer, wherein the treatment further comprises the administration of a further anti-cancer.agent.

The attenuated strain of Salmonella encoding a VEGF receptor protein was surprisingly found to strongly increase the efficacy of cancer therapies which are based on the employment of the patient's immune system, such as treatment with cancer vaccines encoding tumor antigens or tumor stroma antigens, treatment with engineered T-cells that are designed to target tumor cells, treatment with bispecific antibodies designed to mediate the attachment of immune cells to tumor cells, and treatment with checkpoint inhibitors which aim at preventing the tumor induced inhibition of T-cell proliferation.

Surprisingly, it was observed that the administration of the attenuated strain of Salmonella encoding a VEGF receptor protein leads to a significantly increased infiltration of the tumor by $CD8^+$ and $CD4^+$ T-cells. Furthermore, the administration of the attenuated strain of Salmonella encoding a VEGF receptor protein may lead to an increase in the number of activated $CD8^+$ and $CD4^+$ T-cells and/or to a reduction in the number of immunosuppressive lymphoid cells such as Treg cells. Without wishing to be bound by theory, it is believed that the administration of the attenuated strain of Salmonella encoding a VEGF receptor protein improves the efficacy of cancer immunotherapies by enhancing the engagement of T-cells in the eradication of the tumor. The combination of the attenuated strain of Salmonella encoding a VEGF receptor protein with other anti-cancer agents, such as engineered T-cells, checkpoint inhibitors, bispecific antibodies and DNA vaccines encoding tumor antigens or tumor stroma antigens was shown to have synergistic effects on tumor specific T-cell responses and overall survival.

In particular embodiments, the treatment further comprises the administration of at least one DNA vaccine encoding a tumor antigen or a tumor stroma antigen, of at least one checkpoint inhibitor, of at least one engineered T-cell, of at least one bispecific antibody exhibiting binding specificity for one T-cell surface protein and for a tumor antigen or a tumor stroma antigen, or of any combination thereof.

In particular embodiments, the at least one DNA vaccine encoding a tumor antigen or a tumor stroma antigen is selected from at least one further attenuated strain of Salmonella comprising at least one copy of a further DNA molecule comprising a further expression cassette encoding a tumor antigen or a tumor stroma antigen.

In particular embodiments the at least one checkpoint inhibitor is selected from an antibody against PD-1, PD-L1 and CTLA4.

In particular embodiments, the attenuated strain of *Salmonella* and the at least one further attenuated strain of *Salmonella* are of the species *Salmonella enterica*.

In particular embodiments, the attenuated strain of *Salmonella* and the at least one further attenuated strain of *Salmonella* are *Salmonella typhi* Ty21a.

In particular embodiments, the expression cassette and the further expression cassette are a eukaryotic expression cassette, particularly comprising a CMV promoter.

In particular embodiments, the VEGF receptor protein is selected from the group consisting of human VEGFR-2 having the amino acid sequence as found in SEQ ID NO 1 and a protein that shares at least about 80% sequence identity therewith.

In particular embodiments, human VEGFR-2 has the amino acid sequence as found in SEQ ID NO 1.

In particular embodiments, the DNA molecule and the further DNA molecule comprise the kanamycin antibiotic resistance gene, the pMB1 ori, and a CMV promoter.

In particular embodiments, the DNA molecule and the further DNA molecule comprise the DNA sequence as found in SEQ ID NO 2.

In particular embodiments, the tumor antigen encoded by said further attenuated strain of *Salmonella* is selected from the group consisting of human Wilms' Tumor Protein (WT1) having the amino acid sequence as found in SEQ ID NO 3 and a protein that shares at least about 80% sequence identity therewith, human Mesothelin (MSLN) having the amino acid sequence as found in SEQ ID NO 4 and a protein that shares at least about 80% sequence identity therewith, human CEA having the amino acid sequence as found in SEQ ID NO 5 and a protein that shares at least about 80% sequence identity therewith, CMV pp65 having the amino acid sequence as found in SEQ ID NO 6 and a protein that shares at least about 80% sequence identity therewith, CMV pp65 having the amino acid sequence as found in SEQ ID NO 7 and a protein that shares at least about 80% sequence identity therewith and CMV pp65 having the amino acid sequence as found in SEQ ID NO 8 and a protein that shares at least about 80% sequence identity therewith, and the tumor stroma antigen encoded by said further attenuated strain of *Salmonella* is selected from the group consisting of human fibroblast activation protein (FAP).

In particular embodiments, human Wilms' Tumor Protein (WT1) has the amino acid sequence as found in SEQ ID NO 3, human Mesothelin (MSLN) has the amino acid sequence as found in SEQ ID NO 4, human CEA has the amino acid sequence as found in SEQ ID NO 5, and CMV pp65 has the amino acid sequence as found in SEQ ID NO 6, SEQ ID NO 7 or SEQ ID NO 8.

In particular embodiments, the attenuated strain of *Salmonella* is administered simultaneously with or prior to said further anti-cancer agent, i.e. simultaneously with or prior to said at least one DNA vaccine encoding a tumor antigen or a tumor stroma antigen, said at least one checkpoint inhibitor, said at least one engineered T-cell and/or said at least one bispecific antibody.

In particular embodiments, the treatment is accompanied by chemotherapy, radiotherapy or biological cancer therapy. Particularly, the attenuated strain of *Salmonella* is administered before or during the chemotherapy or the radiotherapy treatment cycle or the biological cancer therapy. In other particular embodiments, the attenuated strain of *Salmonella* is administered before and during the chemotherapy or the radiotherapy treatment cycle or the biological cancer therapy.

In particular embodiments, the attenuated strain of *Salmonella* and the at least one further attenuated strain of *Salmonella* are administered orally.

In particular embodiments, the cancer is selected from colorectal cancer, pancreatic cancer, lung cancer, ovarian cancer, mesothelioma, acute myeloid leukemia, chronic myeloid leukemia, glioblastoma, gastric cancer, hepatocellular cancer, renal cell cancer, prostate cancer, and cervical cancer.

In particular embodiments, the single dose of the attenuated strain of *Salmonella* and the at least one further attenuated strain of *Salmonella* comprises from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU).

In particular embodiments, the treatment is individualized cancer immunotherapy comprising the step of assessing the expression pattern of and/or the pre-immune response against said tumor antigen in a patient.

In a further aspect, the present invention relates to a pharmaceutical composition comprising an attenuated strain of *Salmonella* comprising at least one copy of a DNA molecule comprising an expression cassette encoding a VEGF receptor protein, wherein the pharmaceutical composition further comprises at least one further attenuated strain of *Salmonella* comprising at least one copy of a further DNA molecule comprising a further expression cassette encoding a tumor antigen or a tumor stroma antigen.

In particular embodiments, the attenuated strain of *Salmonella* and the at least one further attenuated strain of *Salmonella* is *Salmonella typhi* Ty21a.

In particular embodiments, the expression cassette and the further expression cassette are a eukaryotic expression cassette, particularly comprising a CMV promoter.

In particular embodiments, the VEGF receptor protein is selected from the group consisting of human VEGFR-2 having the amino acid sequence as found in SEQ ID NO 1 and a protein that shares at least about 80% sequence identity therewith.

In particular embodiments, human VEGFR-2 has the amino acid sequence as found in SEQ ID NO 1.

In particular embodiments, the pharmaceutical composition is for use as a medicament, particularly for use in the treatment of cancer.

DETAILED DESCRIPTION OF THE INVENTION

The present invention may be understood more readily by reference to the following detailed description of the invention and the examples included therein.

In one aspect the present invention relates to an attenuated strain of *Salmonella* comprising at least one copy of a DNA molecule comprising an expression cassette encoding a VEGF receptor protein, for use in the treatment of cancer, wherein the treatment further comprises the administration of a further anti-cancer agent.

VEGF receptor proteins are endothelial cell-specific receptor-tyrosine kinases that can be bound by the ligand vascular endothelial growth factor (VEGF) which causes them to dimerize and become activated through transphosphorylation. The VEGF family of growth factors (Kd 75-760 pM) encompasses 6 family members, VEGF-A (also known as VEGF) through E and PLGF (placental growth factor, also known as PGF or PlGF-2). VEGF growth factors regulate growth and differentiation of multiple components of the vascular system, especially blood and lymph vessels. There are three main subtypes of VEGFR, VEGFR-1 (or FLT1), VEGFR-2 (or KDR, FLK1) and VEGFR-3 (or FLT4). Membrane-bound VEGF receptors have an extracellular portion consisting of 7 immunoglobulin-like domains, a single transmembrane spanning region and an intracellular portion containing a split tyrosine-kinase domain. VEGFR transcripts give also rise to alternative splice variants that encode soluble VEGF receptor proteins.

According to the invention, the attenuated *Salmonella* strain functions as the bacterial carrier of the recombinant DNA molecule comprising an expression cassette encoding a VEGF receptor protein for the delivery of said recombinant DNA molecule into a target cell. Such a delivery vector comprising a DNA molecule encoding a heterologous antigen, such as a VEGF receptor protein—a tumor stroma antigen, is termed DNA vaccine.

In the context of the present invention, the term "vaccine" refers to an agent which is able to induce an immune response in a subject upon administration. A vaccine can preferably prevent, ameliorate or treat a disease.

The live attenuated *Salmonella* strain according to the present invention stably carries a recombinant DNA molecule encoding a VEGF receptor protein. It can be used as a vehicle for the oral delivery of this recombinant DNA molecule.

Genetic immunization might be advantageous over conventional vaccination. The target DNA can be detected for a considerable period of time thus acting as a depot of the antigen. Sequence motifs in some plasmids, like GpC islands, are immunostimulatory and can function as adjuvants furthered by the immunostimulation due to LPS and other bacterial components.

Live attenuated *Salmonella* vectors produce their own immunomodulatory factors such as lipopolysaccharides (LPS) in situ which may constitute an advantage over other forms of administration such as microencapsulation. Moreover, the mucosal vaccine according to the present invention has an intra-lymphatic mode of action, which proves to be of benefit. After ingestion of the attenuated vaccine according to the present invention, macrophages and other cells in Peyer's patches of the gut are invaded by the modified bacteria. The bacteria are taken up by these phagocytic cells. Due to their attenuating mutations, bacteria of the *S. typhi* Ty21 strain are not able to persist in these phagocytic cells but die at this time point. The recombinant DNA molecules are released and subsequently transferred into the cytosol of the phagocytic immune cells, either via a specific transport system or by endosomal leakage. Finally, the recombinant DNA molecules enter the nucleus, where they are transcribed, leading to massive VEGF receptor protein expression in the cytosol of the phagocytic cells. The infected cells undergo apoptosis, loaded with the VEGF receptor antigen, and are taken up and processed by the gut's immune system. The danger signals of the bacterial infection serve as a strong adjuvant in this process, leading to a strong target antigen specific CD8+ T-cell and antibody response at the level of both systemic and mucosal compartments. The immune response peaks around ten days after vaccination. The lack of anti-carrier response allows boosting with the same vaccine over many times.

In the context of the present invention, the term "attenuated" refers to a bacterial strain of reduced virulence compared to the parental bacterial strain, not harboring the attenuating mutation. Attenuated bacterial strains have preferably lost their virulence but retained their ability to induce protective immunity. Attenuation can be accomplished by deletion of various genes, including virulence, regulatory, and metabolic genes. Attenuated bacteria may be found naturally or they may be produced artificially in the laboratory, for example by adaptation to a new medium or cell culture or they may be produced by recombinant DNA technology. Administration of about $10^{11}$ CFU of the attenuated strain of *Salmonella* according to the present invention preferably causes Salmonellosis in less than 5%, more preferably less than 1%, most preferably less than 1‰ of subjects.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment the term "comprising" as used throughout the application and in particular within the claims may be replaced by the term "consisting of".

The DNA molecule comprising an expression cassette encoding a VEGF receptor protein is suitably a recombinant DNA molecule, i.e. an engineered DNA construct, preferably composed of DNA pieces of different origin. The DNA molecule can be a linear nucleic acid, or preferably, a circular DNA plasmid generated by introducing an open reading frame encoding a VEGF receptor protein into an expression vector plasmid.

In the context of the present invention, the term "expression cassette" refers to a nucleic acid unit comprising at least one open reading frame (ORF) under the control of regulatory sequences controlling its expression. Expression cassettes can preferably mediate transcription of the included open reading frame encoding a tumor antigen or a tumor stroma antigen, such as the VEGF receptor protein, in a target cell. Expression cassettes typically comprise a promoter, at least one open reading frame and a transcription termination signal.

In particular embodiments, the treatment further comprises the administration of at least one DNA vaccine encoding a tumor antigen or a tumor stroma antigen, of at least one checkpoint inhibitor, of at least one engineered T-cell, of at least one bispecific antibody exhibiting binding specificity for one T-cell surface protein and for a tumor antigen or for a tumor stroma antigen, or of any combination thereof.

In particular embodiments, the at least one bispecific antibody exhibits binding specificity for a tumor antigen selected from CD19, EpCAM, HER2, EGFR, CEA, CD33, EphA2 and MCSP.

In particular embodiments, the at least one engineered T-cell comprises at least one tumor antigen binding protein on its cell surface, wherein the tumor antigen is selected from CEA, FBP, GD2, GD3, Her2-neu, MAGE-A1, MSLN, PSCA, PSMA.

In particular embodiments, the treatment further comprises the administration of one further DNA vaccines encoding a tumor antigen or a tumor stroma antigen, in particular of one further attenuated strain of *Salmonella* comprising at least one copy of a further DNA molecule comprising a further expression cassette encoding a tumor antigen or a tumor stroma antigen.

In particular embodiments, the administration of the attenuated strain of *Salmonella* encoding a VEGF receptor protein is combined with the administration of two further attenuated strains of *Salmonella* each encoding a tumor antigen.

In particular embodiments, the administration of the attenuated strain of *Salmonella* encoding a VEGF receptor protein is combined with the administration of one checkpoint inhibitor.

In particular embodiments, the administration of the attenuated strain of *Salmonella* encoding a VEGF receptor protein is combined with the administration of one further attenuated strains of *Salmonella* encoding a tumor antigen and one checkpoint inhibitor.

In particular embodiments, the administration of the attenuated strain of *Salmonella* encoding a VEGF receptor protein is combined with the administration of one engineered T-cell.

In particular embodiments, the administration of the attenuated strain of *Salmonella* encoding a VEGF receptor protein is combined with the administration of one engineered T-cell and one checkpoint inhibitor.

In particular embodiments, the administration of the attenuated strain of *Salmonella* encoding a VEGF receptor protein is combined with the administration of one bispecific antibody.

In particular embodiments, the administration of the attenuated strain of *Salmonella* encoding a VEGF receptor protein is combined with the administration of one bispecific antibody and one checkpoint inhibitor.

In particular embodiments, the at least one DNA vaccine encoding a tumor antigen or a tumor stroma antigen is selected from at least one further attenuated strain of *Salmonella* comprising at least one copy of a further DNA molecule comprising a further expression cassette encoding a tumor antigen or a tumor stroma antigen.

In particular embodiments the at least one checkpoint inhibitor is selected from an antibody against PD-1, PD-L1 and CTLA4.

In particular embodiments, the attenuated strain of *Salmonella* and the at least one further attenuated strain of *Salmonella* are of the species *Salmonella enterica*. Attenuated derivatives of *Salmonella enterica* are attractive vehicles for the delivery of heterologous antigens to the mammalian immune system, since *S. enterica* strains can potentially be delivered via mucosal routes of immunization, i.e. orally or nasally, which offers advantages of simplicity and safety compared to parenteral administration. Furthermore, *Salmonella* strains elicit strong humoral and cellular immune responses at the level of both systemic and mucosal compartments. Batch preparation costs are low and formulations of live bacterial vaccines are highly stable. Attenuation can be accomplished by deletion of various genes, including virulence, regulatory, and metabolic genes.

Several *Salmonella typhimurium* strains attenuated by aro mutations have been shown to be safe and effective delivery vehicles for heterologous antigens in animal models.

In particular embodiments, the attenuated strain of *Salmonella* and the at least one further attenuated strain of *Salmonella* are *Salmonella typhi* Ty21a. The live, attenuated *S. typhi* Ty21a strain is the active component of Typhoral L®, also known as Vivotif® (manufactured by Berna Biotech Ltd., a Crucell Company, Switzerland). It is currently the only licensed live oral vaccine against typhoid fever. This vaccine has been extensively tested and has proved to be safe regarding patient toxicity as well as transmission to third parties (Wandan et al., J. Infectious Diseases 1982, 145:292-295). The vaccine is licensed in more than 40 countries and has been used in millions of individuals including thousands of children for prophylactic vaccination against typhoid fever. It has an unparalleled safety track record. There is no data available indicating that *S. typhi* Ty21a is able to enter the bloodstream systemically. The live attenuated *Salmonella typhi* Ty21a vaccine strain thus allows specific targeting of the immune system in the gut, while being safe and well-tolerated. The Marketing Authorization number of Typhoral L® is PL 15747/0001 dated 16 Dec. 1996. One dose of vaccine contains at least $2 \times 10^9$ viable *S. typhi* Ty21a colony forming units and at least $5 \times 10^9$ non-viable *S. typhi* Ty21a cells.

This well-tolerated, live oral vaccine against typhoid fever was derived by chemical mutagenesis of the wild-type virulent bacterial isolate *S. typhi* Ty2 and harbors a loss-of-function mutation in the galE gene resulting in its inability to metabolize galactose. The attenuated bacterial strain is also not able to reduce sulfate to sulfide which differentiates it from the wild-type *Salmonella typhi* Ty2 strain. With regard to its serological characteristics, the *Salmonella typhi* Ty21a strain contains the O9-antigen which is a polysaccharide of the outer membrane of the bacteria and lacks the O5-antigen which is in turn a characteristic component of *Salmonella typhimurium*. This serological characteristic supports the rationale for including the respective test in a panel of identity tests for batch release.

In particular embodiments, the expression cassette and the further expression cassette are a eukaryotic expression cassette, particularly comprising a CMV promoter. In the context of the present invention, the term "eukaryotic expression cassette" refers to an expression cassette which allows for expression of the open reading frame in a eukaryotic cell. It has been shown that the amount of heterologous antigen required to induce an adequate immune response may be toxic for the bacterium and may result in cell death, overattenuation or loss of expression of the heterologous antigen. Using a eukaryotic expression cassette that is not expressed in the bacterial vector but only in the target cell may overcome this toxicity problem and the protein expressed typically exhibits a eukaryotic glycosylation pattern.

A eukaryotic expression cassette comprises regulatory sequences that are able to control the expression of an open reading frame in a eukaryotic cell, preferably a promoter and a polyadenylation signal. Promoters and polyadenylation signals included in the recombinant DNA molecules comprised by the attenuated strain of *Salmonella* of the present invention are preferably selected to be functional within the cells of the subject to be immunized. Examples of suitable promoters, especially for the production of a DNA vaccine for humans, include but are not limited to promoters from Cytomegalovirus (CMV), such as the strong CMV immediate early promoter, Simian Virus 40 (SV40), Mouse Mammary Tumor Virus (MMTV), Human Immunodeficiency Virus (HIV), such as the HIV Long Terminal Repeat (LTR) promoter, Moloney virus, Epstein Barr Virus (EBV), and from Rous Sarcoma Virus (RSV), the synthetic CAG promoter composed of the CMV early enhancer element, the promoter, the first exon and the first intron of chicken beta-actin gene and the splice acceptor of the rabbit beta globin gene, as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals, especially for the production of a DNA vaccine for humans, include but are not limited to the bovine growth hormone (BGH) polyadenylation site, SV40 polyadenylation signals and LTR polyadenylation signals. In a particular embodiment, the eukaryotic expression cassette included in the recombinant DNA molecule comprised by the attenuated strain of *Salmonella* of the present invention comprises the BGH polyadenylation site.

In addition to the regulatory elements required for expression of the heterologous tumor antigen or tumor stroma antigen gene, like a promoter and a polyadenylation signal, other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

In particular embodiments, the VEGF receptor protein is selected from the group consisting of human VEGFR-2 having the amino acid sequence as found in SEQ ID NO 1 and a protein that shares at least about 80% sequence identity therewith.

VEGFR-2, also known as kinase-insert-domain-containing receptor (KDR), appears to mediate almost all of the known cellular responses to VEGF. For example, the role of VEGF in angiogenesis appears to be mediated through the interaction of this protein with VEGFR-2. VEGFR-2 is a 1356 amino acid long, 200-230 kDa molecular weight high-affinity receptor for VEGF, as well as for VEGF-C and VEGF-D. Identified in humans through the screening of endothelial cDNA for tyrosine kinase receptors, VEGFR-2 shares 85% sequence identity with the previously discovered mouse fetal liver kinase 1 (Flk-1). VEGFR-2 is normally expressed in endothelial and hematopoietic precursors, as well as in endothelial cells, nascent hematopoietic stem cells and the umbilical cord stroma. However, in quiescent adult vasculature, VEGFR-2 mRNA appears to be down regulated.

The extracellular domain of VEGFR-2 contains 18 potential N-linked glycosylation sites. VEGFR-2 is initially synthesized as a 150 kDa protein and rapidly glycosylated to a 200 kDa intermediate form, and then further glycosylated at a slower rate to a mature 230 kDa protein which is expressed on the cell surface.

In this context, the term "about" or "approximately" means within 80% to 120%, alternatively within 90% to 110%, including within 95% to 105% of a given value or range.

In the context of the present invention, the term "protein that shares at least about 80% sequence identity with a given protein (the reference protein) refers to a protein that may differ in the amino acid sequence and/or the nucleic acid sequence encoding the amino acid sequence of the reference protein. The protein may be of natural origin, e.g. a mutant version of a wild-type protein, e.g. a mutant version of a wild type VEGF receptor protein, or a homolog of a different species, or an engineered protein, e.g. an engineered VEGF receptor protein. It is known that the usage of codons is different between species. Thus, when expressing a heterologous protein in a target cell, it may be necessary, or at least helpful, to adapt the nucleic acid sequence to the codon usage of the target cell. Methods for designing and constructing derivatives of a given protein are well known to anyone of ordinary skill in the art.

Figure 17:
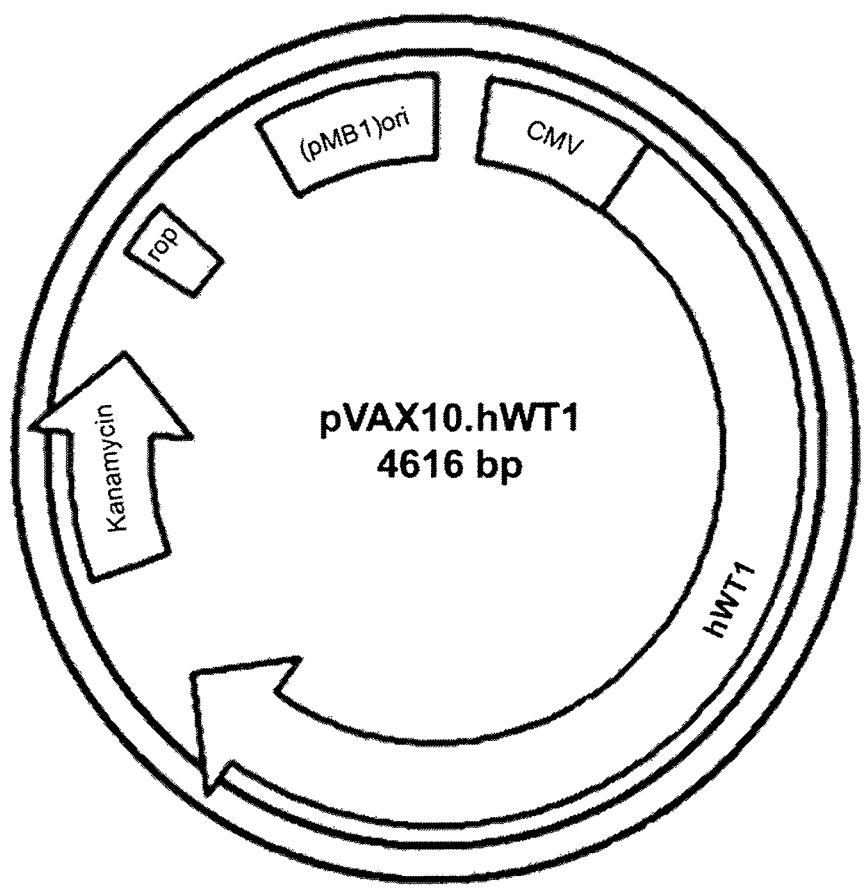

The protein that shares at least about 80% sequence identity with a given protein may contain one or more mutations comprising an addition, a deletion and/or a substitution of one or more amino acids in comparison to the given reference protein. According to the teaching of the present invention, said deleted, added and/or substituted amino acids may be consecutive amino acids or may be interspersed over the length of the amino acid sequence of the protein that shares at least about 80% sequence identity with a given reference protein. According to the teaching of the present invention, any number of amino acids may be added, deleted, and/or substitutes, as long as the amino acid sequence identity with the reference protein is at least about 80% and the mutated protein is immunogenic. Preferably, the immunogenicity of the protein which shares at least about 80% sequence identity with a reference protein of a given amino acid sequence is reduced by less than 50%, less than 40%, less than 30%, less than 20%, less than 10%, less than 5% or less than 1% compared to the reference protein of the given amino acid sequence, as measured by ELISA. Methods for designing and constructing protein homologues and for testing such homologues for their immunogenic potential are well known to anyone of ordinary skill in the art. In particular embodiments, the sequence identity with the reference protein is at least about 80%, at least about 85%, at least about 90%, or most particularly at least about 95%. Methods and algorithms for determining sequence identity including the comparison of a parental protein and its derivative having deletions, additions and/or substitutions relative to a parental sequence, are well known to the practitioner of ordinary skill in the art. On the DNA level, the nucleic acid sequences encoding the protein that shares at least about 80% sequence identity with the VEGF receptor protein may differ to a larger extent due to the degeneracy of the genetic code.

In particular embodiments, human VEGFR-2 has the amino acid sequence as found in SEQ ID NO 1.

In particular embodiments, the DNA molecule and the further DNA molecule comprise the kanamycin antibiotic resistance gene, the pMB1 ori, and a CMV promoter. In particular embodiments, the recombinant DNA molecule is derived from commercially available pVAX1™ expression plasmid (Invitrogen, San Diego, Calif.). This expression vector was modified by replacing the high copy pUC origin of replication by the low copy pMB1 origin of replication of pBR322. The low copy modification was made in order to reduce the metabolic burden and to render the construct more stable. The generated expression vector backbone was designated pVAX10.

In particular embodiments, the DNA molecule and the further DNA molecule comprise the DNA sequence as found in SEQ ID NO 2 (vector backbone pVAX10).

Inserting the VEGF receptor protein encoding ORF with the nucleic acid sequence as found in SEQ ID NO 9 into this expression vector backbone via NheI/XhoI yielded the expression plasmid pVAX10.VR2-1 (WO 2013/091898). The expression plasmid pVAX10.VR2-1 is schematically depicted in FIG. 16. The DNA vaccine comprising the attenuated *Salmonella* strain Ty21a harboring the expression plasmid pVAX10.VR2-1 is designated VXM01 (WO 2013/091898).

Inserting human, truncated WT1 encoding ORF with the nucleic acid sequence as found in SEQ ID NO 10 into the expression vector backbone via NheI/XhoI yielded the expression plasmid pVAX10.hWT1. The expression plasmid pVAX10.hWT1 is schematically depicted in FIG. 17. The DNA vaccine comprising the attenuated *Salmonella* strain Ty21a harboring the expression plasmid pVAX10.hWT1 is designated VXM06 (WO 2014/173542).

Figure 18:
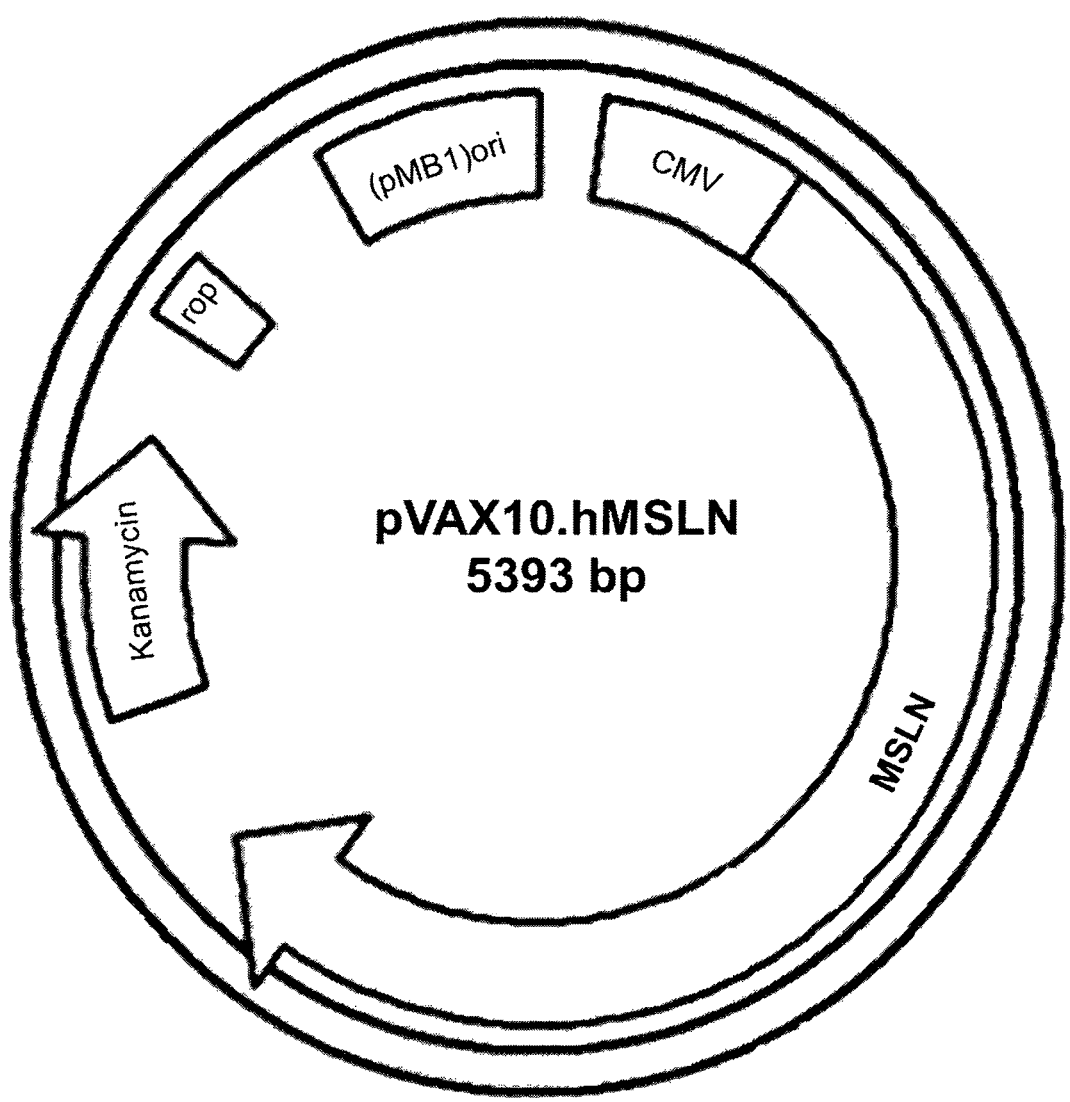

Inserting human MSLN encoding ORF with the nucleic acid sequence as found in SEQ ID NO 11 into the expression vector backbone via NheI/XhoI yielded the expression plasmid pVAX10.hMSLN. The expression plasmid pVAX10.hMSLN is schematically depicted in FIG. 18. The DNA vaccine comprising the attenuated *Salmonella* strain Ty21a harboring the expression plasmid pVAX10.hMSLN is designated VXM04.

Figure 19:
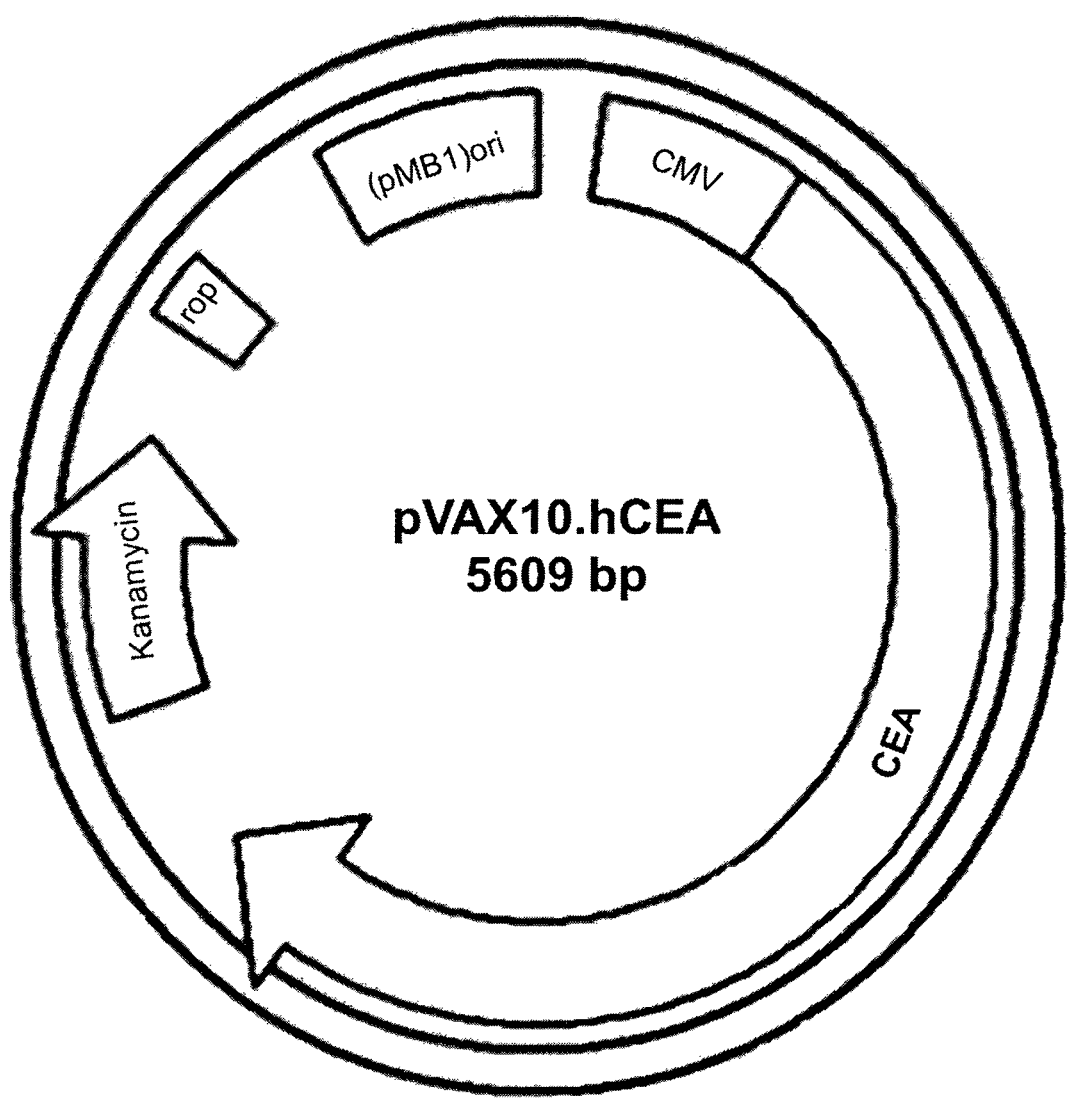

Inserting human CEA encoding ORF with the nucleic acid sequence as found in SEQ ID NO 12 into the expression vector backbone via NheI/XhoI yielded the expression plasmid pVAX10.hCEA. The expression plasmid pVAX10.hCEA is schematically depicted in FIG. 19. The DNA vaccine comprising the attenuated *Salmonella* strain Ty21a harboring the expression plasmid pVAX10.hCEA is designated VXM08.

Figure 20:
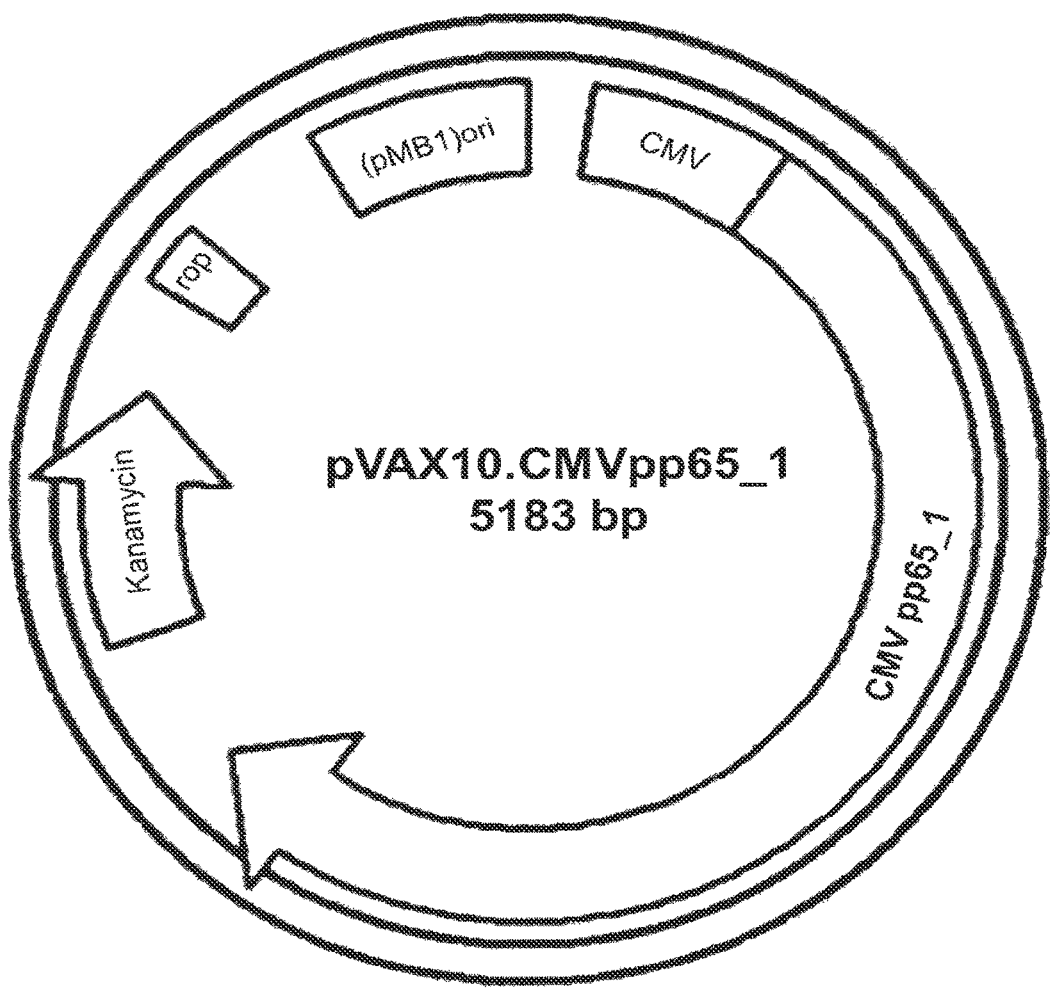

Inserting CMV pp65 encoding ORF with the nucleic acid sequence as found in SEQ ID NO 13 into the expression vector backbone via NheI/XhoI yielded the expression plasmid pVAX10.CMVpp65_1. The expression plasmid pVAX10.CMVpp65_1 is schematically depicted in FIG. 20. The DNA vaccine comprising the attenuated *Salmonella* strain Ty21a harboring the expression plasmid pVAX10.CMVpp65_1 is designated VXM65_1.

Figure 21:
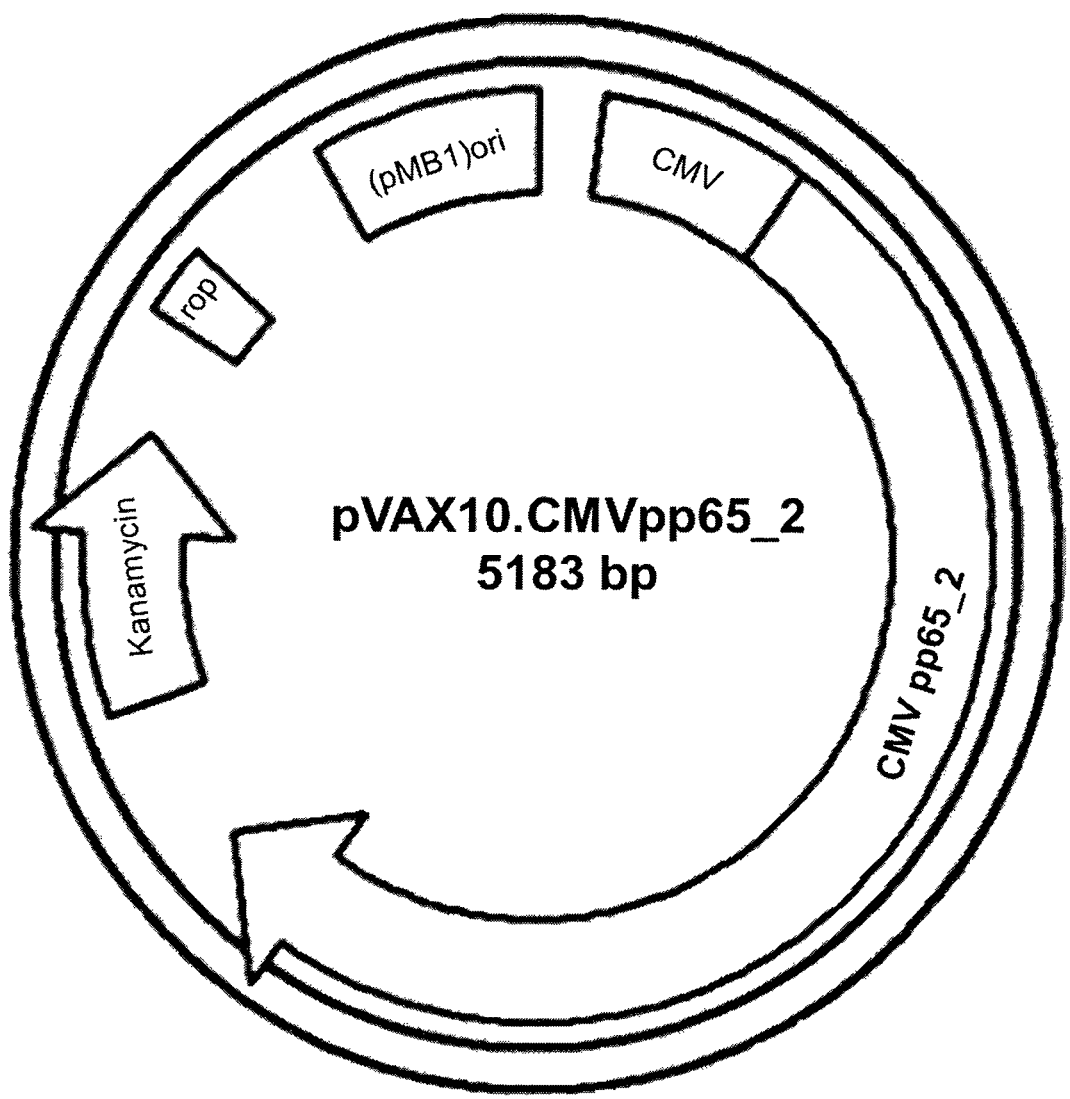

Inserting CMV pp65 encoding ORF with the nucleic acid sequence as found in SEQ ID NO 14 into the expression vector backbone via NheI/XhoI yielded the expression plasmid pVAX10.CMVpp65_2. The expression plasmid pVAX10.CMVpp65_2 is schematically depicted in FIG. 21. The DNA vaccine comprising the attenuated *Salmonella* strain Ty21a harboring the expression plasmid pVAX10.CMVpp65_2 is designated VXM65_2.

Figure 22:
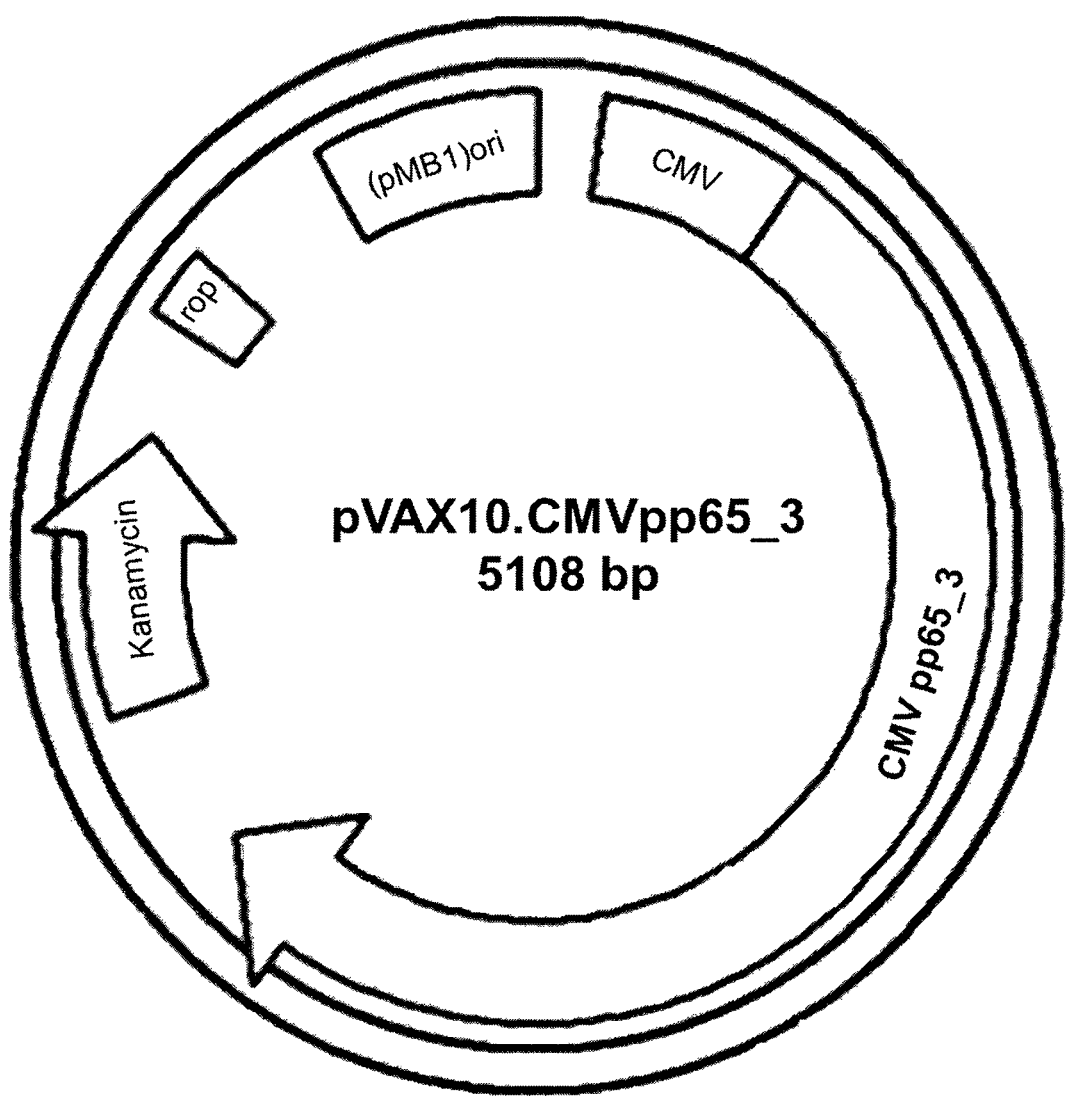

Inserting CMV pp65 encoding ORF with the nucleic acid sequence as found in SEQ ID NO 15 into the expression vector backbone via NheI/XhoI yielded the expression plasmid pVAX10.CMVpp65_3. The expression plasmid pVAX10.CMVpp65_3 is schematically depicted in FIG. 22. The DNA vaccine comprising the attenuated *Salmonella* strain Ty21a harboring the expression plasmid pVAX10.CMVpp65_3 is designated VXM65_3.

In particular embodiments, the tumor antigen encoded by said further attenuated strain of *Salmonella* is selected from the group consisting of human Wilms' Tumor Protein (WT1) having the amino acid sequence as found in SEQ ID NO 3 and a protein that shares at least about 80% sequence identity therewith, human Mesothelin (MSLN) having the amino acid sequence as found in SEQ ID NO 4 and a protein that shares at least about 80% sequence identity therewith, human CEA having the amino acid sequence as found in SEQ ID NO 5 and a protein that shares at least about 80% sequence identity therewith, CMV pp65 having the amino acid sequence as found in SEQ ID NO 6 and a protein that shares at least about 80% sequence identity therewith, CMV pp65 having the amino acid sequence as found in SEQ ID NO 7 and a protein that shares at least about 80% sequence identity therewith and CMV pp65 having the amino acid sequence as found in SEQ ID NO 8 and a protein that shares at least about 80% sequence identity therewith, and the tumor stroma antigen encoded by said further attenuated strain of *Salmonella* is selected from the group consisting of human fibroblast activation protein (FAP).

In particular embodiments, human Wilms' Tumor Protein (WT1) has the amino acid sequence as found in SEQ ID NO 3, human Mesothelin (MSLN) has the amino acid sequence as found in SEQ ID NO 4, human CEA has the amino acid sequence as found in SEQ ID NO 5, and CMV pp65 has the amino acid sequence as found in SEQ ID NO 6, or SEQ ID NO 7, or SEQ ID NO 8.

Mesothelin is a 40-kDa cell surface glycoprotein present on normal mesothelial cells and overexpressed in several human tumors, including mesothelioma and ovarian and pancreatic adenocarcinoma. The mesothelin gene encodes a precursor protein of 71-kDa that is processed to yield a 31-kDa shed protein named megakaryocyte-potentiating factor (MPF) and the 40-kDa cell bound fragment mesothelin. Mesothelin was shown to exhibit megakaryocyte-colony-forming activity in the presence of interleukin-3. Mesothelin is a tumor differentiation antigen present at low levels on a restricted set of normal adult tissues, such as mesothelium, but aberrantly overexpressed in a wide variety of human tumors including mesotheliomas, ovarian and pancreatic cancers, squamous cell carcinomas of the cervix, head and neck, vulva, lung and esophagus, lung adenocarcinomas, endometrial carcinomas, biphasic synovial sarcomas, desmoplastic small round cell tumors and gastric adenocarcinomas. The normal biological function of Mesothelin is unknown. Studies in mesothelin knock-out mice revealed no detectable phenotype, and both male and female mice produced healthy off-spring. Studies in pancreatic cancer suggest that mesothelin plays a role in tumorigenesis by increasing cellular proliferation, migration, and S-phase cell populations. Furthermore, there is evidence that mesothelin is an immunogenic protein. Due to its expression profile, its oncogenic functions and its immunogenic potential, the tumor antigen mesothelin is a promising candidate for the development of cancer vaccines.

Wilms' tumor gene 1 (WT1) encodes a zinc finger transcription factor involved in cell proliferation and differentiation. The WT1 protein contains four zinc finger motifs at the C-terminus and a proline/glutamine-rich DNA-binding domain at the N-terminus. Multiple transcript variants, resulting from alternative splicing at two coding exons, have been well characterized. WT1 plays an essential role in the development of the urogenital system and is involved in cell proliferation and differentiation. The WT1 gene was isolated as the gene responsible for a childhood renal neoplasm, Wilms' tumor. It is highly expressed in a wide variety of malignancies including several types of hematological malignancies and various solid tumors. In contrast, normal tissue expression of WT1 in adults is restricted to gonads, uterus, kidney, mesothelium and progenitor cells in various types of tissues. WT-1 negatively affects differentiation and promotes proliferation of progenitor cells. Furthermore, overexpressed WT1 is immunogenic; WT1 specific T-cells as well as IgG anti-WT1 antibodies have been observed in cancer patients. Due to its expression profile, its oncogenic functions and its immunogenic potential, the tumor antigen WT1 is a promising candidate for the development of cancer vaccines.

In particular embodiments, WT1 is truncated. In particular embodiments, the zinc finger domain of WT1 is deleted. In particular embodiments, the truncated WT1 has the amino acid sequence as found in SEQ ID NO 3.

The zinc finger domain at the C-terminus of WT1 comprises four zinc finger motifs. Truncated WT1 of the amino acid sequence as found in SEQ ID NO 3 represents amino acids 1 to 371 of UniProt ref P19544-7. Deletion of the zinc finger domain minimizes the risk of immunological cross reactivity with other zinc finger containing transcription factors. Furthermore, truncated WT1 lacking the zinc finger domain has greater immunogenic potential than full-length WT1. In addition, deletion of the zinc finger motifs, which are essential for DNA binding, abrogates the oncogenic potential of WT1, thus minimizing the risk of oncogenesis.

The tegument protein CMV pp65 is a major immunodominant protein of human cytomegalovirus (CMV). The biologic function of CMV pp65 is unclear, but it is believed to be involved in cell cycle regulation. CMV pp65 is a nucleotropic protein exhibiting protein kinase activity, which is able to bind polo-like kinase 1 (PLK-1).

HCMV pp65 is expressed in more than 90% of glioblastoma specimens but not in surrounding normal brain. This viral protein is thus a promising candidate as tumor-specific target for the development novel of cancer immunotherapies.

The CMV pp65 protein contains two bipartite nuclear localization signals (NLSs) at amino acids 415 to 438 and amino acids 537 to 561 near the carboxy terminus and a phosphate binding site related to its kinase activity at lysine-436. Mutating the lysine at position 436 to asparagine and deletion of amino acids 537 to 561 results in a protein without kinase activity and markedly reduced nuclear localization. This mutant protein exhibits unaltered immunogenicity.

In particular embodiments, the CMV pp65 has the amino acid sequence as found in SEQ ID NO 6. SEQ ID NO 6 represents the amino acid sequence of wild type human CMV pp65.

In particular other embodiments, the CMV pp65 has the amino acid sequence as found in SEQ ID NO 7. SEQ ID NO 7 represents the amino acid sequence of human CMV pp65, which harbors the mutation K436N relative to the wild type human CMV pp65 of SEQ ID NO 6.

In particular other embodiments, the CMV pp65 has the amino acid sequence as found in SEQ ID NO 8. SEQ ID NO 8 represents the amino acid sequence of a truncated version of CMV pp65 of SEQ ID NO 7, which lacks the second, more C-terminal NLS (nuclear localization sequence) (i.e. amino acids 537 to 561 of CMV pp65 of SEQ ID NO 7).

Carcinoembryonic antigen (CEA) (also known as CEACAM5 and CD66e) is a member of a family of highly related glycosyl phosphatidyl inositol (GPI) cell surface anchored glycoproteins involved in cell adhesion. CEA is normally produced in gastrointestinal tissue during fetal development; protein expression ends before birth. Therefore CEA is usually present only at very low levels in the blood of healthy adults. However, the serum levels are raised in some types of cancer, in particular colorectal carcinoma, thus serving as tumor marker. CEA levels may also be raised in gastric carcinoma, pancreatic carcinoma, lung carcinoma, breast carcinoma, and medullary thyroid carcinoma, as well as some non-neoplastic conditions like ulcerative colitis, pancreatitis, cirrhosis, COPD, Crohn's disease and hypothyroidism.

In particular embodiments, the attenuated strain of Salmonella is administered simultaneously with or prior to said further anti-cancer agent, i.e. simultaneously with or prior to said at least one DNA vaccine encoding a tumor antigen or a tumor stroma antigen, said at least one checkpoint inhibitor, said at least one engineered T-cell and/or said at least one bispecific antibody.

In the context of the present invention, the term "simultaneously with" means administration of the attenuated strain of Salmonella encoding a VEGF receptor protein and the at least one further anti-cancer agent on the same day, more particularly within 12 hours, more particularly within 2 hours.

In particular embodiments, administration of the attenuated Salmonella strain encoding a VEGF receptor protein and the at least one further anti-cancer agent occurs within eight consecutive weeks, more particularly within three to six consecutive weeks. The attenuated Salmonella strain according to the present invention and the at least one further anti-cancer agent may be administered via the same route or via different routes.

In particular embodiments, the treatment is accompanied by chemotherapy, radiotherapy or biological cancer therapy. For cure of cancer, complete eradication of cancer stem cells may be essential. For maximal efficacy, a combination of different therapy approaches may be beneficial.

In the context of the present invention, the term "biological cancer therapy" refers to cancer therapy involving the use of substances derived from living organisms or laboratory-produced versions of such substances. Biological cancer therapy approaches include the administration of immunostimulatory cytokines.

Chemotherapeutic agents that may be used in combination with the attenuated mutant strain of Salmonella of the present invention may be, for example: gemcitabine, amifostine (ethyol), cabazitaxel, cisplatin, dacarbazine (DTIC), dactinomycin, docetaxel, mechlorethamine, streptozocin, cyclophosphamide, carrnustine (BCNU), lomustine (CCNU), doxorubicin (adriamycin), doxorubicin lipo (doxil), folinic acid, gemcitabine (gemzar), daunorubicin, daunorubicin lipo (daunoxome), procarbazine, ketokonazole, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, oxaliplatin, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof.

Most preferred chemotherapeutic agents according to the invention are cabazitaxel, carboplatin, oxaliplatin, cisplatin, cyclophosphamide, docetaxel, gemcitabine, doxorubicin, paclitaxel (taxol), irinotecan, vincristine, vinblastine, vinorelbin, folinic acid, 5-fluorouracil and bleomycin, especially gemcitabine.

Particularly, the attenuated strain of Salmonella is administered before or during the chemotherapy or the radiotherapy treatment cycle or the biological cancer therapy. In other particular embodiments, the attenuated strain of Salmonella is administered before and during the chemotherapy or the radiotherapy treatment cycle or the biological cancer therapy.

In particular embodiments, the attenuated strain of Salmonella and the at least one further attenuated strain of Salmonella are administered orally. Oral administration is simpler, safer and more comfortable than parenteral administration. However, it has to be noted that the attenuated strain of Salmonella of the present invention may also be administered by any other suitable route. Preferably, a therapeutically effective dose is administered to the subject, and this dose depends on the particular application, the type of malignancy, the subject's weight, age, sex and state of health, the manner of administration and the formulation, etc. Administration may be single or multiple, as required.

The attenuated strain of *Salmonella* encoding a VEGF receptor protein and the at least one further attenuated strain of *Salmonella* encoding a tumor antigen or a tumor stroma antigen may be provided in the form of a solution, a suspension, a lyophilisate, an enteric coated capsule, or any other suitable form. Typically, the attenuated strain of *Salmonella* is formulated as drinking solution. This embodiment offers the advantage of improved patient compliance. Preferably, the drinking solution comprises means to neutralize gastric acids at least to a certain degree, i.e. to bring the pH of the gastric juice closer to a pH of 7. Preferably, the drinking solution is a buffered suspension comprising the attenuated strain of *Salmonella* according to the present invention. In a particular embodiment, the buffered suspension is obtained by suspending the attenuated strain of *Salmonella* in a suitable buffer, preferably containing 2.6 g sodium hydrogen carbonate, 1.7 g L-ascorbic acid, 0.2 g lactose monohydrate and 100 ml of drinking water.

The at least one further anti-cancer agent selected from at least one checkpoint inhibitor, at least one engineered T-cell, and at least one bispecific antibody exhibiting binding specificity for one T-cell surface protein and for a tumor antigen or for a tumor stroma antigen is preferably administered in the approved galenic formulation of the commercial product.

In particular embodiments, the cancer is selected from colorectal cancer, pancreatic cancer, lung cancer, ovarian cancer, mesothelioma, acute myeloid leukemia, chronic myeloid leukemia, glioblastoma, gastric cancer, hepatocellular cancer, renal cell cancer, prostate cancer, and cervical cancer.

The attenuated strain of *Salmonella* encoding a VEGF receptor protein together with another anti-cancer agent such as at least one checkpoint inhibitor, bispecific antibody, engineered T-cell and DNA vaccine encoding a tumor antigen or a tumor stroma antigen surprisingly show synergistic effects on T-cell responses and/or overall survival at relatively low doses of the attenuated strain of *Salmonella* encoding a VEGF receptor protein. Similarly, DNA vaccines comprising an attenuated strain of *Salmonella* encoding a tumor antigen or a tumor stroma antigen are surprisingly effective at relatively low doses. Administration of low doses of live bacterial vaccines minimizes the risk of excretion and thus of transmission to third parties.

In particular embodiments, the single dose of the attenuated strain of *Salmonella* and the at least one further attenuated strain of *Salmonella* comprises from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU).

In particular embodiments, the single dose of both the attenuated strain of *Salmonella* encoding a VEGF receptor protein and the at least one further attenuated strain of *Salmonella* encoding a tumor antigen or a tumor stroma antigen are essentially the same, both single doses comprising from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU). In particular embodiments, the single dose of the attenuated strain of *Salmonella* encoding a VEGF receptor protein is from about 10 to about 100 times lower than the single dose of the at least one further attenuated strain of *Salmonella* encoding a tumor antigen or a tumor stroma antigen. In particular other embodiments, the single dose of the attenuated strain of *Salmonella* encoding a VEGF receptor protein is from about 10 to about 100 times higher than the single dose of the at least one further attenuated strain of *Salmonella* encoding a tumor antigen or a tumor stroma antigen.

In this context, the term "about" or "approximately" means within a factor of 3, alternatively within a factor of 2, including within a factor of 1.5 of a given value or range.

In particular embodiments, the treatment is individualized cancer immunotherapy comprising the step of assessing the expression pattern of and/or the pre-immune response against said tumor antigen in a patient. The patient's tumor and/or stromal antigen expression pattern and/or the patient's pre-immune responses against tumor and/or stromal antigens may be assessed in a first step for example by companion diagnostics targeting the patient's specific tumor and/or stromal antigen pattern. Depending on the patient's tumor and/or stromal antigen expression pattern or the patient's pre-immune responses against tumor and/or stromal antigens, the attenuated strain of *Salmonella* encoding a VEGF receptor protein may be administered in combination with one or more suitable further *Salmonella typhi* Ty21a based cancer vaccine(s) comprising eukaryotic expression systems.

It may be favorable dependent on the occurrence of possible side effects, to include treatment with antibiotics or anti-inflammatory agents.

Should adverse events occur that resemble hypersensitivity reactions mediated by histamine, leukotrienes, or cytokines, treatment options for fever, anaphylaxis, blood pressure instability, bronchospasm, and dyspnoea are available. Treatment options in case of unwanted T-cell derived autoaggression are derived from standard treatment schemes in acute and chronic graft vs. host disease applied after stem cell transplantation. Cyclosporin and glucocorticoids are proposed as treatment options.

In the unlikely case of systemic *Salmonella typhi* Ty21a type infection, appropriate antibiotic therapy is recommended, for example with fluoroquinolones including ciprofloxacin or ofloxacin. Bacterial infections of the gastrointestinal tract are to be treated with respective agents, such as rifaximin.

In a further aspect, the present invention relates to a pharmaceutical composition comprising an attenuated strain of *Salmonella* comprising at least one copy of a DNA molecule comprising an expression cassette encoding a VEGF receptor protein, wherein the pharmaceutical composition further comprises at least one further attenuated strain of *Salmonella* comprising at least one copy of a further DNA molecule comprising a further expression cassette encoding a tumor antigen or a tumor stroma antigen.

In particular embodiments, the pharmaceutical composition comprises the DNA vaccines VXM01 and VXM06.

In particular embodiments, the pharmaceutical composition comprises the DNA vaccines VXM01 and VXM04.

In particular embodiments, the pharmaceutical composition comprises the DNA vaccines VXM01 and VXM08.

In particular embodiments, the pharmaceutical composition comprises the DNA vaccines VXM01 and VXM65.

In particular embodiments, the least one further attenuated strain of *Salmonella* comprises at least one copy of a further DNA molecule comprising a further expression cassette encoding a tumor antigen or a tumor stroma antigen selected from the group consisting of human Wilms' Tumor Protein (WT1) having the amino acid sequence as found in SEQ ID NO 3 and a protein that shares at least about 80% sequence identity therewith, human Mesothelin (MSLN) having the amino acid sequence as found in SEQ ID NO 4 and a protein that shares at least about 80% sequence identity therewith, human CEA having the amino acid sequence as found in SEQ ID NO 5 and a protein that shares at least about 80% sequence identity therewith, CMV pp65 having the amino acid sequence as found in SEQ ID NO 6 and a protein that shares at least about 80% sequence identity therewith, CMV pp65 having the amino acid sequence as found in SEQ ID NO 7 and a protein that shares at least about 80% sequence identity therewith and CMV pp65 having the amino acid sequence as found in SEQ ID NO 8 and a protein that shares at least about 80% sequence identity therewith, particularly wherein human Wilms' Tumor Protein (WT1) has the amino acid sequence as found in SEQ ID NO 3, human Mesothelin (MSLN) has the amino acid sequence as found in SEQ ID NO 4, human CEA has the amino acid sequence as found in SEQ ID NO 5, and CMV pp65 has the amino acid sequence as found in SEQ ID NO 6, SEQ ID NO 7 or SEQ ID NO 8, and wherein the tumor stroma antigen is selected from fibroblast activation protein (FAP).

The pharmaceutical composition of the present invention may be in the form of a solution, a suspension, an enteric coated capsule, a lyophilized powder or any other form suitable for the intended use.

The pharmaceutical composition of the present invention may further comprises one or more pharmaceutically acceptable excipients.

In the context of the present invention, the term "excipient" refers to a natural or synthetic substance formulated alongside the active ingredient of a medication. Suitable excipients include antiadherents, binders, coatings, disintegrants, flavors, colors, lubricants, glidants, sorbents, preservatives and sweeteners.

In the context of the present invention, the term "pharmaceutically acceptable" refers to molecular entities and other ingredients of pharmaceutical compositions that are physiologically tolerable and do not typically produce untoward reactions when administered to a mammal (e.g., human). The term "pharmaceutically acceptable" may also mean approved by a regulatory agency of a Federal or a state government or listed in the U.S. Pharmacopeia or other generally recognized pharmacopeia for use in mammals, and, more particularly, in humans.

In particular embodiments, wherein the anti-cancer agent is selected from at least one further attenuated strain of Salmonella comprising harboring a tumor antigen or a tumor stroma antigen, the pharmaceutical composition according to the present invention may suitably be provided as drinking solution. This embodiment offers the advantage of improved patient compliance and allows for rapid, feasible and affordable mass vaccination programs, especially in poor geographies.

In particular, suitable drinking solutions comprise means to neutralize gastric acids to at least to a certain degree, i.e. to bring the pH of the gastric juice closer to a pH of 7. In a particular embodiment, the drinking solution is a buffered suspension obtained by suspending the attenuated strain of Salmonella according to the present invention in a suitable buffer, preferably in a buffer that neutralizes gastric acids to at least a certain degree, preferably in a buffer containing 2.6 g sodium hydrogen carbonate, 1.7 g L-ascorbic acid, 0.2 g lactose monohydrate and 100 ml of drinking water.

In particular embodiments, the attenuated strain of Salmonella and the at least one further attenuated strain of Salmonella is Salmonella typhi Ty21a.

In particular embodiments, the expression cassette and the further expression cassette are a eukaryotic expression cassette, particularly comprising a CMV promoter.

In particular embodiments, the VEGF receptor protein is selected from the group consisting of human VEGFR-2 having the amino acid sequence as found in SEQ ID NO 1 and a protein that shares at least about 80% sequence identity therewith.

In particular embodiments, human VEGFR-2 has the amino acid sequence as found in SEQ ID NO 1.

In particular embodiments, the pharmaceutical composition is for use as a medicament, particularly for use in the treatment of cancer.

In particular embodiments, the treatment comprises a single or multiple administrations of the attenuated strain of Salmonella encoding a VEGF receptor protein or the pharmaceutical composition according to the present invention. The single dose of the administrations may be the same or different. In particular, the treatment comprises 1, 2, 3, 4, 5 or 6 administrations of the attenuated strain of Salmonella encoding a VEGF receptor protein or the pharmaceutical composition according to the present invention, preferably wherein the multiple administrations occur within three to six consecutive months.

SHORT DESCRIPTION OF FIGURES AND TABLES

FIG. 1: Amino acid sequence of human VEGFR-2 encoded by VEGFR-2 cDNA contained in plasmid pVAX10.VR2-1 (corresponding to SEQ ID NO 1)

FIG. 2: Nucleic acid sequence comprised in empty expression vector pVAX10 (sequence of expression vector pVAX10 without the portion of the multiple cloning site which is located between the restriction sites NheI and XhoI (SEQ ID NO 2).

FIG. 3: Amino acid sequence of truncated human WT-1 encoded by WT-1 cDNA contained in plasmid pVAX10.hWT1 (SEQ ID NO 3)

FIG. 4: Amino acid sequence of human MSLN encoded by MSLN cDNA contained in plasmid pVAX10.hMSLN (SEQ ID NO 4)

FIG. 5: Amino acid sequence of human CEA encoded by CEA cDNA contained in plasmid pVAX10.hCEA (SEQ ID NO 5)

FIG. 6: Amino acid sequence of CMV pp65 encoded by CMV pp65 cDNA contained in plasmid pVAX10.CMVpp65_1 (SEQ ID NO 6)

FIG. 7: Amino acid sequence of CMV pp65 encoded by CMV pp65 cDNA contained in plasmid pVAX10.CMVpp65_2 (SEQ ID NO 7)

FIG. 8: Amino acid sequence of CMV pp65 encoded by CMV pp65 cDNA contained in plasmid pVAX10.CMVpp65_3 (SEQ ID NO 8)

FIG. 9: Nucleic acid sequence contained in plasmid pVAX10.VR2-1 and encoding human VEGFR-2 of SEQ ID NO 1

FIG. 10: Nucleic acid sequence contained in plasmid pVAX10.hWT1 and encoding human WT-1 of SEQ ID NO 3

FIG. 11: Nucleic acid sequence contained in plasmid pVAX10.hMSLN and encoding human MSLN of SEQ ID NO 4

FIG. 12: Nucleic acid sequence contained in plasmid pVAX10.hCEA and encoding human CEA of SEQ ID NO 5

FIG. 13: Nucleic acid sequence contained in plasmid pVAX10.CMVpp65_1 and encoding CMV pp65 of SEQ ID NO 6

FIG. 14: Nucleic acid sequence contained in plasmid pVAX10.CMVpp65_2 and encoding CMV pp65 of SEQ ID NO 7

FIG. 15: Nucleic acid sequence contained in plasmid pVAX10.CMVpp65_3 and encoding CMV pp65 of SEQ ID NO 8

FIG. 16: Plasmid map of pVAX10.VR2-1

FIG. 17: Plasmid map of pVAX10.hWT1

FIG. 18: Plasmid map of pVAX10.hMSLN

FIG. 19: Plasmid map of pVAX10.hCEA

FIG. 20: Plasmid map of pVAX10.CMVpp65_1

FIG. 21: Plasmid map of pVAX10.CMVpp65_2

FIG. 22: Plasmid map of pVAX10.CMVpp65_3

Figure 23:
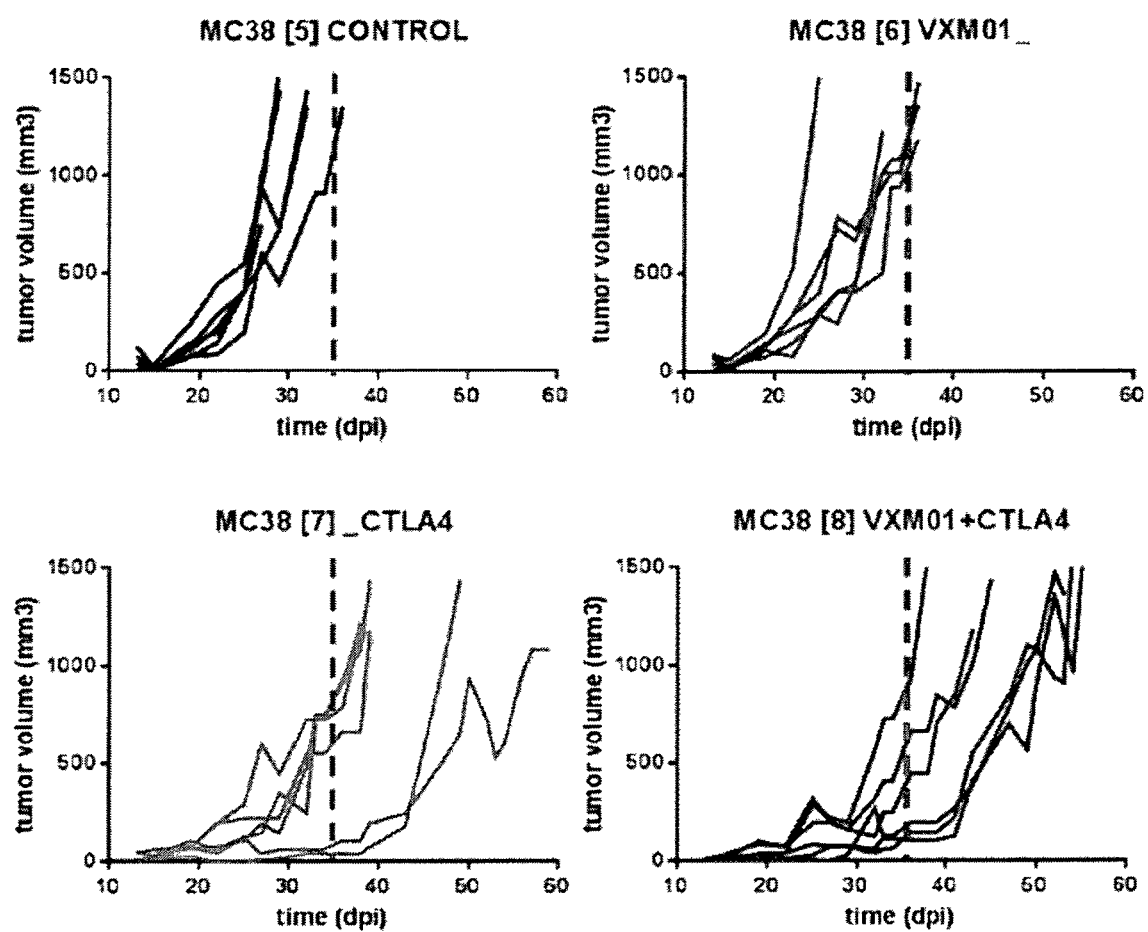

FIG. 23: Effects of the combined administration of VXM01 and anti-CTLA4 in a MC38 mouse tumor model-tumor growth FIG. 24: Effects of the combined administration of VXM01 and anti-CTLA4 in a MC38 mouse tumor model-survival FIG. 25: Effects of the combined administration of VXM01 and anti-CTLA4 in B16 mouse tumor model-survival FIG. 26: Treatment schedule Example 3

Figure 27:
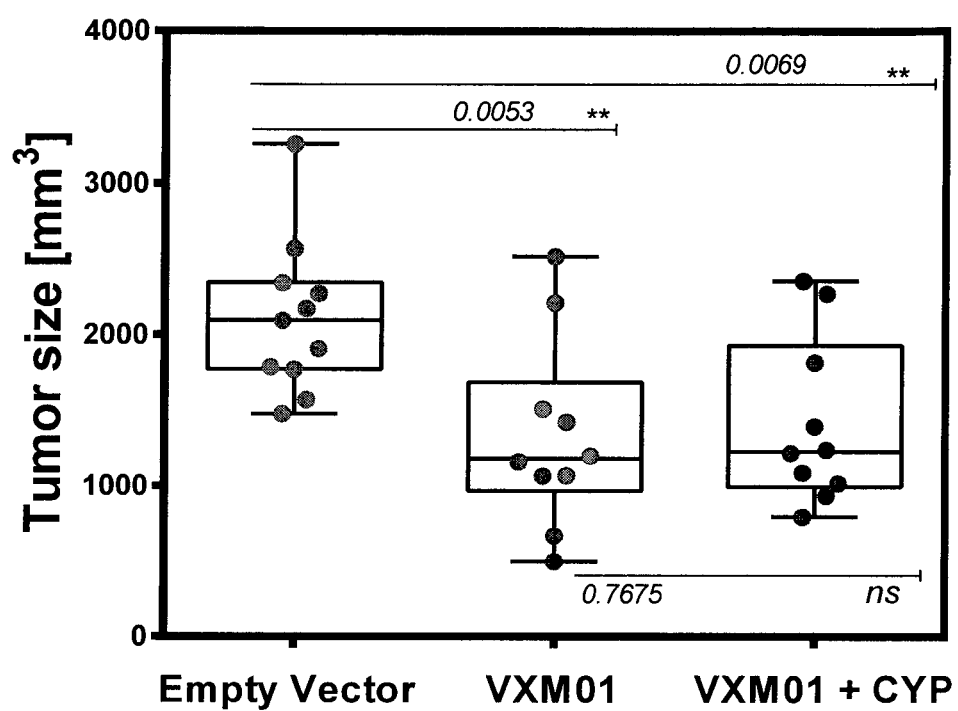

FIG. 27: Effect of VXM01 treatment either with or without cyclophosphamide on tumor size [mm$^3$] on day 30. Each dot represents the result of the tumor of one animal.

Figure 28:
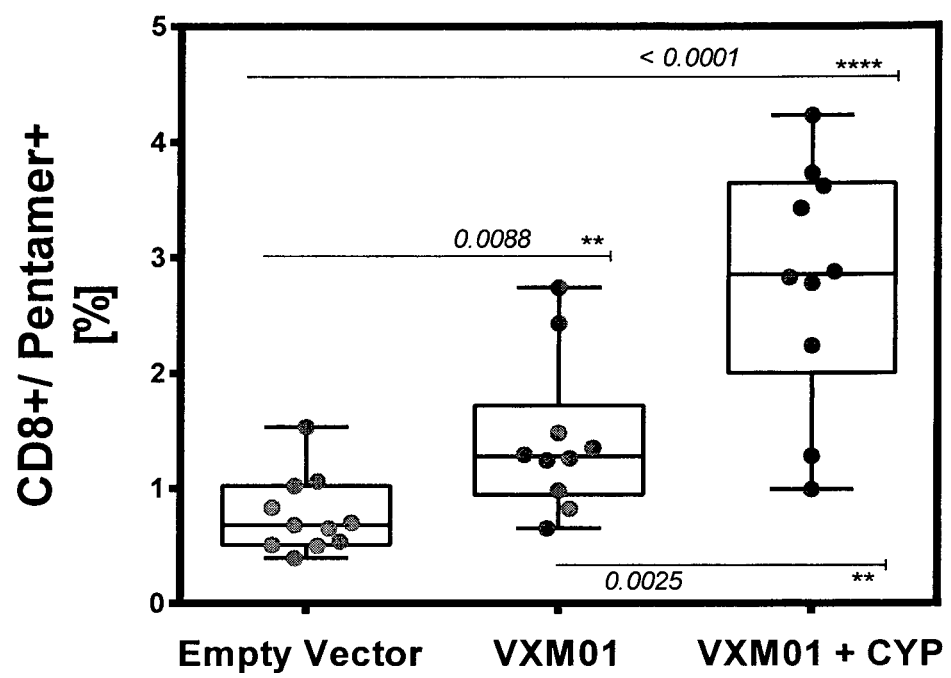

FIG. 28: Percentages of VEGFR-2-specific CD8$^+$ cells in spleens of BALB/C mice bearing subcutaneous CT26 colon tumor cells. Each dot represents the results of one spleen. The results are given in total % of 3 pooled VEGFR2 pentamers.

Figure 29:
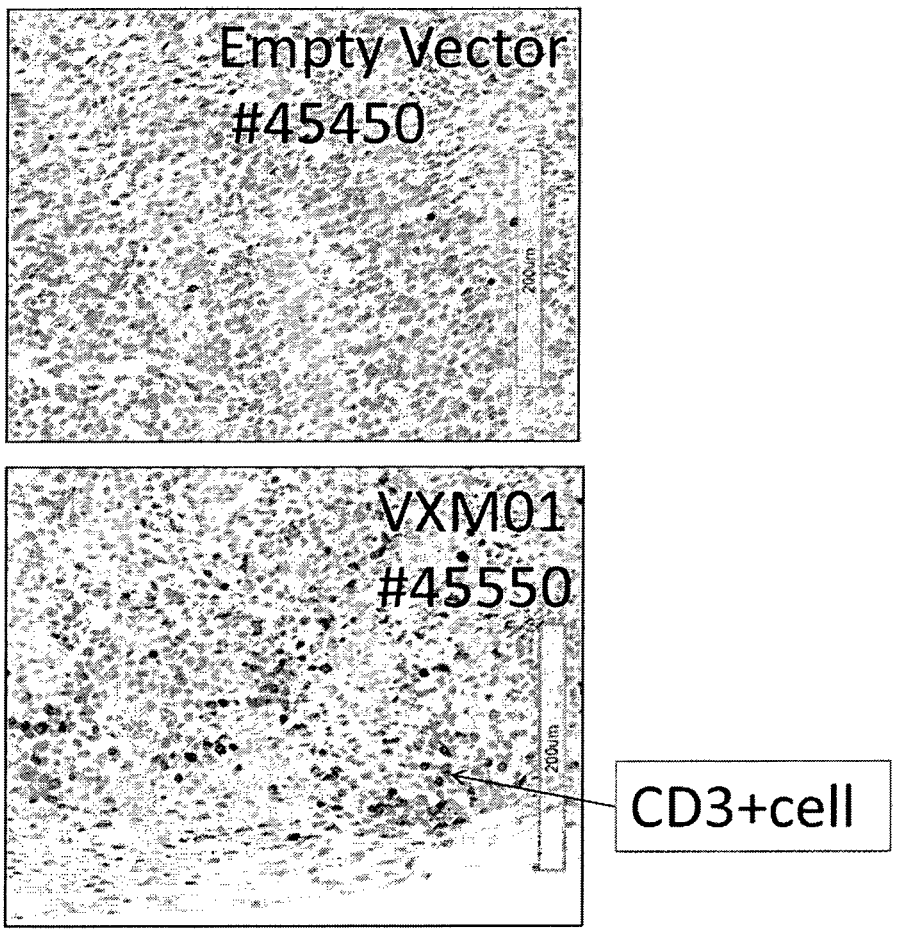

FIG. 29: Anti-CD3 immunohistochemistry staining of tumor samples from animals treated with the empty vector and VXM01, respectively. CD3 positive cells appear in brown color (see arrow for example); ×200 magnification.

Figure 30:
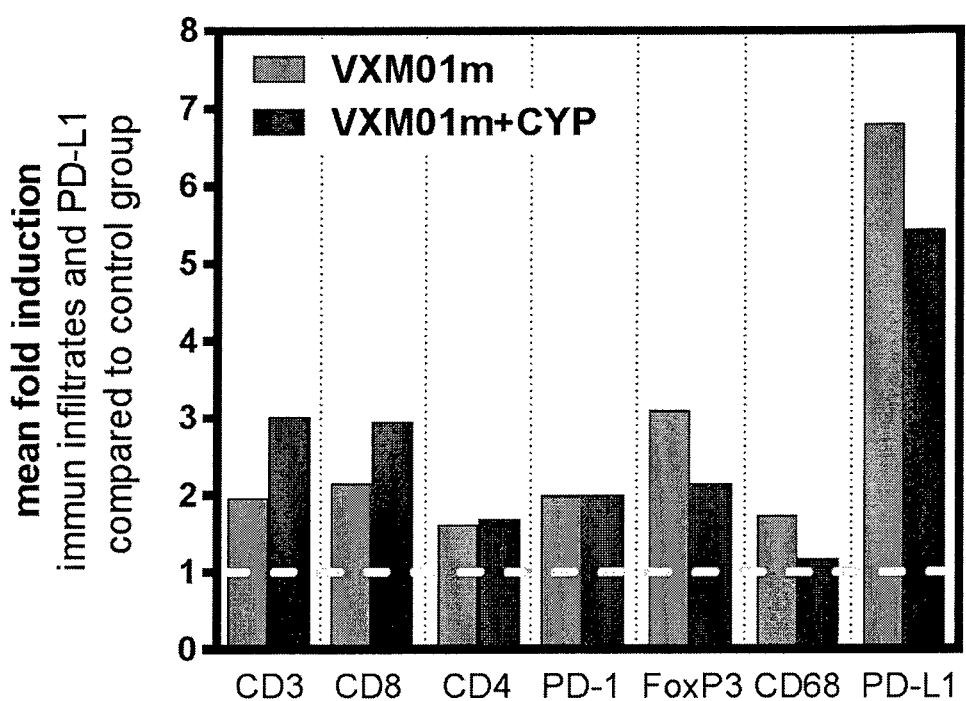

FIG. 30: Quantification of immune cell infiltrates and PD-L1 mean fold induction in tumor samples from animals treated with VXM01 or VXM01 plus cyclophosphamide as compared to animals treated with the empty vector control. Data are derived from absolute cell count/tissue area [mm$^2$]; ×200 magnification.

FIG. 31: Percentages of VEGFR-2- and CEA-specific CD8$^+$ cells in spleens of healthy mice treated with mice bearing subcutaneous CT26 colon tumor cells. Each dot represents the results of one spleen. The results are given in total % of 2 pooled VEGFR2 pentamers.

EXAMPLES

Example 1: MC38 Colon Carcinoma Anti-CTLA4 Combination Study

Four groups of C57/Bl6/6J mice (n=6 each) were challenged with a subcutaneous administration of 5×10$^5$ MC38 tumor cells on Day 0 of the study.

The animals were treated with VXM01mlow (*Salmonella typhimurium* carrying a murine VEGFR-2-encoding eukaryotic expression cassette, manufactured by Richter-Helm BioLogics, Hannover, Germany) alone at a dose of 10$^8$ CFU via oral gavage on Day −1, Day 1, Day 4, and Day 6 (n=6), or with VXM01mlow at the same dose, route of administration, and administration scheme plus the murine anti-CTLA4 antibody on Day 12, 14, 16, and 18 (n=6), or with the murine antiCTLA4-antibody on Day 12, 14, 16, and 18 alone (n=6), or without treatment (n=6, control).

Tumor growth was measured using a micro-caliper. Animals were sacrificed as soon as tumor volume reached 1500 mm$^3$ for animal welfare reasons.

Survival of test animals was recorded once daily.

Tumor growth is graphically depicted in FIG. 23.

Figure 24:
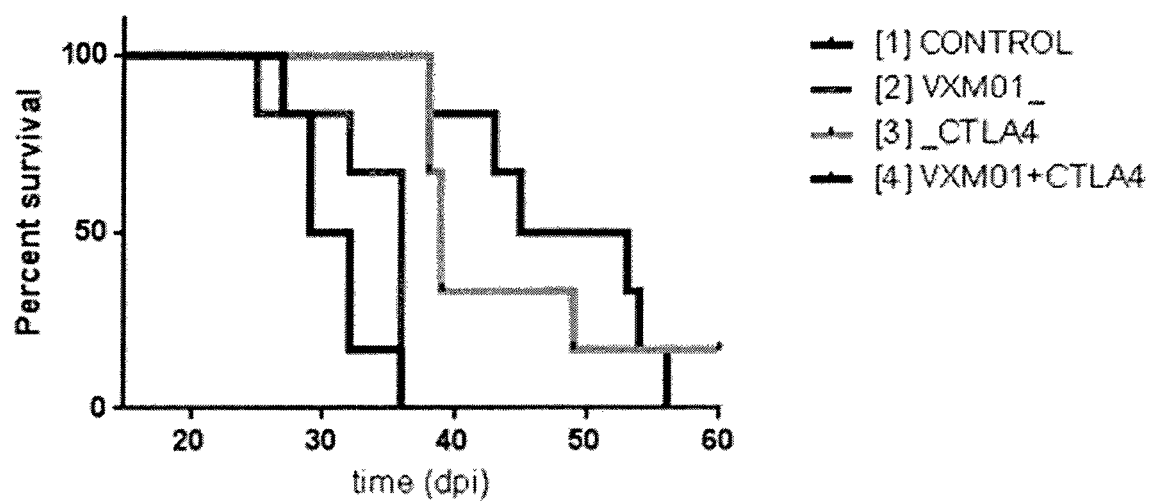

Survival of test animals is displayed in a Kaplan-Meier plot in FIG. 24.

Example 2: B16-F10 Melanoma Anti-CTLA4 Combination Study

Four groups of C57/Bl6/6J mice (n=6 each) were challenged with an intravenous administration of 2×10$^5$ B16-F10 tumor cells on Day 0 of the study.

The animals were treated with VXM01mlow (*Salmonella typhimurium* carrying a murine VEGFR-2-encoding eukaryotic expression cassette, manufactured by Richter-Helm BioLogics, Hannover, Germany) alone at a dose of 10$^8$ CFU via oral gavage on Day −5, Day −3, Day 0, and Day 2 (n=6), or with VXM01mlow at the same dose, route of administration, and administration scheme plus the murine anti-CTLA4 antibody on Day 8, 10, 12, and 14 (n=6), or with the murine antiCTLA4-antibody on Day 8, 10, 12, and 14 alone (n=6), or without treatment (n=6, control).

Survival of test animals was recorded once daily.

Figure 25:
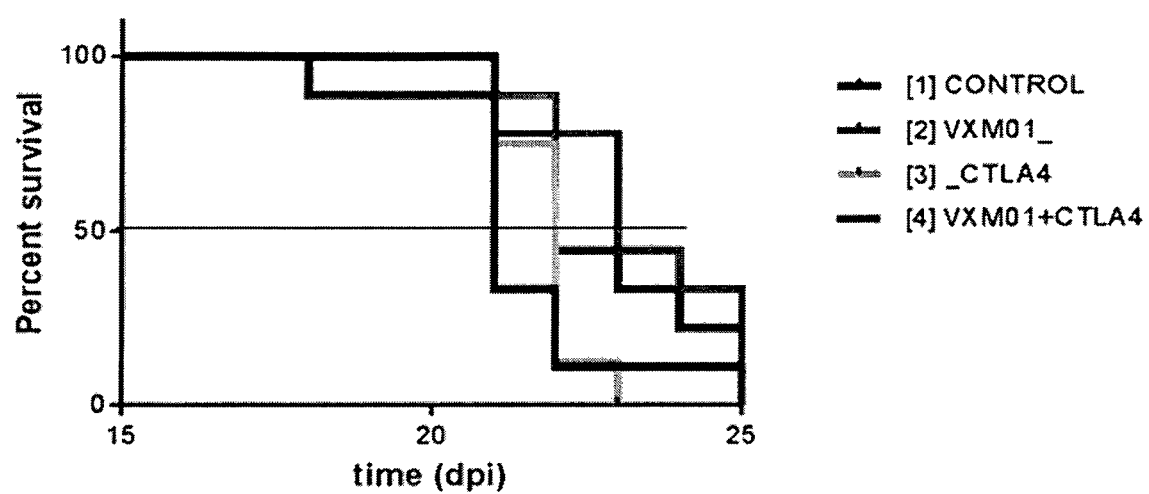

Survival of test animals is displayed in a Kaplan-Meier plot in FIG. 25.

Example 3: Antitumor Activity of VMX01 Vaccine in CT26 Murine Tumor Model

The aim of this study was to evaluate the antitumor activity of VXM01 with or without cyclophosphamide in BALB/C mice bearing subcutaneous CT26 colon tumors, and to characterize the immune responses elicited by the treatments in spleen and tumor.

Control VXM0m-empty (*S. typhimurium* vector control with no expression plasmid) and VXM01mlow (*Salmonella typhimurium* carrying a murine VEGFR-2-encoding eukaryotic expression cassette) were administered at 10$^8$ CFU/adm by oral gavage (per os, PO) via a gavage tube. Regardless of animal groups, each animal received pre-dose application buffer PO to neutralize acid in the stomach prior dosing (100 µl/animal/application). This buffer was composed by dissolution of 2.6 g sodium hydrogen carbonate, 1.7 g L-ascorbic acid and 0.2 g lactose monohydrate in 100 ml of drinking water and was applied within 30 min prior application of VXM0m-empty or VXM01mlow.

Cyclophosphamide was injected at 100 mg/kg/adm into the peritoneal cavity of mice (intraperitoneally, IP). The IP injection volume did not exceed 10 ml/kg and was calculated according to the most recent body weight of mice.

The treatment started at day 0 (D0), one day after randomization that was considered as day −1 (D−1). 33 healthy female BALB/C (BALB/CByJ) mice, 6 weeks old, were randomized according to their body weight into 4 groups of 11 animals each using Vivo Manager® software (Biosystemes, Couternon, France). A statistical test (analysis of variance) was performed to test for homogeneity between groups.

The treatment schedule was as follows:

Group 1: The animals from group 1 received a total of 6 PO administrations of VXM0m-empty on D1, D3, D5, D7, D14 and D21.

Group 2: The animals of group 2 received a total of 6 PO administrations of VXM01mlow on D1, D3, D5, D7, D14 and D21.

Group 3: The animals of group 3 received one single IP injection of cyclophosphamide on D0 and a total of 6 PO administrations of VXM01mlow on D1, D3, D5, D7, D14 and D21.

Figure 26:
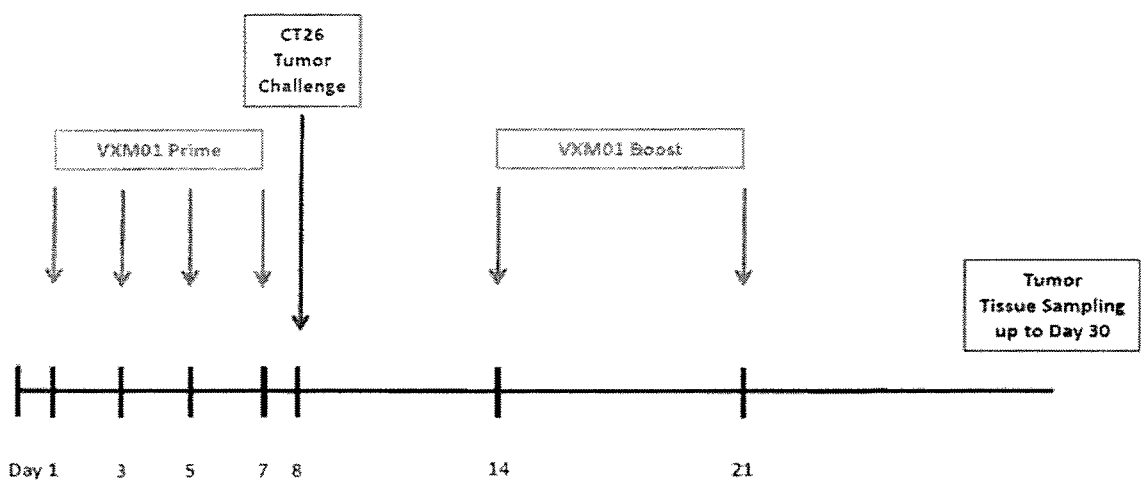

The treatment schedule is summarized in Table 1 and FIG. 26.

TABLE 1

Treatment Schedule

| Group | No. Animals | Treatment | Dose | Route | Treatment Schedule |
|---|---|---|---|---|---|
| 1* | 11 | Empty vector | $10^8$ CFU/adm | PO | D1, D3, D5, D7, D14 and D21 |
| 2* | 11 | VXM01mlow | $10^8$ CFU/adm | PO | D1, D3, D5, D7, D14 and D21 |
| 3* | 11 | VXM01mlow | $10^8$ CFU/adm | PO | D1, D3, D5, D7, D14 and D21 |
|  |  | Cyclophosphamide | 100 mg/kg/adm | IP | D0 |
| TOTAL | 33 |  |  |  |  |

*Each animal received pre-dose application buffer per os (PO) to neutralize acid in the stomach prior dosing Tumors were induced by subcutaneous injection of 1×10$^6$ of CT26 cells in 200 µl of RPMI 1640 into the right flank of the test animals on day 8 (D8).

On the day of termination (D30, i.e. 22 days after tumor inoculation), tumors from all mice were collected and tumor size was measured.

The results are graphically depicted in FIG. 27. Tumor size was significantly decreased in animals treated with either VXM01 alone or VXM01 plus cyclophosphamide as compared to the empty vector control. Tumor size reduction was most pronounced in the animals treated with both cyclophosphamide and the VXM01 vaccine.

On the day of termination, spleens were collected from all mice (11 samples per group) and placed individually into tubes containing chilled PBS (2-8° C.). Immunomonitoring of VEGFR-2 specific T-cell responses using flow cytometry with pentamers was performed.

For this purpose, the spleen samples were washed with PBS and subsequently homogenized by plunging them through a 100 µm nylon cell strainer. During homogenization, the strainer was rinsed several times with cool sterile PBS. The samples were centrifuged at 1500 rpm for 10 minutes at 2-8° C., the supernatant was discarded and the cell pellet was resuspended in 2 ml ACK red blood cell lysis buffer (1 ml buffer per spleen). The cells were incubated in the lysis buffer for 1 min at RT. Then, PBS was added to 40 ml to stop the lysis and the cell suspension was sieved through a fresh strainer (40 µm) and the flow through was collected in a new 50 ml tube. After centrifugation at 1500 rpm for 10 min at 2-8° C. the supernatant was discarded and the pellet was resuspended in 5 ml Il-2 supplemented DMEM medium. The cells were incubated overnight at 37° C. and 5% CO$_2$.

Prior to pentamer staining, a live/dead (L/D) staining using the Live Dead (L/D) Fixable Yellow Dead Cell Stain Kit by Invitrogen was performed according to the manufacturer's instructions, in order to exclude dead cells by gating on negative population.

Pentamer staining was performed using Pro5® Recombinant MHC Pentamers by Proimmune, Oxford, UK, according to the manufacturer's instructions.

The following KDR (VEGFR-2) pentamers were used:

| H-2Kd | - | SYQYGTMQTL | KDR-STL | (SEQ ID NO: 16) |
| H-2Kd | - | KYLSYPAPDI | KDR-KDI | (SEQ ID NO: 17) |
| H-2Kd | - | RFVPDGNRI | KDR-RRI | (SEQ ID NO: 18) |

-continued

| H-2Kd | - | TYQSIMYIV | KDR-TIV | (SEQ ID NO: 19) |
| H-2Kd | - | DFLTLEHLI | KDR-DLI | (SEQ ID NO: 20) |

The results of the pentamer staining are shown in FIG. 28.

The number of VEGFR-2 specific CD8$^+$ cytotoxic T-cells was significantly increased in animals treated with either VXM01 alone or VXM01 plus cyclophosphamide as compared to the empty vector control. The cyclophosphamide treatment together with VXM01 significantly increased the KDR pentamer response as compared to the response obtained with the vaccine VXM01 alone.

Tumors from 5 mice in each group were analyzed by immunohistochemistry (IHC).

For that purpose, the tumors were fixed in 10% neutral buffered formalin for 24 h to 48 h, transferred into ethanol and then embedded in paraffin. The embedded samples were subjected to immunohistochemical staining. The results are graphically depicted in FIGS. 29 and 30.

The mean number of T-cells per unit of tissue are was found to be increased in the tumors of mice treated with either VXM01 alone or VXM01 plus cyclophosphamide as compared to the empty vector control. CD3$^+$ and CD8$^+$ cell populations were found to be increased approximately three-fold in the tumor samples of mice treated with VXM01 plus cyclophosphamide and approximately two-fold in tumor samples of mice treated with VXM01 alone. Also the CD4$^+$ T-cell population was increased in VXM01 vaccine treated animals with and without cyclophosphamide pretreatment, with a 1.7 fold increase in the mean number of CD4$^+$ cells/tissue area in both vaccine groups as compared to the empty vector control.

Furthermore, the number of PD-1 positive immune cells was increased by a factor of 2.0 and 2.1 and the tumor was enriched in PD-L1-expressing cells' upon treatment with VXM01 either as single agent or in combination with cyclophosphamide, clearly indicating that VXM01 treatment might increase the susceptibility of tumors towards the treatment with anti-PD-1 and anti-PD-L1 checkpoint inhibitors.

Example 4: VXM01/VXM08 Combination Study in Healthy C56BL/6J Mice

The aim of this study was to evaluate the capability of VXM01mlow and VXM08hm to trigger an immune response in healthy mice.

Control VXM0m-empty (*S. typhimurium* vector control with no expression plasmid), vaccine VXM01mlow (*Salmonella typhimurium* harboring a murine VEGFR-2-encoding eukaryotic expression cassette) and vaccine VXM08hm (*Salmonella typhimurium* harboring a human CEA encoding eukaryotic expression cassette) were administered at $10^8$ CFU/adm in 50 µl per application by oral gavage (per os, PO) via a gavage tube. Regardless of animal groups, each animal received pre-dose application buffer PO to neutralize acid in the stomach prior dosing (50 µl/animal/application prior to single vaccine administration; 100 µl/animal/application prior to combined administration of VXM01 and VXM08). This buffer was composed by dissolution of 2.6 g sodium hydrogen carbonate, 1.7 g L-ascorbic acid and 0.2 g lactose monohydrate in 100 ml of drinking water and was applied within 30 min prior application of VXM0m-empty, VXM01mlow and/or VXM08hm.

40 healthy female C57BL/6J mice, 6-7 weeks old, were randomized on day 0 (D0) according to their body weight into 5 groups of 8 animals each using Vivo Manager® software (Biosystemes, Couternon, France). A statistical test (analysis of variance) was performed to test for homogeneity between groups.

The treatment schedule was as follows:

Group 1: The animals from group 1 received a total of 6 PO administrations of VXM0m-empty on D1, D3, D5, D7, D14 and D21.

Group 2: The animals of group 2 received a total of 6 PO administrations of VXM01mlow on D1, D3, D5, D7, D14 and D21.

Group 3: The animals of group 3 received a total of 6 PO administrations of VXM08hm on D2, D4, D6, D8, D15 and D22.

Group 4: The animals of group 4 received a total of 6 PO administrations of VXM01mlow on D2, D4, D6, D8, D15 and D22 and a total of 6 PO administrations of VXM08hm on D2, D4, D6, D8, D15 and D22.

Group 5: The animals of group 5 received a total of 6 PO administrations of VXM01mlow on D1, D3, D5, D7, D14 and D21 and a total of 6 PO administrations of VXM08hm on D2, D4, D6, D8, D15 and D22.

The treatment schedule is summarized in Table 2.

On the day of termination (i.e. D29), spleens were collected from all mice (8 samples per group) and placed individually into tubes containing chilled PBS (2-8° C.). Immunomonitoring of VEGFR-2 and CEA specific T-cell responses using flow cytometry with pentamers was performed. Pentamer analysis including preceding live/dead staining was performed as described in Example 3.

The following KDR (VEGFR-2) pentamers were used as a pool mix at same ratio:

```
H-2Db-VILTNPISM      KDR2      (SEQ ID NO: 21)

H-2Db-FSNSTNDILI     KDR3      (SEQ ID NO: 22)
```

The following CEA pentamers were used as a pool mix at same ratio:

```
H-2Db-CGIQNSVSA      CEA-CSA-Penta    (SEQ ID NO: 23)

H-2Db-LQLSNGNRTL     CEA-LTL-Penta    (SEQ ID NO: 24)

H-2Db-CGIQNKLSV      CEA-CSV-Penta    (SEQ ID NO: 25)
```

The results of the pentamer staining are shown in FIG. 31. The mean frequency of VEGFR-2 (KDR) specific $CD8^+$ T-cells was 1.71, 4.36 and 2.76-fold higher in mice treated with VXM01mlow, VXM01mlow/VXM08hm (concomitant) and VXM01mlow/VXM08hm (alternate days) respectively than in the control group. Mice treated with VXM01mlow/VXM08hm either concomitantly or on alternate days showed a higher frequency of VEGFR-2 specific $CD8^+$ T-cells as compared to mice treated with VXM01mlow alone. Although not statistically significant, the synergy was slightly higher when VXM01mlow and VXM08hm vaccine had been applied concomitantly, i.e. the same day as compared to the alternate day regimen.

The mean frequency of CEA-specific $CD8^+$ T-cells was 1.29, 2.23 and 1.95-fold higher in mice treated with VXM08hm, VXM01mlowNXM08hm (concomitant) and VXM01mlowNXM08hm (alternate days) respectively than in the control group. Mice treated with VXM01mlow/VXM08hm either concomitantly or on alternate days showed a higher frequency of CEA specific $CD8^+$ T-cells as compared to mice treated with VXM08hm alone. Although not statistically significant, the synergy was slightly higher when VXM01mlow and VXM08hm vaccine had been applied concomitantly, i.e. the same day as compared to the alternate day regimen.

| Group | No. Mice | Treatment | Dose (CFU/adm) | Volume (µl) | Route | Treatment Schedule |
|---|---|---|---|---|---|---|
| 1 | 8 | Empty vector | | 50 | PO | Prime: D1, D3, D5, D7 Boost: D14, D21 |
| 2 | 8 | VXM01mlow | $10^8$ | 50 | PO | Prime: D1, D3, D5, D7 Boost: D14, D21 |
| 3 | 8 | VXM08hm | $10^8$ | 50 | PO | Prime: D2, D4, D6, D8 Boost: D15, D22 |
| 4 | 8 | VXM01mlow | $10^8$ | 50 | PO | Prime: D2, D4, D6, D8 Boost: D15 and D22 |
| | | VXM08hm* (concomitant) | $10^8$ | 50 | PO | Prime: D2, D4, D6, D8 Boost: D15, D22 |
| 5 | 8 | VXM01mlow | $10^8$ | 50 | PO | Prime: D1, D3, D5, D7 Boost: D14, D21 |
| | | VXM08hm (alternate days) | $10^8$ | 50 | PO | Prime: D2, D4, D6, D8 Boost: D15, D22 |

*VXM08 was administered just after VMX01, at the same day of application

The invention claimed is:

1. A method of treating a human patient against cancer comprising orally administering to the patient a composition comprising a therapeutically effective dose of an attenuated strain of *Salmonella* comprising at least one copy of a DNA molecule comprising an eukaryotic expression cassette encoding a vascular endothelial growth factor receptor-2 (VEGFR-2) comprising the amino acid sequence of SEQ ID NO: 1, wherein the treatment further comprises administering an antibody against CTLA4, wherein the attenuated strain of *Salmonella* is *Salmonella typhi* Ty21a, wherein the therapeutically effective dose of the attenuated strain of the *Salmonella* comprises about $10^6$ to about $10^9$ colony forming units (CFU) and wherein the cancer is a solid tumor.

2. The method of claim 1, wherein the DNA molecule comprises a kanamycin antibiotic resistance gene, a pMB1 ori, and a CMV promoter.

3. The method of claim 1, wherein the attenuated *Salmonella typhi* Ty21a is administered simultaneously with or prior to the administration of the antibody against CTLA4.

4. The method of claim 1, wherein the treatment is accompanied by chemotherapy or radiotherapy.

5. The method of claim 1, wherein the method further comprises assessing the expression pattern of a tumor antigen of said cancer in said patient and/or assessing the pre-immune response against said tumor antigen in said patient.

6. The method of claim 1, wherein the DNA molecule comprises the DNA sequence as set forth in SEQ ID NO: 2.

7. The method of claim 1, wherein the cancer is colon carcinoma or melanoma.

8. The method of claim 1, wherein the oral administration comprises a single administration or multiple administrations of the composition.

* * * * *

SEQUENCE LISTING

<160> NUMBER OF SEQ ID NOS: 25

<210> SEQ ID NO 1
<211> LENGTH: 1356
<212> TYPE: PRT
<213> ORGANISM: human

<400> SEQUENCE: 1

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365
```

-continued

```
Ile Pro Leu Glu Ser Asn His Thr Ile Lys Ala Gly His Val Leu Thr
    370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
            420                 425                 430
Asp Ser Tyr Gln Tyr Gly Thr Thr Gln Thr Leu Thr Cys Thr Val Tyr
        435                 440                 445
Ala Ile Pro Pro Pro His His Ile His Trp Tyr Trp Gln Leu Glu Glu
    450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
            500                 505                 510
Thr Val Ser Thr Leu Val Ile Gln Ala Ala Asn Val Ser Ala Leu Tyr
        515                 520                 525
Lys Cys Glu Ala Val Asn Lys Val Gly Arg Gly Glu Arg Val Ile Ser
    530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
            580                 585                 590
Ile His Val Gly Glu Leu Pro Thr Pro Val Cys Lys Asn Leu Asp Thr
        595                 600                 605
Leu Trp Lys Leu Asn Ala Thr Met Phe Ser Asn Ser Thr Asn Asp Ile
    610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
            660                 665                 670
Leu Glu Asn Gln Thr Thr Ser Ile Gly Glu Ser Ile Glu Val Ser Cys
        675                 680                 685
Thr Ala Ser Gly Asn Pro Pro Pro Gln Ile Met Trp Phe Lys Asp Asn
    690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
            740                 745                 750
Ile Ile Glu Gly Ala Gln Glu Lys Thr Asn Leu Glu Ile Ile Leu
        755                 760                 765
Val Gly Thr Ala Val Ile Ala Met Phe Phe Trp Leu Leu Leu Val Ile
    770                 775                 780
Ile Leu Arg Thr Val Lys Arg Ala Asn Gly Gly Glu Leu Lys Thr Gly
```

```
              785                 790                 795                 800
          Tyr Leu Ser Ile Val Met Asp Pro Asp Glu Leu Pro Leu Asp Glu His
                              805                 810                 815

Cys Glu Arg Leu Pro Tyr Asp Ala Ser Lys Trp Glu Phe Pro Arg Asp
                              820                 825                 830

Arg Leu Lys Leu Gly Lys Pro Leu Gly Arg Gly Ala Phe Gly Gln Val
                              835                 840                 845

Ile Glu Ala Asp Ala Phe Gly Ile Asp Lys Thr Ala Thr Cys Arg Thr
                  850                 855                 860

Val Ala Val Lys Met Leu Lys Glu Gly Ala Thr His Ser Glu His Arg
          865                 870                 875                 880

Ala Leu Met Ser Glu Leu Lys Ile Leu Ile His Ile Gly His His Leu
                              885                 890                 895

Asn Val Val Asn Leu Leu Gly Ala Cys Thr Lys Pro Gly Gly Pro Leu
                          900                 905                 910

Met Val Ile Val Glu Phe Cys Lys Phe Gly Asn Leu Ser Thr Tyr Leu
                          915                 920                 925

Arg Ser Lys Arg Asn Glu Phe Val Pro Tyr Lys Thr Lys Gly Ala Arg
                  930                 935                 940

Phe Arg Gln Gly Lys Asp Tyr Val Gly Ala Ile Pro Val Asp Leu Lys
          945                 950                 955                 960

Arg Arg Leu Asp Ser Ile Thr Ser Ser Gln Ser Ser Ala Ser Ser Gly
                              965                 970                 975

Phe Val Glu Glu Lys Ser Leu Ser Asp Val Glu Glu Glu Glu Ala Pro
                          980                 985                 990

Glu Asp Leu Tyr Lys Asp Phe Leu  Thr Leu Glu His Leu  Ile Cys Tyr
                          995                 1000                1005

Ser Phe  Gln Val Ala Lys Gly  Met Glu Phe Leu Ala  Ser Arg Lys
                          1010                1015                1020

Cys Ile  His Arg Asp Leu Ala  Ala Arg Asn Ile Leu  Leu Ser Glu
                          1025                1030                1035

Lys Asn  Val Val Lys Ile Cys  Asp Phe Gly Leu Ala  Arg Asp Ile
                          1040                1045                1050

Tyr Lys  Asp Pro Asp Tyr Val  Arg Lys Gly Asp Ala  Arg Leu Pro
                          1055                1060                1065

Leu Lys  Trp Met Ala Pro Glu  Thr Ile Phe Asp Arg  Val Tyr Thr
                          1070                1075                1080

Ile Gln  Ser Asp Val Trp Ser  Phe Gly Val Leu Leu  Trp Glu Ile
                          1085                1090                1095

Phe Ser  Leu Gly Ala Ser Pro  Tyr Pro Gly Val Lys  Ile Asp Glu
                          1100                1105                1110

Glu Phe  Cys Arg Arg Leu Lys  Glu Gly Thr Arg Met  Arg Ala Pro
                          1115                1120                1125

Asp Tyr  Thr Thr Pro Glu Met  Tyr Gln Thr Met Leu  Asp Cys Trp
                          1130                1135                1140

His Gly  Glu Pro Ser Gln Arg  Pro Thr Phe Ser Glu  Leu Val Glu
                          1145                1150                1155

His Leu  Gly Asn Leu Leu Gln  Ala Asn Ala Gln Gln  Asp Gly Lys
                          1160                1165                1170

Asp Tyr  Ile Val Leu Pro Ile  Ser Glu Thr Leu Ser  Met Glu Glu
                          1175                1180                1185

Asp Ser  Gly Leu Ser Leu Pro  Thr Ser Pro Val Ser  Cys Met Glu
                          1190                1195                1200
```

```
Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 2
<211> LENGTH: 3500
<212> TYPE: DNA
<213> ORGANISM: artificial
<220> FEATURE:
<223> OTHER INFORMATION: expression plasmid

<400> SEQUENCE: 2
tgggcttttg ctggcctttt gctcacatgt tcttgactct tcgcgatgta cgggccagat      60
atacgcgttg acattgatta ttgactagtt attaatagta atcaattacg gggtcattag     120
ttcatagccc atatatggag ttccgcgtta cataacttac ggtaaatggc ccgcctggct     180
gaccgcccaa cgacccccgc ccattgacgt caataatgac gtatgttccc atagtaacgc     240
caatagggac tttccattga cgtcaatggg tggactattt acggtaaact gcccacttgg     300
cagtacatca agtgtatcat atgccaagta cgccccctat tgacgtcaat gacggtaaat     360
ggcccgcctg gcattatgcc cagtacatga ccttatggga cttttcctact tggcagtaca     420 tctacgtatt agtcatcgct attaccatgg tgatgcggtt ttggcagtac atcaatgggc     480
gtggatagcg gtttgactca cggggatttc caagtctcca ccccattgac gtcaatggga     540
gtttgttttg gcaccaaaat caacgggact ttccaaaatg tcgtaacaac tccgccccat     600
tgacgcaaat gggcggtagg cgtgtacggt gggaggtcta taagcaga gctctctggc     660 taactagaga acccactgct tactggctta tcgaaattaa tacgactcac tatagggaga     720
cccaagctgg ctagcctcga gtctagaggg cccgtttaaa cccgctgatc agcctcgact     780
gtgccttcta gttgccagcc atctgttgtt tgccctccc ccgtgccttc cttgaccctg     840
gaaggtgcca ctcccactgt cctttcctaa taaaatgagg aaattgcatc gcattgtctg     900
agtaggtgtc attctattct ggggggtggg gtggggcagg acagcaaggg ggaggattgg     960
gaagacaata gcaggcatgc tggggatgcg gtgggctcta tggcttctac tgggcggttt    1020
tatggacagc aagcgaaccg gaattgccag ctggggcgcc ctctggtaag gttgggaagc    1080
```

```
cctgcaaagt aaactggatg gctttctcgc cgccaaggat ctgatggcgc agggggatcaa   1140 gctctgatca agagacagga tgaggatcgt ttcgcatgat tgaacaagat ggattgcacg   1200
caggttctcc ggccgcttgg gtggagaggc tattcggcta tgactgggca caacagacaa   1260
tcggctgctc tgatgccgcc gtgttccggc tgtcagcgca ggggcgcccg gttcttttg    1320 tcaagaccga cctgtccggt gccctgaatg aactgcaaga cgaggcagcg cggctatcgt   1380
ggctggccac gacgggcgtt ccttgcgcag ctgtgctcga cgttgtcact gaagcgggaa   1440
gggactggct gctattgggc gaagtgccgg ggcaggatct cctgtcatct caccttgctc   1500
ctgccgagaa agtatccatc atggctgatg caatgcggcg gctgcatacg cttgatccgg   1560
ctacctgccc attcgaccac caagcgaaac atcgcatcga gcgagcacgt actcggatgg   1620
aagccggtct tgtcgatcag gatgatctgg acgaagagca tcaggggctc gcgccagccg   1680
aactgttcgc caggctcaag gcgagcatgc ccgacggcga ggatctcgtc gtgacccatg   1740
gcgatgcctg cttgccgaat atcatggtgg aaaatggccg cttttctgga ttcatcgact   1800
gtggccggct gggtgtggcg gaccgctatc aggacatagc gttggctacc cgtgatattg   1860
ctgaagagct tggcggcgaa tgggctgacc gcttcctcgt gctttacggt atcgccgctc   1920
ccgattcgca gcgcatcgcc ttctatcgcc ttcttgacga gttcttctga attattaacg   1980
cttacaattt cctgatgcgg tattttctcc ttacgcatct gtgcggtatt tcacaccgca   2040
tacaggtggc acttttcggg gaaatgtgcg cggaacccct atttgtttat ttttctaaat   2100
acattcaaat atgtatccgc tcatgagaca ataaccctga taaatgcttc aataatagca   2160
cgtgctaaaa cttcattttt aatttaaaag gatctaggtg aagatccttt ttgataatct   2220
catgaccaaa atcccttaac gtgagttttc gttccactga gcgtcagacc ccatcagtg    2280 accaaacagg aaaaaaccgc ccttaacatg cccgctttta tcagaagcca gacattaacg   2340
cttctggaga aactcaacga gctggacgcg gatgaacagg cagacatctg tgaatcgctt   2400
cacgaccacg ctgatgagct ttaccgcagc tgcctcgcgc gtttcggtga tgacggtgaa   2460
aacctctgac acatgcagct cccggagacg gtcacagctt gtctgtaagc ggatgccggg   2520
agcagacaag cccgtcaggg cgcgtcagcg ggtgttggcg ggtgtcgggg cgcagccatg   2580
acccagtcac gtagcgatag cggagtgtat actggcttaa ctatgcggca tcagagcaga   2640
ttgtactgag agtgcaccat atgcggtgtg aaataccgca cagatgcgta aggagaaaat   2700
accgcatcag gcgctcttcc gcttcctcgc tcactgactc gctgcgctcg gtcgttcggc   2760
tgcggcgagc ggtatcagct cactcaaagg cggtaatacg ttatccaca gaatcagggg    2820 ataacgcagg aaagaacatg tgagcaaaag gccagcaaaa ggccaggaac cgtaaaaagg   2880
ccgcgttgct ggcgtttttc cataggctcc gcccccctga cgagcatcac aaaaatcgac   2940
gctcaagtca gaggtggcga aacccgacag gactataaag ataccaggcg tttccccctg   3000
gaagctccct cgtgcgctct cctgttccga cctgccgct taccggatac ctgtccgcct    3060
ttctcccttc gggaagcgtg gcgctttctc atagctcacg ctgtaggtat ctcagttcgg   3120
tgtaggtcgt tcgctccaag ctgggctgtg tgcacgaacc ccccgttcag cccgaccgct   3180
gcgccttatc cggtaactat cgtcttgagt ccaacccggt aagacacgac ttatcgccac   3240
tggcagcagc cactggtaac aggattagca gagcgaggta tgtaggcggt gctacagagt   3300
tcttgaagtg gtggcctaac tacggctaca ctagaaggac agtatttggt atctgcgctc   3360
tgctgaagcc agttaccttc ggaaaaagag ttggtagctc ttgatccggc aaacaaacca   3420
```

-continued

```
ccgctggtag cggtggtttt tttgtttgca agcagcagat tacgcgcaga aaaaaggat    3480 ctcaagaaga tcctttgatc                                              3500
```

<210> SEQ ID NO 3
<211> LENGTH: 371
<212> TYPE: PRT
<213> ORGANISM: human

<400> SEQUENCE: 3

```
Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
```

355                 360                 365

Gln Leu Lys
    370

<210> SEQ ID NO 4
<211> LENGTH: 630
<212> TYPE: PRT
<213> ORGANISM: human

<400> SEQUENCE: 4

Met Ala Leu Pro Thr Ala Arg Pro Leu Leu Gly Ser Cys Gly Thr Pro
1               5                   10                  15

Ala Leu Gly Ser Leu Leu Phe Leu Phe Ser Leu Gly Trp Val Gln
            20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
            355                 360                 365

Ile Gln His Leu Gly Tyr Leu Phe Leu Lys Met Ser Pro Glu Asp Ile
        370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630

<210> SEQ ID NO 5
<211> LENGTH: 702
<212> TYPE: PRT
<213> ORGANISM: human

<400> SEQUENCE: 5

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
                20                  25                  30

Thr Ala Lys Leu Thr Ile Glu Ser Thr Pro Phe Asn Val Ala Glu Gly
            35                  40                  45

Lys Glu Val Leu Leu Leu Val His Asn Leu Pro Gln His Leu Phe Gly
        50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

```
Gly Arg Glu Ile Ile Tyr Pro Asn Ala Ser Leu Leu Ile Gln Asn Ile
                100                 105                 110

Ile Gln Asn Asp Thr Gly Phe Tyr Thr Leu His Val Ile Lys Ser Asp
            115                 120                 125

Leu Val Asn Glu Glu Ala Thr Gly Gln Phe Arg Val Tyr Pro Glu Leu
        130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510
```

Val Glu Asp Lys Asp Ala Val Ala Phe Thr Cys Glu Pro Glu Ala Gln
515                 520                 525

Asn Thr Thr Tyr Leu Trp Trp Val Asn Gly Gln Ser Leu Pro Val Ser
530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
                580                 585                 590

Pro Asp Thr Pro Ile Ile Ser Pro Pro Asp Ser Ser Tyr Leu Ser Gly
                595                 600                 605

Ala Asn Leu Asn Leu Ser Cys His Ser Ala Ser Asn Pro Ser Pro Gln
610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
                660                 665                 670

Thr Val Ser Ala Ser Gly Thr Ser Pro Gly Leu Ser Ala Gly Ala Thr
675                 680                 685

Val Gly Ile Met Ile Gly Val Leu Val Gly Val Ala Leu Ile
                690                 695                 700

<210> SEQ ID NO 6
<211> LENGTH: 561
<212> TYPE: PRT
<213> ORGANISM: CMV

<400> SEQUENCE: 6

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
                20                  25                  30

Pro Val Leu Pro His Glu Thr Arg Leu Leu Gln Thr Gly Ile His Val
                35                  40                  45

Arg Val Ser Gln Pro Ser Leu Ile Leu Val Ser Gln Tyr Thr Pro Asp
                50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
                100                 105                 110

Val Tyr Ala Leu Pro Leu Lys Met Leu Asn Ile Pro Ser Ile Asn Val
                115                 120                 125

His His Tyr Pro Ser Ala Ala Glu Arg Lys His Arg His Leu Pro Val
130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
                180                 185                 190

-continued

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
            420                 425                 430

Ala Gly Arg Lys Arg Lys Ser Ala Ser Ser Ala Thr Ala Cys Thr Ala
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly

<210> SEQ ID NO 7
<211> LENGTH: 561
<212> TYPE: PRT
<213> ORGANISM: artificial
<220> FEATURE:
<223> OTHER INFORMATION: mutated CMV pp65

<400> SEQUENCE: 7

```
Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
                20                  25                  30

Pro Val Leu Pro His Glu Thr Arg Leu Leu Gln Thr Gly Ile His Val
            35                  40                  45

Arg Val Ser Gln Pro Ser Leu Ile Leu Val Ser Gln Tyr Thr Pro Asp
        50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
                100                 105                 110

Val Tyr Ala Leu Pro Leu Lys Met Leu Asn Ile Pro Ser Ile Asn Val
            115                 120                 125

His His Tyr Pro Ser Ala Ala Glu Arg Lys His Arg His Leu Pro Val
130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
                180                 185                 190

Val Ala Leu Arg His Val Val Cys Ala His Glu Leu Val Cys Ser Met
            195                 200                 205

Glu Asn Thr Arg Ala Thr Lys Met Gln Val Ile Gly Asp Gln Tyr Val
            210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
                260                 265                 270

Thr Val Leu Cys Pro Lys Asn Met Ile Ile Lys Pro Gly Lys Ile Ser
            275                 280                 285

His Ile Met Leu Asp Val Ala Phe Thr Ser His Glu His Phe Gly Leu
290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
            355                 360                 365

Phe Thr Ser Gln Tyr Arg Ile Gln Gly Lys Leu Glu Tyr Arg His Thr
            370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
```

```
                    405                 410                 415
Thr Pro Arg Val Thr Gly Gly Ala Met Ala Gly Ser Thr Ser
            420                 425                 430

Ala Gly Arg Asn Arg Lys Ser Ala Ser Ser Thr Ala Cys Thr Ala
            435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
                515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly

<210> SEQ ID NO 8
<211> LENGTH: 536
<212> TYPE: PRT
<213> ORGANISM: artificial
<220> FEATURE:
<223> OTHER INFORMATION: mutated CMV pp65

<400> SEQUENCE: 8

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205
```

```
Glu Asn Thr Arg Ala Thr Lys Met Gln Val Ile Gly Asp Gln Tyr Val
    210                 215                 220
Lys Val Tyr Leu Glu Ser Phe Cys Glu Asp Val Pro Ser Gly Lys Leu
225                 230                 235                 240
Phe Met His Val Thr Leu Gly Ser Asp Val Glu Glu Asp Leu Thr Met
                245                 250                 255
Thr Arg Asn Pro Gln Pro Phe Met Arg Pro His Glu Arg Asn Gly Phe
            260                 265                 270
Thr Val Leu Cys Pro Lys Asn Met Ile Ile Lys Pro Gly Lys Ile Ser
        275                 280                 285
His Ile Met Leu Asp Val Ala Phe Thr Ser His Glu His Phe Gly Leu
    290                 295                 300
Leu Cys Pro Lys Ser Ile Pro Gly Leu Ser Ile Ser Gly Asn Leu Leu
305                 310                 315                 320
Met Asn Gly Gln Gln Ile Phe Leu Glu Val Gln Ala Ile Arg Glu Thr
                325                 330                 335
Val Glu Leu Arg Gln Tyr Asp Pro Val Ala Ala Leu Phe Phe Phe Asp
            340                 345                 350
Ile Asp Leu Leu Leu Gln Arg Gly Pro Gln Tyr Ser Glu His Pro Thr
        355                 360                 365
Phe Thr Ser Gln Tyr Arg Ile Gln Gly Lys Leu Glu Tyr Arg His Thr
    370                 375                 380
Trp Asp Arg His Asp Glu Gly Ala Ala Gln Gly Asp Asp Asp Val Trp
385                 390                 395                 400
Thr Ser Gly Ser Asp Ser Asp Glu Glu Leu Val Thr Thr Glu Arg Lys
                405                 410                 415
Thr Pro Arg Val Thr Gly Gly Gly Ala Met Ala Gly Ala Ser Thr Ser
            420                 425                 430
Ala Gly Arg Asn Arg Lys Ser Ala Ser Ser Ala Thr Ala Cys Thr Ala
        435                 440                 445
Gly Val Met Thr Arg Gly Arg Leu Lys Ala Glu Ser Thr Val Ala Pro
    450                 455                 460
Glu Glu Asp Thr Asp Glu Asp Ser Asp Asn Glu Ile His Asn Pro Ala
465                 470                 475                 480
Val Phe Thr Trp Pro Pro Trp Gln Ala Gly Ile Leu Ala Arg Asn Leu
                485                 490                 495
Val Pro Met Val Ala Thr Val Gln Gly Gln Asn Leu Lys Tyr Gln Glu
            500                 505                 510
Phe Phe Trp Asp Ala Asn Asp Ile Tyr Arg Ile Phe Ala Glu Leu Glu
        515                 520                 525
Gly Val Trp Gln Pro Ala Ala Gln
    530                 535

<210> SEQ ID NO 9
<211> LENGTH: 4071
<212> TYPE: DNA
<213> ORGANISM: human

<400> SEQUENCE: 9
atgcagagca aggtgctgct ggccgtcgcc ctgtggctct gcgtggagac ccgggccgcc      60
tctgtgggtt tgcctagtgt ttctcttgat ctgcccaggc tcagcataca aaaagacata     120
cttacaatta aggctaatac aactcttcaa attacttgca ggggacagag ggacttggac     180
tggctttggc ccaataatca gagtggcagt gagcaagggt ggaggtgact gagtgcagc     240
```

```
gatggcctct tctgtaagac actcacaatt ccaaaagtga tcggaaatga cactggagcc    300
tacaagtgct tctaccggga aactgacttg gcctcggtca tttatgtcta tgttcaagat    360
tacagatctc catttattgc ttctgttagt gaccaacatg gagtcgtgta cattactgag    420
aacaaaaaca aaactgtggt gattccatgt ctcgggtcca tttcaaatct caacgtgtca    480
ctttgtgcaa gatacccaga aaagagattt gttcctgatg gtaacagaat ttcctgggac    540
agcaagaagg gctttactat tcccagctac atgatcagct atgctggcat ggtcttctgt    600
gaagcaaaaa ttaatgatga agttaccag tctattatgt acatagttgt cgttgtaggg    660
tataggattt atgatgtggt tctgagtccg tctcatggaa ttgaactatc tgttggagaa    720
aagcttgtct taaattgtac agcaagaact gaactaaatg tggggattga cttcaactgg    780
gaataccctt cttcgaagca tcagcataag aaacttgtaa accgagacct aaaaacccag    840
tctgggagtg agatgaagaa atttttgagc accttaacta tagatggtgt aacccggagt    900
gaccaaggat tgtacacctg tgcagcatcc agtgggctga tgaccaagaa gaacagcaca    960
tttgtcaggg tccatgaaaa accttttgtt gcttttggaa gtggcatgga atctctggtg   1020
gaagccacgt ggggggagcg tgtcagaatc cctgcgaagt accttggtta cccaccccca   1080
gaaataaaat ggtataaaaa tggaataccc cttgagtcca atcacacaat taaagcgggg   1140
catgtactga cgattatgga agtgagtgaa agagacacag gaaattacac tgtcatcctt   1200
accaatccca tttcaaagga gaagcagagc catgtggtct ctctggttgt gtatgtccca   1260
ccccagattg gtgagaaatc tctaatctct cctgtggatt cctaccagta cggcaccact   1320
caaacgctga catgtacggt ctatgccatt cctcccccgc atcacatcca ctggtattgg   1380
cagttggagg aagagtgcgc caacgagccc agccaagctg tctcagtgac aaacccatac   1440
ccttgtgaag aatggagaag tgtggaggac ttccagggag gaaataaaat tgaagttaat   1500
aaaaatcaat ttgctctaat tgaaggaaaa aacaaaactg taagtaccct tgttatccaa   1560
gcggcaaatg tgtcagcttt gtacaaatgt gaagcggtca acaaagtcgg gagaggagag   1620
agggtgatct ccttccacgt gaccaggggt cctgaaatta cttttgcaacc tgacatgcag   1680 cccactgagc aggagagcgt gtcttttgtgg tgcactgcag acagatctac gtttgagaac   1740
ctcacatggt acaagcttgg cccacagcct ctgccaatcc atgtgggaga gttgcccaca   1800
cctgtttgca agaacttgga tactcttfgg aaattgaatg ccaccatgtt ctctaatagc   1860
acaaatgaca ttttgatcat ggagcttaag aatgcatcct gcaggacca aggagactat   1920 gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
ggggaaagca tcgaagtctc atgcacggca tctgggaatc ccctccaca gatcatgtgg   2100 tttaaagata tgagaccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca ttttttcataa tagaaggtgc ccaggaaaag   2280
acgaacttgg aaatcattat tctagtaggc acggcggtga ttgccatgtt cttctggcta   2340
cttcttgtca tcatcctacg gaccgttaag cgggccaatg gaggggaact gaagacaggc   2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg cctttggcca agtgattgaa gcagatgcct ttggaattga caagacagca   2580
```

| | |
|---|---|
| acttgcagga cagtagcagt caaaatgttg aaagaaggag caacacacag tgagcatcga | 2640 |
| gctctcatgt ctgaactcaa gatcctcatt catattggtc accatctcaa tgtggtcaac | 2700 |
| cttctaggtg cctgtaccaa gccaggaggg ccactcatgg tgattgtgga attctgcaaa | 2760 |
| tttggaaacc tgtccactta cctgaggagc aagagaaatg aatttgtccc ctacaagacc | 2820 |
| aaagggcac gattccgtca agggaaagac tacgttggag caatccctgt ggatctgaaa | 2880 |
| cggcgcttgg acagcatcac cagtagccag agctcagcca gctctggatt tgtggaggag | 2940 |
| aagtccctca gtgatgtaga agaagaggaa gctcctgaag atctgtataa ggacttcctg | 3000 |
| accttggagc atctcatctg ttacagcttc caagtggcta agggcatgga gttcttggca | 3060 |
| tcgcgaaagt gtatccacag ggacctggcg gcacgaaata tcctcttatc ggagaagaac | 3120 |
| gtggttaaaa tctgtgactt tggcttggcc cgggatattt ataaagatcc agattatgtc | 3180 |
| agaaaaggag atgctcgcct ccctttgaaa tggatggccc cagaaacaat ttttgacaga | 3240 |
| gtgtacacaa tccagagtga cgtctggtct tttggtgttt tgctgtggga aatattttcc | 3300 |
| ttaggtgctt ctccatatcc tggggtaaag attgatgaag aattttgtag gcgattgaaa | 3360 |
| gaaggaacta gaatgagggc ccctgattat actacaccag aaatgtacca gaccatgctg | 3420 |
| gactgctggc acgggagcc cagtcagaga cccacgtttt cagagttggt ggaacatttg | 3480 |
| ggaaatctct tgcaagctaa tgctcagcag gatggcaaag actacattgt tcttccgata | 3540 |
| tcagagactt tgagcatgga agaggattct ggactctctc tgcctacctc acctgtttcc | 3600 |
| tgtatggagg aggaggaagt atgtgacccc aaattccatt atgacaacac agcaggaatc | 3660 |
| agtcagtatc tgcagaacag taagcgaaag agccggcctg tgagtgtaaa aacatttgaa | 3720 |
| gatatcccgt tagaagaacc agaagtaaaa gtaatcccag atgacaacca gacggacagt | 3780 |
| ggtatggttc ttgcctcaga agagctgaaa actttggaag acagaaccaa attatctcca | 3840 |
| tcttttggtg gaatggtgcc cagcaaaagc agggagtctg tggcatctga aggctcaaac | 3900 |
| cagacaagcg gctaccagtc cggatatcac tccgatgaca cagacaccac cgtgtactcc | 3960 |
| agtgaggaag cagaactttt aaagctgata gagattggag tgcaaaccgg tagcacagcc | 4020 |
| cagattctcc agcctgactc ggggaccaca ctgagctctc ctcctgttta a | 4071 |

<210> SEQ ID NO 10
<211> LENGTH: 1116
<212> TYPE: DNA
<213> ORGANISM: human

<400> SEQUENCE: 10

| | |
|---|---|
| atggacttcc tcttgctgca ggacccggct tccacgtgtg tcccggagcc ggcgtctcag | 60 |
| cacacgctcc gctccgggcc tgggtgccta cagcagccag agcagcaggg agtccgggac | 120 |
| ccgggcggca tctgggccaa gttaggcgcc gccgaggcca gcgctgaacg tctccagggc | 180 |
| cggaggagcc gcgggcgtc cgggtctgag ccgcagcaaa tggctccga cgtgcgggac | 240 |
| ctgaacgcgc tgctgccgc cgtcccctcc ctgggtggcg gcggcggctg tgccctgcct | 300 |
| gtgagcggcg cggcgcagtg ggcgccggtg ctggactttg cgccccggg cgcttcggct | 360 |
| tacgggtcgt tgggcggccc cgcgccgcca ccggctccgc cgccacccc gccgccgccg | 420 |
| cctcactcct tcatcaaaca ggagccgagc tggggcggcg cggagccgca cgaggagcag | 480 |
| tgcctgagcg ccttcactgt ccacttttcc ggccagttca ctggcacagc cggagcctgt | 540 |
| cgctacgggc ccttcggtcc tcctccgccc agccaggcgc catccggcca ggccaggatg | 600 |
| tttcctaacg cgccctacct gcccagctgc ctggagagcc agcccgctat tcgcaatcag | 660 |

| | | | |
|---|---|---|---|
| ggttacagca | cggtcacctt | cgacgggacg cccagctacg | gtcacacgcc ctcgcaccat | 720 |
| gcggcgcagt | tccccaacca | ctcattcaag catgaggatc | ccatgggcca gcagggctcg | 780 |
| ctgggtgagc | agcagtactc | ggtgccgccc ccggtctatg | ctgccacac ccccaccgac | 840 |
| agctgcaccg | gcagccaggc | tttgctgctg aggacgccct | acagcagtga caatttatac | 900 |
| caaatgacat | cccagcttga | atgcatgacc tggaatcaga | tgaacttagg agccaccta | 960 |
| aagggagttg | ctgctgggag | ctccagctca gtgaaatgga | cagaagggca gagcaaccac | 1020 |
| agcacagggt | acgagagcga | taaccacaca acgcccatcc | tctgcggagc ccaatacaga | 1080 |
| atacacacgc | acggtgtctt | cagaggcatt cagtga | | 1116 |

<210> SEQ ID NO 11
<211> LENGTH: 1893
<212> TYPE: DNA
<213> ORGANISM: human

<400> SEQUENCE: 11

| | | | |
|---|---|---|---|
| atggccttgc | caacggctcg | acccctgttg gggtcctgtg | ggaccccgc cctcggcagc | 60 |
| ctcctgttcc | tgctcttcag | cctcggatgg gtgcagccct | ccaggaccct ggctggagag | 120 |
| acagggcagg | aggctgcgcc | cctggacgga gtcctggcca | acccacctaa catttccagc | 180 |
| ctctcccctc | gccaactcct | tggcttcccg tgtgcgagg | tgtccggcct gagcacggag | 240 |
| cgtgtccggg | agctggctgt | ggccttggca cagaagaatg | tcaagctctc aacagagcag | 300 |
| ctgcgctgtc | tggctcaccg | gctctctgag cccccgagg | acctgacgc cctcccattg | 360 |
| gacctgctgc | tattcctcaa | cccagatgcg ttctcggggc | ccaggcctg cacccgtttc | 420 |
| ttctcccgca | tcacgaaggc | caatgtggac ctgctcccga | gggggctcc cgagcgacag | 480 |
| cggctgctgc | ctgcggctct | ggcctgctgg ggtgtgcggg | ggtctctgct gagcgaggct | 540 |
| gatgtgcggg | ctctgggagg | cctggcttgc gacctgcctg | ggcgctttgt ggccgagtcg | 600 |
| gccgaagtgc | tgctaccccg | gctggtgagc tgcccgggac | ccctggacca ggaccaacag | 660 |
| gaggcagcca | gggcggctct | gcagggcggg ggacccccct | acggcccccc gtcgacatgg | 720 |
| tctgtctcca | cgatggacgc | tctgcggggc ctgctgcccg | tgctgggcca gcccatcatc | 780 |
| cgcagcatcc | gcagggcat | cgtgccgcg tggcggcaac | gctcctctcg ggacccatcc | 840 |
| tggcggcagc | ctgaacggac | catcctccgg ccgcggttcc | ggcgggaagt ggagaagaca | 900 |
| gcctgtcctt | caggcaagaa | ggcccgcgag atagacgaga | gcctcatctt ctacaagaag | 960 |
| tgggagctgg | aagcctgcgt | ggatgcggcc ctgctggcca | cccagatgga ccgcgtgaac | 1020 |
| gccatcccct | tcacctacga | gcagctggac gtcctaaagc | ataaactgga tgagctctac | 1080 |
| ccacaaggtt | accccgagtc | tgtgatccag cacctgggct | acctcttcct caagatgagc | 1140 |
| cctgaggaca | ttcgcaagtg | gaatgtgacg tccctggaga | ccctgaaggc tttgcttgaa | 1200 |
| gtcaacaaag | gcacgaaat | gagtcctcag gctcctcggc | ggcccctccc acaggtggcc | 1260 |
| accctgatcg | accgctttgt | gaagggaagg ggccagctag | acaaagacac cctagacacc | 1320 |
| ctgaccgcct | tctaccctgg | gtacctgtgc tccctcagcc | cgaggagct gagctccgtg | 1380 |
| cccccccagca | gcatctgggc | ggtcaggccc caggacctgg | acacgtgtga cccaaggcag | 1440 |
| ctggacgtcc | tctatcccaa | ggccgcctt gctttccaga | acatgaacgg gtccgaatac | 1500 |
| ttcgtgaaga | tccagtcctt | cctgggtggg gcccccacgg | aggatttgaa ggcgctcagt | 1560 |
| cagcagaatg | tgagcatgga | cttggccacg ttcatgaagc | tgcggacgga tgcggtgctg | 1620 |

```
ccgttgactg tggctgaggt gcagaaactt ctgggacccc acgtggaggg cctgaaggcg    1680
gaggagcggc accgcccggt gcgggactgg atcctacggc agcggcagga cgacctggac    1740
acgctggggc tggggctaca gggcggcatc cccaacggct acctggtcct agacctcagc    1800
atgcaagagg ccctctcggg gacgccctgc ctcctaggac ctggacctgt tctcaccgtc    1860
ctggcactgc tcctagcctc caccctggcc tga                                 1893

<210> SEQ ID NO 12
<211> LENGTH: 2109
<212> TYPE: DNA
<213> ORGANISM: human

<400> SEQUENCE: 12
atggagtctc cctcggcccc tccccacaga tggtgcatcc cctggcagag gctcctgctc      60
acagcctcac ttctaacctt ctggaacccg cccaccactg ccaagctcac tattgaatcc     120
acgccgttca atgtcgcaga ggggaaggag gtgcttctac ttgtccacaa tctgccccag     180 catcttttg gctacagctg gtacaaaggt gaaagagtgg atggcaaccg tcaaattata      240
ggatatgtaa taggaactca acaagctacc ccagggcccg catacagtgg tcgagagata     300 atataccccca atgcatccct gctgatccag aacatcatcc agaatgacac aggattctac    360
accctacacg tcataaagtc agatcttgtg aatgaagaag caactggcca gttccgggta    420
tacccggagc tgcccaagcc ctccatctcc agcaacaact ccaaacccgt ggaggacaag     480
gatgctgtgg ccttcacctg tgaacctgag actcaggacg caacctacct gtggtgggta     540
aacaatcaga gcctcccggt cagtcccagg ctgcagctgt ccaatggcaa caggaccctc     600
actctattca atgtcacaag aaatgacaca gcaagctaca atgtgaaac ccagaaccca      660 gtgagtgcca ggcgcagtga ttcagtcatc ctgaatgtcc tctatggccc ggatgccccc    720
accatttccc ctctaaacac atcttacaga tcaggggaaa atctgaacct tcctgccac    780 gcagcctcta cccacctgc acagtactct tggtttgtca atgggacttt ccagcaatcc     840
acccaagagc tctttatccc caacatcact gtgaataata gtggatccta cgtgccaa     900 gcccataact cagacactgg cctcaatagg accacagtca cgacgatcac agtctatgca    960
gagccaccca aaccttcat caccagcaac aactccaacc ccgtggagga tgaggatgct    1020
gtagccttaa cctgtgaacc tgagattcag aacacaacct acctgtggtg ggtaaataat    1080
cagagcctcc cggtcagtcc caggctgcag ctgtccaatg acaacaggac cctcactcta    1140
ctcagtgtca caaggaatga tgtaggaccc tatgagtgtg aatccagaa caaattaagt    1200 gttgaccaca gcgacccagt catcctgaat gtcctctatg gcccagacga ccccaccatt    1260 tcccctcat acacctatta ccgtccaggg gtgaacctca gcctctcctg ccatgcagcc    1320
tctaacccac ctgcacagta ttcttggctg attgatggga acatccagca acacacacaa    1380
gagctcttta tctccaacat cactgagaag acagcggac tctataacctg ccaggccaat    1440 aactcagcca gtgccacag caggactaca gtcaagacaa tcacagtctc tgcggagctg    1500
cccaagccct ccatctccag caacaactcc aaacccgtgg aggacaagga tgctgtggcc    1560
ttcacctgtg aacctgaggc tcagaacaca acctacctgt ggtgggtaaa tggtcagagc    1620
ctcccagtca gtcccaggct gcagctgtcc aatggcaaca ggaccctcac tctattcaat    1680
gtcacaagaa atgacgcaag agcctatgta tgtggaatcc agaactcagt gagtgcaaac    1740
cgcagtgacc cagtcaccct ggatgtcctc tatgggccgg acacccccat catttccccc    1800
ccagactcgt cttacctttc gggagcgaac ctcaacctct cctgccactc ggcctctaac    1860
```

-continued

```
ccatccccgc agtattcttg gcgtatcaat gggataccgc agcaacacac acaagttctc      1920
tttatcgcca aaatcacgcc aaataataac gggacctatg cctgttttgt ctctaacttg      1980
gctactggcc gcaataattc catagtcaag agcatcacag tctctgcatc tggaacttct      2040
cctggtctct cagctggggc cactgtcggc atcatgattg agtgctggt tggggttgct       2100 ctgatatag                                                              2109
```

<210> SEQ ID NO 13
<211> LENGTH: 1683
<212> TYPE: DNA
<213> ORGANISM: CMV

<400> SEQUENCE: 13

```
atggaatcca gggggaggag gtgtccggag atgatctcag tcctcggacc gattagcggt       60
cacgtgctca aagcggtctt cagcagagga gacactccgg tgctgccgca cgaaacaagg      120
ctccttcaga cggggataca cgtgcgtgtg agtcagccca gcctgatcct cgtgtctcaa      180
tacacccctg acagcactcc ctgtcacaga ggggacaacc aactccaggt ccagcacacc      240
tacttcactg ggagcgaggt cgagaacgtc agcgtgaacg tgcacaaccc cacgggaaga      300
tcaatctgcc ctagccagga gcccatgagc atctacgtgt acgccctccc gctcaagatg      360
ctcaacatcc cctccatcaa cgtccaccac tatccctccg ctgccgaacg taaacaccga      420
cacttgccag ttgcggacgc cgtgatacac gcttcaggga agcagatgtg gcaagccagg      480
cttactgtga gtggactcgc ctggactagg caacagaacc agtggaagga gcccgacgtg      540
tactacacca gcgccttcgt gttccccaca aaagacgtcg cgctgcgaca tgtggtgtgc      600
gctcacgaac tggtgtgcag catggagaac acgcgagcga ccaagatgca ggtgatcggt      660
gaccagtacg tcaaggtgta cctggagagc ttctgcgagg atgtcccgtc cggaaagctg      720
ttcatgcacg tgaccctggg cagtgacgtt gaggaagacc tgaccatgac gcgtaacccg      780 cagccttca tgagaccgca cgagaggaac ggattcaccg tcctgtgccc gaagaacatg      840
atcatcaagc ccggcaagat cagccacatc atgctcgacg tcgccttcac ctctcacgaa      900
cacttcgggc tgctgtgtcc gaagagcatt ccgggtctga gcatctcagg caacctgctg      960
atgaacgggc agcagatctt cctggaagtg caggccataa gggagaccgt ggaactgagg     1020
cagtacgatc ctgtggctgc cctgttcttc ttcgacatcg acctcttgct gcaaggggtt     1080
ccacagtata gcgaacaccc caccttcacc tcccagtacc gtatccaggg caagctggag     1140
taccgacaca cttgggatag gcacgacgag ggtgccgctc aaggtgacga cgatgtttgg     1200
actagcggct ctgatagcga cgaagagctg gtgaccactg agcgcaaaac tccaagagtt     1260
acgggcggcg gcgcaatggc tggcgcctct acttccgcgg gaaggaaaag gaaaagcgcg     1320
tctagcgcaa ctgcatgcac tgccggtgtg atgacaaggg ggagactgaa ggccgagagt     1380
acagtggctc cggaagagga taccgacgag gactctgaca cgagatccaa caccccgca      1440 gtgtttacgt ggccaccttg gcaagccggc atccttgcta gaaacctggt gcccatggtg     1500
gccacagtcc aaggccagaa cctgaagtac caggagttct tctgggacgc caacgacatc     1560
taccgtatct tcgccgaact tgaaggcgtc tggcagccgg cggctcaacc caaaaggaga     1620
cgtcacagac aggacgcgct tcccggaccc tgtattgcct ctaccccaa gaaacaccgg      1680 ggc                                                                   1683
```

<210> SEQ ID NO 14

<211> LENGTH: 1683
<212> TYPE: DNA
<213> ORGANISM: artificial
<220> FEATURE:
<223> OTHER INFORMATION: mutated CMV pp65 cDNA

<400> SEQUENCE: 14

| | | |
|---|---|---|
| atggaatcca gggggaggag gtgtccggag atgatctcag tcctcggacc gattagcggt | 60 |
| cacgtgctca aagcggtctt cagcagagga gacactccgg tgctgccgca cgaaacaagg | 120 |
| ctccttcaga cggggataca cgtgcgtgtg agtcagccca gcctgatcct cgtgtctcaa | 180 |
| tacaccctg acagcactcc ctgtcacaga ggggacaacc aactccaggt ccagcacacc | 240 |
| tacttcactg ggagcgaggt cgagaacgtc agcgtgaacg tgcacaaccc cacgggaaga | 300 |
| tcaatctgcc ctagccagga gcccatgagc atctacgtgt acgccctccc gctcaagatg | 360 |
| ctcaacatcc cctccatcaa cgtccaccac tatccctccg ctgccgaacg taaacaccga | 420 |
| cacttgccag ttgcggacgc cgtgatacac gcttcaggga agcagatgtg gcaagccagg | 480 |
| cttactgtga gtggactcgc ctggactagg caacagaacc agtggaagga gcccgacgtg | 540 |
| tactacacca gcgccttcgt gttccccaca aaagacgtcg cgctgcgaca tgtggtgtgc | 600 |
| gctcacgaac tggtgtgcag catggagaac acgcgagcga ccaagatgca ggtgatcggt | 660 |
| gaccagtacg tcaaggtgta cctggagagc ttctgcgagg atgtcccgtc cggaaagctg | 720 |
| ttcatgcacg tgaccctggg cagtgacgtt gaggaagacc tgaccatgac gcgtaacccg | 780 |
| cagcctttca tgagaccgca cgagaggaac ggattcaccg tcctgtgccc gaagaacatg | 840 |
| atcatcaagc ccgggcaagat cagccacatc atgctcgacg tcgccttcac ctctcacgaa | 900 |
| cacttcgggc tgctgtgtcc gaagagcatt ccgggtctga gcatctcagg caacctgctg | 960 |
| atgaacgggc agcagatctt cctggaagtg caggccataa gggagaccgt ggaactgagg | 1020 |
| cagtacgatc ctgtggctgc cctgttcttc ttcgacatcg acctcttgct gcaaaggggt | 1080 |
| ccacagtata gcgaacaccc caccttcacc tcccagtacc gtatccaggg caagctggag | 1140 |
| taccgacaca cttgggatag gcacgacgag ggtgccgctc aaggtgacga cgatgtttgg | 1200 |
| actagcggct ctgatagcga cgaagagctg gtgaccactg agcgcaaaac tccaagagtt | 1260 |
| acgggcggcg gcgcaatggc tggcgcctct acttccgcgg aaggaacag gaaaagcgcg | 1320 |
| tctagcgcaa ctgcatgcac tgccggtgtg atgacaaggg ggagactgaa ggccgagagt | 1380 |
| acagtggctc cggaagagga taccgacgag gactctgaca cgagatccaa caccccgca | 1440 |
| gtgtttacgt ggccaccttg gcaagccggc atccttgcta gaaacctggt gcccatggtg | 1500 |
| gccacagtcc aaggccagaa cctgaagtac caggagttct tctgggacgc aacgacatc | 1560 |
| taccgtatct tcgccgaact tgaaggcgtc tggcagccgg cggctcaacc caaaaggaga | 1620 |
| cgtcacagac aggacgcgct tcccggaccc tgtattgcct ctaccccaa gaaacaccgg | 1680 |
| ggc | 1683 |

<210> SEQ ID NO 15
<211> LENGTH: 1608
<212> TYPE: DNA
<213> ORGANISM: artificial
<220> FEATURE:
<223> OTHER INFORMATION: mutated CMV pp65 cDNA

<400> SEQUENCE: 15

| | | |
|---|---|---|
| atggaatcca gggggaggag gtgtccggag atgatctcag tcctcggacc gattagcggt | 60 |
| cacgtgctca aagcggtctt cagcagagga gacactccgg tgctgccgca cgaaacaagg | 120 |

```
ctccttcaga cggggataca cgtgcgtgtg agtcagccca gcctgatcct cgtgtctcaa    180
tacacccctg acagcactcc ctgtcacaga ggggacaacc aactccaggt ccagcacacc    240
tacttcactg ggagcgaggt cgagaacgtc agcgtgaacg tgcacaaccc cacgggaaga    300
tcaatctgcc ctagccagga gcccatgagc atctacgtgt acgccctccc gctcaagatg    360
ctcaacatcc cctccatcaa cgtccaccac tatccctccg ctgccgaacg taaacaccga    420
cacttgccag ttgcggacgc cgtgatacac gcttcaggga agcagatgtg gcaagccagg    480
cttactgtga gtggactcgc ctggactagg caacagaacc agtggaagga gcccgacgtg    540
tactacacca gcgccttcgt gttccccaca aaagacgtcg cgctgcgaca tgtggtgtgc    600
gctcacgaac tggtgtgcag catggagaac acgcgagcga ccaagatgca ggtgatcggt    660
gaccagtacg tcaaggtgta cctggagagc ttctgcgagg atgtcccgtc cggaaagctg    720
ttcatgcacg tgaccctggg cagtgacgtt gaggaagacc tgaccatgac gcgtaacccg    780
cagccttcca tgagaccgca cgagaggaac ggattcaccg tcctgtgccc gaagaacatg    840
atcatcaagc ccggcaagat cagccacatc atgctcgacg tcgccttcac ctctcacgaa    900
cacttcgggc tgctgtgtcc gaagagcatt ccgggtctga gcatctcagg caacctgctg    960
atgaacgggc agcagatctt cctggaagtg caggccataa gggagaccgt ggaactgagg    1020
cagtacgatc ctgtggctgc cctgttcttc ttcgacatcg acctcttgct gcaaggggt     1080
ccacagtata gcgaacaccc caccttcacc tcccagtacc gtatccaggg caagctggag    1140
taccgacaca cttgggatag gcacgacgag ggtgccgctc aaggtgacga cgatgtttgg    1200
actagcggct ctgatagcga cgaagagctg gtgaccactg agcgcaaaac tccaagagtt    1260
acgggcggcg gcgcaatggc tggcgcctct acttccgcgg gaaggaacag gaaaagcgcg    1320
tctagcgcaa ctgcatgcac tgccggtgtg atgacaaggg ggagactgaa ggccgagagt    1380
acagtggctc cggaagagga taccgacgag gactctgaca cgagatccaa caccccgca    1440
gtgtttacgt ggccaccttg gcaagccggc atccttgcta gaaacctggt gcccatggtg    1500
gccacagtcc aaggccagaa cctgaagtac caggagttct tctgggacgc caacgacatc    1560
taccgtatct tcgccgaact tgaaggcgtc tggcagccgg cggctcaa                1608
```

<210> SEQ ID NO 16
<211> LENGTH: 10
<212> TYPE: PRT
<213> ORGANISM: Artificial sequence
<220> FEATURE:
<223> OTHER INFORMATION: Synthetic peptide

<400> SEQUENCE: 16

Ser Tyr Gln Tyr Gly Thr Met Gln Thr Leu
1               5                   10

<210> SEQ ID NO 17
<211> LENGTH: 10
<212> TYPE: PRT
<213> ORGANISM: Artificial sequence
<220> FEATURE:
<223> OTHER INFORMATION: Synthetic peptide

<400> SEQUENCE: 17

Lys Tyr Leu Ser Tyr Pro Ala Pro Asp Ile
1               5                   10

<210> SEQ ID NO 18

```
<211> LENGTH: 9
<212> TYPE: PRT
<213> ORGANISM: Artificial sequence
<220> FEATURE:
<223> OTHER INFORMATION: Synthetic peptide

<400> SEQUENCE: 18

Arg Phe Val Pro Asp Gly Asn Arg Ile
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Thr Tyr Gln Ser Ile Met Tyr Ile Val
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic peptide

<400> SEQUENCE: 20

Asp Phe Leu Thr Leu Glu His Leu Ile
1               5

<210> SEQ ID NO 21
<211> LENGTH: 9
<212> TYPE: PRT
<213> ORGANISM: Artificial sequence
<220> FEATURE:
<223> OTHER INFORMATION: Synthetic peptide

<400> SEQUENCE: 21

Val Ile Leu Thr Asn Pro Ile Ser Met
1               5

<210> SEQ ID NO 22
<211> LENGTH: 10
<212> TYPE: PRT
<213> ORGANISM: Artificial sequence
<220> FEATURE:
<223> OTHER INFORMATION: Synthetic peptide

<400> SEQUENCE: 22

Phe Ser Asn Ser Thr Asn Asp Ile Leu Ile
1               5                   10

<210> SEQ ID NO 23
<211> LENGTH: 9
<212> TYPE: PRT
<213> ORGANISM: Artificial sequence
<220> FEATURE:
<223> OTHER INFORMATION: Synthetic peptide

<400> SEQUENCE: 23

Cys Gly Ile Gln Asn Ser Val Ser Ala
1               5

<210> SEQ ID NO 24
<211> LENGTH: 10
```

```
<212> TYPE: PRT
<213> ORGANISM: Artificial sequence
<220> FEATURE:
<223> OTHER INFORMATION: Synthetic peptide

<400> SEQUENCE: 24

Leu Gln Leu Ser Asn Gly Asn Arg Thr Leu
1               5                   10

<210> SEQ ID NO 25
<211> LENGTH: 9
<212> TYPE: PRT
<213> ORGANISM: Artificial sequence
<220> FEATURE:
<223> OTHER INFORMATION: Synthetic peptide

<400> SEQUENCE: 25

Cys Gly Ile Gln Asn Lys Leu Ser Val
1               5
```